United States Patent [19]

McCall et al.

[11] Patent Number: 5,506,354

[45] Date of Patent: Apr. 9, 1996

[54] IMIDAZOLYLPIPERAZINYL STEROIDS

[75] Inventors: John M. McCall; Donald E. Ayer, both of Kalamazoo; E. Jon Jacobsen, Plainwell; Frederick J. VanDoornik, Hamilton; John R. Palmer; Harold A. Karnes, both of Kalamazoo, all of Mich.

[73] Assignee: The Upjohn Company, Kalamazoo, Mich.

[21] Appl. No.: 984,302

[22] Filed: Dec. 1, 1992

Related U.S. Application Data

[62] Division of Ser. No. 749,830, Aug. 26, 1991, Pat. No. 5,175,281, which is a division of Ser. No. 229,675, Aug. 8, 1988, Pat. No. 5,099,019, which is a continuation-in-part of Ser. No. 121,822, May 11, 1987, abandoned, which is a continuation-in-part of Ser. No. 888,231, Jul. 29, 1986, abandoned, which is a continuation-in-part of Ser. No. 877,287, Jun. 23, 1986, abandoned, which is a continuation-in-part of Ser. No. 811,058, Dec. 19, 1985, abandoned, which is a continuation-in-part of Ser. No. 775,204, Sep. 12, 1985, abandoned.

[51] Int. Cl.$^6$ .................................................. C07J 43/00
[52] U.S. Cl. ......................................... 540/5; 540/108
[58] Field of Search ................................. 540/5, 108

[56] References Cited

U.S. PATENT DOCUMENTS

| | | | |
|---|---|---|---|
| 2,665,274 | 1/1954 | Conbere | 260/239.5 |
| 2,920,999 | 1/1960 | Agnello et al. | 167/65 |
| 3,144,446 | 8/1964 | Moffett | 260/239.5 |
| 3,455,968 | 7/1969 | Herzog et al. | 260/349 |
| 3,523,942 | 8/1970 | Holden | 260/239.5 |
| 3,539,687 | 11/1970 | Kuhnen et al. | 424/241 |
| 3,558,608 | 1/1971 | Klimstra | 260/239.5 |
| 3,697,509 | 10/1972 | Colton et al. | 260/239.5 |
| 3,705,150 | 12/1972 | Tuba et al. | 260/239.5 |
| 3,856,956 | 12/1974 | Oxley et al. | 424/243 |
| 3,936,464 | 2/1976 | Allen, Jr. et al. | 260/293.6 |
| 3,983,111 | 9/1976 | Phillips et al. | 260/239.5 |
| 3,998,829 | 12/1976 | Phillips et al. | 260/239.5 |
| 4,013,688 | 3/1977 | Babcock et al. | 260/397.45 |
| 4,022,783 | 5/1977 | Shroff et al. | 544/370 |
| 4,041,055 | 8/1977 | Shephard et al. | 260/397.3 |
| 4,076,737 | 2/1978 | Anner et al. | 260/397.45 |
| 4,101,545 | 7/1978 | Tuba et al. | 260/239.5 |
| 4,191,759 | 3/1980 | Johnston et al. | 424/242 |
| 4,192,871 | 3/1980 | Phillipps et al. | 424/241 |
| 4,336,200 | 6/1982 | Ayer et al. | 260/397.45 |
| 4,377,584 | 3/1983 | Rasmusson et al. | 424/258 |
| 4,381,307 | 4/1983 | Sloan | 424/271 |
| 4,409,223 | 10/1983 | Riblet et al. | 424/251 |
| 4,421,753 | 12/1983 | Tomcufcik et al. | 424/250 |
| 4,456,602 | 6/1984 | Anderson et al. | 424/243 |
| 4,492,696 | 1/1985 | Reginier et al. | 260/243.3 |
| 4,500,461 | 2/1985 | VanRheenen | 260/397.45 |
| 4,524,134 | 6/1985 | Kominek et al. | 435/61 |

FOREIGN PATENT DOCUMENTS

| | | |
|---|---|---|
| 249883 | 10/1966 | Austria . |
| 979894 | 4/1982 | Canada . |
| 49683 | 4/1982 | European Pat. Off. . |
| 90805 | 1/1964 | France . |
| 1413722 | 4/1966 | France . |
| 7031M | 9/1984 | France . |
| 7253M | 9/1984 | France . |
| 1087598 | 5/1964 | Germany . |
| 3322120 | 7/1980 | Germany . |
| 150350 | 7/1963 | Hungary . |
| 85043068 | 3/1985 | Japan . |
| 594146 | 4/1964 | United Kingdom . |
| 954146 | 4/1964 | United Kingdom . |
| 1390014 | 4/1965 | United Kingdom . |
| 1345640 | 7/1965 | United Kingdom . |
| 2136293 | 9/1984 | United Kingdom . |

OTHER PUBLICATIONS

*Canadian Journal of Chemistry*, 47, 160–163 (1969), O. H. Wheeler and C. Reyes–Zamora, "Steroid derivatives of cysteamine and cysteine."*Journ. Med. Chem.*, 27, 1690–1701 (1983), Gary H. Rasmusson, et al., "Azasteroids as Inhibitors of Rat Prostatic 5α–Reductase."*Chem. Biol. Interactions*, 46, 1–9 (1983), G. Defaye, et al., "Progesterone–Binding Globulin Interaction with its Steroid Ligands: Study of the Protein Binding Site . . . ".
*J. Steroid Biochem.*, 20, 1095–1100 (1984), J. H. MacIndoe, et al., "Comparative Studies of 5α–Reductase Inhibitors within MCF–7 Human Breast Cancer Cells."*Inorganica Chimica Acta*, 91, 257–261 (1984), Ottavio Gandolfi, et al., "Antitumor Steroidal–cis–Platinum (II)–o–Catecholato Conjugates: Preliminary Evaluation on Breast Cancer MCF–7 Cells."*Steroids*, 35, 265–272 (1980), P. Formstecher, et al., "Synthesis of Steroidal 17β–Carboxamide Derivatives."*Biochimica et Biophysica Acta*, 623, 280–294 (1980), G. Defaye, et al., "Electron Spin Resonance Study of Human Transcortin Thiol Groups and Binding Site Topography."*Protides Biol. Fluids*, 29, 393–396 (1982), P. Formstecher, et al., "Structure–Activity–Relationships in the Steroidal 17β–Carboxamide Series."*J. Clin. Chem. Clin. Biochem.*, 22, 209–214 (1984), B. Manz, et al., "17β–Carboxamide Steroids: Highly Effective Inhibitors of the Phytohaemagglutinin Mediated Blastogenesis of Normal Human Peripheral Lymphocytes."*Eur. J. Biochem.*, 108, 47–53 (1980), Manjapra V. Govindan, et al., "Three–Step Purification of Glucocorticoid Receptors from Rat Liver."*Journ. of Steroid Biochemistry*, 14, 697–703 (1981) Patrick Lustenberger, et al., "Purification of Rat Liver Glucocorticoid Receptor by Affinity Chromatography: Design of a Suitable Adsorbent."*Nature*, 279, 158–160 (1979) G. G. Rousseau, et al., "17β–Carboxamide steroids are a new class of glucocorticoid antagonists."*Eur. J. Biochem.*, 131, 333–338 (1983) Bernhard Manz, et al., "Synthesis of Biotin–Labelled Dexamethasone Derivatives."*J. Clin. Chem. Clin. Biochem.*, 21, pp. 69–75 (1983), B. Manz et al., "17β–Carboxyester Derivatives of Natural and Synthetic Glucocorticoids: Correlation Between Receptor Binding and Inhibition of in vitro . . . ".

(List continued on next page.)

*Primary Examiner*—Richard D. Lovering
*Assistant Examiner*—Catherine Scalzo
*Attorney, Agent, or Firm*—Bruce Stein

[57] ABSTRACT

Disclosed are amino substituted steroids (XI) which contain an imidazolylpiperazinyl group attached to the terminal carbon atom of the $C_{17}$-side chain which are useful as pharmaceutical agents for treating a number of conditions.

4 Claims, No Drawings

OTHER PUBLICATIONS

*J. Org. Chem.*, 45, 3084–3088 (1980) S. Stoney Simons, Jr., et al., "α–Keto Mesylate: A Reactive, Thiol–Specific Functional Group.".

*J. Org. Chem.*, 26, 1223–1227 (1961) R. E. Schaub and M. J. Weiss, "The Synthesis of Certain C–21–Substituted Derivatives of 21–Deoxyhydrocortisone, 21–Deoxy–9α–fluorohydrocortisone, and Progesterone."*J. Org. Chem.*, 26, 5052–5054 (1961) H. D. Brown, et al., "Some 21–Substituted Analogs of Cortisone."*J. Chem. Soc. Perkin Trans.*, I, 502–507 (1972) G. Rapi et al., "Amino–and Dienamino–derivatives formed from Adrenocortical Steroids and Heterocyclic Bases."*Archives of Biochem. and Biophysics*, 182, 197–202 (1977) Daniel W. Chan, et al., "The Chemistry of Human Transcortin."*Khim–Farm.*, 2, 26–29 (1968).

*Int. Conf. Chem. Biotechnol. Biol. Act. Nat. Prod.*, 2, 135–49 (1981), Tuba, Zoltan, "Synthesis of Biologically Active Amino and Aza Steroids and Some of their New Chem. Reactions."*Analyst* (London), 97, 519–522 (1972) S. Gorog and G. Szepesi, "Analysis of Steroids."*Nature*, 191, 607 (1961) J. Toth, Z. Tuba, "Amino–derivatives of 11β–17α, 21–Trihydroxy–3, 20–Dioxo–1,4–Pregnadiene."*Arch. Farmacol. Toxicol.*, 4, 265–272 (1978), by L. Biella De Souza Valle, et al., "Rate recovery of extrahepatic cholesterol levels after chronic treatment with diazacholestanol."*Lipids*, 2, pp. 5–7 (1967), M. Kraml et al. "Agents Affecting Lipid Metabolism . . .".

*J. Med. Chem.*, 15, pp. 1129–1131 (1972), F. Kohen et al., "Hypocholes–terolemic Agents . . .".

*J. Med. Chem.*, 15(12), 1284–1287 (1972) Matthias C. Lu et al., Inhibition "Inhibition of Cholesterol Side–Chain Cleavage.2. Synthesis of Epimeric Azacholesterols."*Lipids*, 11(8), 616–622, (1976), Akira Yamamoto et al., "Studies on Drug–induced Lipidosis: VII. Effects of Bis –β–diethylaminoethylether of Hexestrol . . .".

Chem. Abstracts CA 62:14784 a.
Chem. Abstracts CA 64:14573 e.
Chem. Abstracts CA 65:2334 d.
Chem. Abstracts CA 56:15583 a, b, and i.
Chem. Abstracts CA 57:12574 d.
Chem. Abstracts CA 57:6225 d.
Chem. Abstracts CA 65:20189 g.

*J. Steroid Biochem.*, 9, 1155–1158 (1978), D. T. Zava et al., "Steroid–Nucleoside Interactions with Receptors."*Aldrich*, item P4, 585–0.

*Aldrich*, item M2, 260–1.
*Aldrich*, item M2, 300–4.
*Aldrich*, item 19, 133–7.
*Aldrich*, item 12, 694–2.
*Aldrich*, item D13, 620–4.

*J. Pharm. Sci.*, 60, 1232–33 (1971), K. Bailey, "Analysis of NMR Spectra for Rotamer Populations of Dimethoxyamphetamines."Chem. Abstracts CA 65:7001 f.

*Aldrich*, item A6,520–4.

*J. Chem. Soc. (B).*, 4, 748–752 (1970, W. G. Cole and Dudley H. Williams, "Conformational Preference in the Side Chain of Compounds Related to Cortisone . . .".

*Tetrahedron Lett.*, 25, 2581–84 (1984), D. van Leusen and A. M. van Leusen, "A Novel Method to Build Acetyl and Hydroxyacetyl Side–Chains in 17–Oxosteroids."*J. Org. Chem.*, 50, 81–84 (1985), M. Numazawa and M. Nagaoka, "New Preparation and Controlled Alkaline Hydrolysis of 21–Bromo–20–ketopregnenes. A Facile Synthesis of Deoxycorticoids."*J. Pharm. Sci.*, 74, 365–374 (1985), B. D. Anderson, et al., "Strategies in the Design of Solution––Stable, Water–Soluble Prodrugs I: A Physical–Organic Approach to Pro–Moiety Selection for 21–Esters . . .".

*J. Med. Chem.*, 28, 171–177 (1985), Chung Il Hong, et al., "Nucleoside Conjugates. 6. Synthesis and Comparison of Antitumor Activity of 1–β–D–Arabinofuranosylcytosine Conjugates of Corticosteroids . . .".

*Bull. Chem. Soc. Jpn.*, 58, 981–986 (1985), Issei Nitta, et al., "The Syntheses of the Corticoid Side Chain. III. A New Synthesis of 17α,21–Dihydroxypregna–1,4–diene–3,20–dione . . .".

CA 70, 115402v (1969).
CA 85, 78082c (1976).
CA 65:17017f 1966.
CA 62: 14779c 1965.
CA 62: 14778g 1965.

IMIDAZOLYLPIPERAZINYL STEROIDS

CROSS-REFERENCE TO RELATED APPLICATIONS

The present patent application is a divisional application of U.S. patent application Ser. No. 07/749,830, filed Aug. 26, 1991, now U.S. Pat. No. 5,175,281 which is a divisional application of U.S. patent application Ser. No. 07/229,675, filed Aug. 8, 1988, now U.S. Pat. No. 5,099,019 [filed as Reissue application Ser. No. 07/959,310, filed Oct. 9, 1992], which is a continuation-in-part of U.S. patent application Ser. No. 07/121,822, filed May 11, 1987, which is the National Phase application, now abandoned, which is a continuation-in-part of PCT patent application Ser. No. PCT/US86/01797, filed Aug. 28, 1986, which is a continuation-in-part of U.S. patent application Ser. No. 06/888,231, filed Jul. 29, 1986, now abandoned, which is a continuation-in-part of U.S. patent application Ser. No. 06/877,287, filed Jun. 23, 1986, now abandoned, which is a continuation-in-part of U.S. patent application Ser. No. 06/811,058, filed Dec. 19, 1985, now abandoned, which is a continuation-in-part of U.S. patent application Ser. No. 06/775,204, filed Sep. 12, 1985, now abandoned.

BACKGROUND OF THE INVENTION

1. Field of the Invention

The present invention relates to amino substituted steroids which are useful as pharmaceutical agents.

2. Description of the Related Art

Various amino (substituted) steroids are known with the amine substitution on either the steroidal ring system or on the side chain of the D-ring at $C_{17}$.

U.S. Pat. No. 4,456,602 discloses steroidal 21-esters in which there is an amino function in the non-steroidal portion of the ester.

In the 3α-hydroxy series, U.S. Pat. No. 3,998,829 discloses 21-aminomethyl steroids and U.S. Pat. No. 3,983,111 discloses 21-amino steroids where the amino group is cyclized. These patents also disclose reduced A-ring steroids as well as steroids with a hydrogen atom at $C_{17}$ and two hydrogen atoms at $C_{11}$.

20-Amino steroids are known in the $\Delta^4$-3-keto series with no substitution at $C_{11}$ and $C_{17}$, see *Can. J. Chem.*, 47, 160 (1969); *J. Med. Chem.*, 27, 1690 (1983); U.S. Pat. Nos. 4,377,584 and 4,191,759; *Chem.-Biol. Interact.*, 46, 1 (1983); *J. Steroid Biochem.*, 20, 1095 (1984); *Inorg. Chim. Acta*, 91, 257 (1984), with substitution at $C_{11}$, see *Steroids* 35, 265 (1980) and *Biochim. Biophys. Acta*, 623, 280 (1980) as well as with substitution at both $C_{11}$ and $C_{17}$, see *Steroids*, supra.

20-Amino steroids are known in the $\Delta^{1,4}$-3-keto series with an 11β-hydroxyl substitution, see *Steroids*, supra, as well as with 11β,17α-dihydroxy substitution, see *Protides Biol. Fluids*, 29, 393 (1982); *J. Clin. Chem. Clin. Biochem.*, 22, 209 (1984); *Eur. J. Biochem.*, 108, 47 (1980); *J. Steroid Biochem.*, 14, 697 (1981), *Nature* (London) 279, 158 (1979) and *Eur. J. Biochem.*, 131, 333 (1983) and with 11α,17α-dihydroxy substitution, see *J. Clin. Chem. Clin. Biochem.*, 21, 69 (1983) U.S. Pat. No. 4,191,759 discloses 20-amino$\Delta^{1,4}$-3-keto steroids without any substitution at the 11 position where the amine substituent is morpholine or piperazine.

21-Amino steroids are known in the $\Delta^4$-3-keto series with no substitution at $C_{11}$, see *J. Org. Chem.*, 45, 3084 (1980); *J. Org. Chem.*, 26, 1223 and 5052 (1961); *J. Chem. Soc., Perkin Trans.* 1, 502 (1972); Great Britain Patent 954,146 and its U.S. equivalent, U.S. Pat. No. 3,123,598; Austrian Patent 249,883; *Arch. Biochem. Biophys.*, 182, 197 (1977) and *Khim.-Farm.* 2, 26 (1968). In addition 21-amino steroids are known in the $\Delta^{1,4}$-3-keto series substituted with 11β-hydroxyl, see *Arch. Biochem. Biophys.*, 182, 197(1977); *Int. Conf. Chem. Biotechnol. Biol. Act. Nat. Prod.* 2, 135–49 (1981); *Analyst* (London) 98, 519 (1972); U.S. Pat. Nos. 3,705,150, 4,076,737 and 2,920,999; *Nature*, 191, 607 (1961); Hungarian Patent 150,350 and *J. Org. Chem.*, 45, 3084 (1980). For example Hungarian Patent 150,350 discloses dipersolone, 11β,17α-dihydroxy-21-(4-methyl-1-piperazinyl)pregna-1,4-diene-3,20-dione. Further, U.S. Pat. No. 3,705,150 discloses 21-[N-(N'-methyl)piperazinyl]prednisolone.

German Patent 1,087,598 and U.S. Pat. No. 2,920,999 disclose simple 21-amino derivatives of $\Delta^4$-3-keto steroids. The amines include both mono and bis substituted amines. In the cases where the amino group is disubstituted, the two substituents can be cyclized with the attached nitrogen atom to form a heterocyclic amino group (morpholine, pyrrolidine, piperidine, pyridine). The amines were chosen from the group consisting of amino, monoalkylamino, dialkylamino, phenylamino, pyridylamino, benzylamino, picolinylamino, N-alkyl-N-phenylamino, N-alkyl-N-pyridylamino, morpholinyl, pyrryl, pyrrolidyl, piperidino and C-alkylated piperidino, though only N-piperidino, N,N-diethyl and N-methyl-N-phenyl were exemplified. The amino steroids of the present invention while containing the steroid portion of the compounds of U.S. Pat. No. 2,920,999, contain more complex amines.

U.S. Pat. No. 3,144,446 discloses mono and bis quaternary ammonium salts of triethylenediamine. The amines and amino steroids of the present invention do not include triethylenediamine or other bridges amine, only 1-piperazinyl substituted amines.

U.S. Pat. No. 2,665,274 discloses pyridium salts of steroids. In the present invention $R_{21}$ and $R_{210}$ are taken together with the attached carbon atom to form a heterocyclic ring but not an aromatic ring.

*Chem. Abst.* 70, 115402v (1969) discloses amino steroids where the amines are morpholino, piperidino and dimethyl. The amines of the amino steroids of the present invention are much more complex than these three simple unsubstituted amines.

A number of 20-amino steroids are known where the 20-amino group is of the general type —NH—$(CH_2)_x$—$N(R_1)(R_2)$ where x is 2 or 3 and $R_1$ and $R_2$ are methyl or ethyl. See, for example, *Arch. Farmacol. Toxicol.* 4, 265 (1978), *Lipids*, 2, 5 (1967), *J. Med. Chem.* 15, 1129 (1972), ibid 15, 1284 (1972), French Patent 90805, *Lipids* 11, 616 (1976), U.S. Pat. No. 3,558,608, *Chem. Abst.* 62, 14784a, ibid 64, 14573e, ibid 65, 2334d, ibid 56, 15583a, b, and i, ibid 57, 12574d, ibid 57, 6225d.

Many 20-amino and 21-amino steroids are known where the amino group is substituted with simple alkyl ($C_1$–$C_3$), aryl (phenyl), simple aralkyl (benzyl), as well as substituents containing hetero atoms (sulfur), esters, acids, amino substituted alkyl, alcohols, ethynyl groups, etc. The amino steroids are known where the amine portion is either mono or disubstituted. In the cases where the amino group is disubstituted, the two substituents can be cyclized with the attached nitrogen atom to form a heterocyclic amino group.

These simple cyclic and heterocyclic amines, see U.S. Pat. Nos. 3,523,942, 4,191,759 and 2,920,999, are unlike the complex amine substituents of the present invention. The known 21-amino substituted steroids include simple (substituted) cyclic amines such as 4-(2-hydroxyethyl)-1-piperazinyl [CA 65;20189g]; 4-(2 -hydroxyethyl)-1-piperidinyl [83544-11-0]; 4,4-dimethyl-1-piperazinyl, 3-hydroxyethyl-1 -piperidinyl, 4-hydroxy-1-piperidinyl, 4-carboxy-1-piperidinyl, 3-hydroxy-1-piperidinyl, 3 -carboxy-1-piperidinyl, piperazinyl, bis(hydroxyethyl)amino, 4-acetyl-1-piperazinyl, 4 -carboxaldehyde-1-piperazinyl, 1-piperidinyl, [Int. Conf. Chem. Biotechnol. Biol. Act. Nat. Prod. [Proc.] 1st. Vol. 2, p. 135, 1981]; 4-methyl-1-piperazinyl [Great Britain Patent 2,136,293]; 3,6 -dihydro-2,6-dioxo-1(2H)-pyrimidinyl, 5-fluoro-3,6-dihydro-2,6-dioxo-1(2H)-pyrimidinyl, 5 -fluoro-3,4-dihydro-2,4-dioxo-1(2H)-pyrimidinyl, 3,4-dihydro-2,4-dioxo-1(2H)-pyrimidinyl, 3,4-dihydro-5-methyl-2,4-dioxo-1(2H)-pyrimidinyl [J. Steroid Biochem. 9, 1155 (1978)]; and 4-morpholinyl [J. Chem. Soc. Perkin Trans 1, 502 (1972)]. The 4-methyl-1-piperazinyl group is a common substitutent at the $C_{21}$ position, see for example Int. Conf. Chem. Biotechnol. Biol. Act. Nat. Prod., 2, 135–49 (1981) [English] at Budapest, Hungary as abstracted in Chemical Abstracts 97(21), 182,723w (1982) which discloses various antiinflammatory 21-amino prednisolones such as 11β,17α-dihydroxy-21-[4-methyl-1-piperazinyl] pregna-1,4-diene-3,20 -dione, DE 2,123,555 as abstracted in Chemical Abstracts 76(11), 59893r (1972) which discloses 11β,17α-dihydroxy-21-[4-methyl-1-piperazinyl]pregna-1, 4-diene-3,20-dione as being useful in the treatment of anaphylactic shock, Acta Pharm. Hung., 37(3) 97–107 (1967) as abstracted in Chemical Abstracts 67(12) 57273d (1967) which discloses 11β,17α-dihydroxy-21-[4-methyl- 1-piperazinyl]pregna-1,4-diene-3,20-dione and Khim.-Farm. Zh., 2(11), 26–9 (1968) as abstracted in Chemical Abstracts 70, 115402v (1969) page 380 which discloses 17α-hydroxy-21-[4-methyl- 1-piperazinyl]pregn-4-ene-3,20-dione as well as the 21-morpholino steroid.

U.S. Pat. No. 3,697,509 discloses $\Delta^{17(20)}$-21-quaternary amino steroid salts. The $\Delta^{17(20)}$-21-amino steroids (V) of the present invention include pharmaceutically acceptable salts, but not quaternary amine salts.

Japanese published application J8 5043068 discloses azepino(1,2,3-1H)-β-carboline derivatives which inhibit lipid peroxidation and are useful in inhibiting the aging of living bodies.

Some of the free amines of the amino substituent of the amino substituted steroids (XI) of the present invention are known. See, for example, U.S. Pat. No. 4,492,696.

U.S. Pat. No. 3,146,234 (ARCHER) discloses 1-[(1-, 2- and 3-indolyl)-substituted piperazines which have anticonvulsant activity, which can be depicted as 1-, 2- or 3-indolinyl]-[ alkyl]$_{0-6}$-PIPERAZINE-$X_2$.

While some of the free amines of the amino steroids of the present invention are known, such as 2-carboxy-1-piperidine [Aldrich, item P4,585-0], 4-(2-pyridinyl)piperazine [French Patent 7253 M], 4-(2-pyridinylmethyl)piperazine [European Patent application 49,683], 4-(6-methoxy- 2-pyridinyl)piperazine [Canadian Patent 679,894], 4-(2-pyrimidinyl)piperazine [U.S. Pat. No. 4,409,223], 4-(3,6-dimethylpyrazinyl)piperazine [Canadian Patent 979,894], 4-(2 -methoxyphenyl)piperazine [Aldrich, item M2,260-1], 4-(4-methoxyphenyl)-piperazine [Aldrich item M2,300-4], 4-[(3, 4-dimethoxyphenyl)methyl]piperazine [French Patent 7031 M], 4-(4 -fluorophenyl)piperazine [Aldrich, item 19,133-7], 4-[[4(dimethylamino)phenyl]methyl]piperazine [U.S. Pat. No. 4,421,753], 4-hydroxy-4-[4-(trifluoromethyl)phenyl] piperazine [U.S. Pat. No. 3,936,464], (2-diethylaminoethyl)amine [Aldrich, item 12,694-2], [2-(3,4-dimethoxyphenyl)ethyl]amine [Aldrich, item D13,620-4], [2-(2,4-dimethoxyphenyl)-1-methylethyl]amine [J. Pharm. Sci. 60, 1232 (1971)], [2-(3,4-dimethoxyphenyl)ethyl][[4-dimethylamino)phenyl]methyl]amine [Chem. Abst. 65:7001f] and (2-pyridinyl)methylamine [Aldrich, item A6,520-4], most are novel.

Great Britain Patent 1,345,640 and U.S. Pat. No. 3,835, 132 generically disclose piperazinyl substituted pyrimidines including those where the substituents are morpholino, monoalkylamino, cycloalkyl, N-benzylpiperazino, —NEt$_2$, —NHCH$_2$CH$_2$OH and piperazino. Specifically disclosed are 4-[2-morpholino-6-ethylamino-4-pyrimidinyl]piperazine (named the same way the amines of the present invention are named), see Example 1 and 4-[4-morpholino-2-ethylamino-4-pyrimidinyl] piperazine, see Example 2.

Great Britain Patent 1,390,014 and U.S. Pat. No. 3,980, 650 disclose 4-aminoquinazolines. The starting material for Example VI is 1-cyano-4-(2-furoyl)piperazine, N≡C-piperazine-(2-furoyl). One of the amines of the present invention is 4-(2-furanylcarbonyl)piperazine, see PREPARATION A-3. The amine of the present invention differs from the prior art amine in that it does not have a cyano group and does not have a carbonyl group between the piperazine and the furoyl substituent.

Chem. Abst. 85, 78082c (1976) discloses 4-(2-furoyl)piperazine, 4-(2-thienyl)piperazine and 4-(3-thienyl)piperazine. The present invention includes 4-(2-furanylcarbonyl)piperazine, see PREPARATION A-3. The amine of the present invention differs from the prior art compounds in that they do not include the thienyl moiety or do have a carbonyl group separating the piperazine from the furoyl group.

French Patent 1,413,722 and U.S. Pat. Nos. 3,325,496 and 3,374,173 disclose 2,4,6-triamino-substituted pyrimidines including bis(dialkylamino)piperidino substituted pyrimidine. The present invention includes piperazinyl substituted pyrimidines, not piperidino substituted pyrimidines.

Most of the steroidal 21-(hydroxy derivative) halo (bromine or iodine), mesylate or tosylate starting materials are known, such as 21-bromo-17α-hydroxypregna-4,9-diene-3,20-dione [U.S. Pat. No. 4,041,055 (Ex 59)], 21-bromo-17α-hydroxypregn-4-ene-3,11,20-trione [J. Chem. Soc. B., 4, 748 (1970)], 11α,21-dihydroxypregn-4-ene-3,20-dione [U.S. Pat. No. 4,013,688], 21-bromo-17α-hydroxypregn-3,20-dione [U.S. Pat. No. 4,500,461], 21-bromopregn-4-ene-3,11,20-trione [U.S. Pat. No. 3,983,111], 21-hydroxypregna-4,9(11),16-triene-3,20-dione [Tetrahedron Lett. 25, 2581 (1984)], 21-iodopregna-4,9(11)-diene-3,20-dione [95288-91-8], 21-bromopregn-4-ene-3,20-dione [J. Org. Chem., 50, 81 (1985), 11β,17α-dihydroxy-21-iodo-6α-methylpregna-1,4-diene-3,20-dione [J. Pharm. Soc., 74, 365 (1985)], 21-bromo-11β,17α-dihydroxypregna-1,4-diene-3,20-dione [U.S. Pat. No. 3,856,956], 17α-hydroxy-21-iodo-16α-methylpregna-1,4,9(11)-triene-3,20-dione [U.S. Pat. No. 3,455,968], 17α,21-dihydroxy-16α-methylpregna-1,4,9(11)-triene-3, 20-dione [West German DE 3,322,120], 17α-Hydroxy-21-iodopregna-1,4-diene-3,11,20-trione [*J. Med. Chem.*, 28, 171 (1985)], 21-bromopregna-1,4-diene-3,20-dione [*Bull. Chem. Soc. Jpn.* 58, 981 (1985)], 17α,21-dihydroxypregna-1,4,9(11)-triene-3,20-dione [West German DE 3,322,120], 17α,21-dihydroxy-16β-methyl-5α-pregn-9(11)-ene-3,20-dione [U.S. Pat. No. 4,336,200] and 21-bromo-3α,17α-dihydroxy-5β-pregnane-11,20-dione [95044-38-5], however some are novel.

SUMMARY OF THE INVENTION

The amino substituted steroids (XI) encompass the amino steroids (Ia and Ib), aromatic steroids (II), $\Delta^{16}$-steroids (IIIa and IIIb), reduced A-ring steroids (IV) and $\Delta^{17(20)}$-steroids (Va and Vb).

Disclosed is an amino substituted steroid of formula (XI) where:

(A-I) $R_6$ is α-$R_{61}$:β-$R_{62}$, $R_{10}$ is α-$R_{101}$:β-$R_{102}$ and $R_7$ is α-H:β-H, where one of $R_{61}$ and $R_{62}$ is —H, and the other is —H, —F, or $C_1$-$C_3$ alkyl, $R_{102}$ is —$CH_3$, $R_{101}$ and $R_5$ taken together are —$(CH_2)_2$—C(=$R_{33}$)—CH= or —CH=CH—CO—CH=, where $R_{33}$ is =O or α-H:β-OR$_{34}$ or α-OR$_{34}$:β-H, where $R_{34}$ is —H, —CO—$CH_3$, —CO—$C_2H_5$, —CO—$C_6H_5$, —CO—O—$CH_3$ or —CO—O—$C_2H_5$;

(A-II) $R_5$ is α-$R_{53}$:β-$R_{54}$, $R_6$ is α-$R_{63}$:β-$R_{64}$, $R_{10}$ is α-$R_{103}$:β-$R_{104}$ and $R_7$ is α-H:β-H, where one of $R_{63}$ and $R_{64}$ is —H, and the other taken together with one of $R_{53}$ and $R_{54}$ forms a second bond between $C_5$ and $C_6$, $R_{104}$ is —$CH_3$, $R_{103}$ and the other of $R_{53}$ and $R_{54}$ taken together is —$(CH_2)_2$—C(H)(OH)—$CH_2$—;

(A-III) $R_{10}$ and $R_5$ taken together are =CH—CH=C(OR$_3$)—CH= where $R_3$ is —H, $C_1$-$C_3$ alkyl, —CO—H, $C_2$-$C_4$ alkanoyl or benzyl, $R_6$ is α-$R_{65}$:β-$R_{66}$ where one of $R_{65}$ and $R_{66}$ is —H, and the other is —H, —F, or $C_1$-$C_3$ alkyl and $R_7$ is α-H:β-H;

(A-IV) $R_5$ is α-$R_{57}$:β-$R_{58}$, $R_6$ is α-$R_{67}$:β-$R_{68}$, $R_7$ is α-H:β-H and $R_{10}$ is α-$R_{107}$:β-$R_{108}$, where one of $R_{57}$ and $R_{58}$ is —H, $R_{107}$ and the other of $R_{57}$ and $R_{58}$ taken together are —$(CH_2)_2$—C(=$R_{33}$)—$CH_2$, where $R_{33}$ is as defined above, $R_{108}$ is —$CH_3$, where one of $R_{67}$ and $R_{68}$ is —H and the other is —H, —F, or $C_1$-$C_3$ alkyl;

(A-V) $R_6$ is $R_{69}$:$R_{610}$, $R_7$ is $R_{79}$:$R_{710}$, $R_{10}$ is α-$R_{109}$:$R_{1010}$, where one of $R_{69}$ and $R_{610}$ is —H and the other taken together with one of $R_{79}$ and $R_{710}$ forms a second bond between $C_6$ and $C_7$, and the other of $R_{79}$ and $R_{710}$ is —H, $R_{1010}$ is —$CH_3$, $R_{109}$ and $R_5$ taken together are —$(CH_2)_2$—C(=$R_{33}$)—CH= or —CH=CH—CO—CH=, where $R_{33}$ is as defined above;

where:

(C-I) $R_{11}$ is α-$R_{111}$:β-$R_{112}$, where one of $R_{111}$ and $R_{112}$ is taken together with $R_9$ to form a second bond between $C_9$ and $C_{11}$ and the other of $R_{111}$ and $R_{112}$ is —H;

(C-II) $R_9$ is —Cl and $R_{11}$ is =O or α-H:β-$R_{114}$ where $R_{114}$ is —Cl or —OH;

(C-III) $R_9$ is —H or —F and $R_{11}$ is =O or α-$R_{115}$:β-$R_{116}$, where one of $R_{115}$ and $R_{116}$ is —H, and the other of $R_{115}$ and $R_{116}$ is —H, —OH or $C_1$-$C_{12}$ alkoxy;

(C-IV) $R_9$ is —H or —F and $R_{11}$ is α—O—CO-$R_{117}$:β-H, where $R_{117}$ is (A) $C_1$-$C_3$ alkyl, (B) $C_1$-$C_{12}$ alkoxy, (C) furanyl, (D) —N$R_{122}R_{123}$, where one of $R_{122}$ and $R_{123}$ is —H, methyl or ethyl and the other is —H, $C_1$-$C_4$ alkyl or phenyl, (E) —$X_3$-$X_1$, where $X_3$ is —O— or a valence bond, where $X_1$ is phenyl optionally substituted with 1 through 2 —Cl, —Br, $C_1$-$C_3$ alkoxy, —COOH, —$NH_2$, $C_1$-$C_3$ alkylamino, di($C_1$-$C_3$)alkylamino, where the alkyl groups are the same or different, 1-pyrrolidinyl-, 1-piperidinyl, 1-hexamethyleneimino-, 1-heptamethyleneimino-, $C_2$-$C_4$ acylamino and —NH—CHO or with 1 —F or —$CF_3$;

where:

(D-I) $R_{16}$ is $R_{161}$:$R_{162}$ and $R_{17}$ is $R_{171}$:$R_{172}$, where one of $R_{161}$ and $R_{162}$ is —H or —$CH_3$ and the other taken together with one of $R_{171}$ and $R_{172}$ forms a second bond between $C_{16}$ and $C_{17}$, and the other of $R_{171}$ and $R_{172}$ is —C(=Z)—$(CH_2)_n$—N$R_{21}R_{210}$, where Z is =O, =CH, or $R_{179}$:-H where $R_{179}$ is —H or —$CH_3$, where n is 0 through 6, where (A) $R_{21}$ is (1) —$(CH_2)_m$—N$R_{211}$—$X_2$, where m is 2, 3 or 4, where $R_{211}$ is —H or $C_1$-$C_3$ alkyl, where $X_2$ is:

[A]

(a) pyridin-2-, 3- or 4-yl or the N-oxide thereof optionally substituted by 1 or 2 $R_{212}$, being the same or different, where $R_{212}$ is (i) —F, (ii) —Cl, (iii) —Br, (iv) $C_1$-$C_5$ alkyl, (v) —$CH_2$—CH=$CH_2$, (vi) —$X_1$, where $X_1$ is as defined above, (vii) —N$R_{213}R_{213}$ where the $R_{213}$'s are the same or different and are —H, $C_1$-$C_3$ alkyl or —$CH_2$—CH=$CH_2$, (viiiα) *$CH_2$—$(CH_2)_q$—$CH_2$—N*— where the atoms marked with an asterisk (*) are bonded to each other resulting in the formation of a ring, where q is 1 through 5, (viiiβ) *$CH_2$—$CH_2$—$(CH_2)_c$—G—$(CH_2)_d$—$CH_2$—$CH_2$—N*— where the atoms marked with an asterisk (*) are bonded to each other insulting in the formation of a ring, where G is —O—, —S—, —SO—, —$SO_2$— or —NH$R_{214}$, where $R_{214}$ is —H, $C_1$-$C_3$ alkyl, or $X_1$ as defined above, where c and d are the same or different and are 0 through 2 with the proviso that the total number of ring carbon atoms is 4, 5 or 6, [a]

(ix) 3-pyrrolin-1-yl, [b]

(x) pyrrol-1-yl optionally substituted with $C_1$-$C_3$ alkyl, [c]

(xi) piperidin-1-yl optionally substituted with 1 or 2 $C_1$-$C_3$ alkyl, [d]

(xii) 1,2,3,6-tetrahydropyridin-1-yl, [e]

(xiii) 1-hexamethyleneimino containing a 3- or 4- double bond or 3- and 5- double bonds, [f]

(xiv) 1,4-dihydro-1-pyridinyl substituted in the 4 position by two $C_1$-$C_3$ alkyl being the same or different, [g]

(xv) —OH, (xvi) $C_1$-$C_3$ alkoxy, (xvii) —N$R_{217}$—$(CH_2)_e$—Q where Q is 2-pyridinyl where $R_{217}$ is —H or $C_1$-$C_3$ alkyl and e is 0 through 3, (1)

(xviii) pyridin-2-, 3- or 4-yl, (b) 1,3,5-triazin-2-yl or the N-oxide thereof optionally substituted at the 4- and/or 6- position with $R_{212}$ is as defined above, (4)

(c) pyrimidin-4-yl or the N-oxide thereof optionally substituted at the 2- and/or 6- position with $R_{212}$ is as defined above, (5)

(d) pyrimidin-2-yl optionally substituted at 4- and/or 6-position with 1 or 2 $R_{212}$ as is defined above, (6)

(e) pyrazin-2-yl optionally substituted with 1 or 2 $R_{212}$ as is defined above, (7)

(f) imidazol-2-yl optionally substituted in the 1 position with $C_1$–$C_3$ alkyl or —$X_1$, where $X_1$ is as defined above, and further optionally substituted with 1 or 2 $R_{212}$ as defined above, (8)

(g) 1,3,4-triazol-2-yl optionally substituted in the 1-position with $C_1$–$C_3$ alkyl or —$X_1$, where $X_1$ is as defined above, and further optionally substituted with $R_{212}$ as defined above, (9)

(h) imidazol-4 or 5-yl optionally substituted in the 1-position with $C_1$–$C_3$ alkyl or —$X_1$, where $X_1$ is as defined above, and further optionally substituted with 1 or 2 $R_{212}$ as defined above, (10)

(i) benzo[b]thien-2-yl, (12a)

(j) indol-2-yl, (12b)

(k) benzo[b]thiazol-2-yl, (12c)

(l) benzimidazol-2-yl, (12d)

(m) 4-[2-[4-[2,6-bis(1-pyrrolidinyl)-4-pyrimidinyl]-1-piperazinyl]ethyl]piperazinyl, (13)

(n) 1,2,4-triazol-3-yl optionally substituted at the 5- and/or 6- position with $R_{212}$ as is defined above, (14)

(2) (1-piperazinyl)-($C_2$–$C_4$)alkyl optionally substituted in the 4-position with —$X_1$ or —$X_2$ as defined above, [B]

(4) —$(CH_2)_m$—$X_4$ where m is as defined above and where $X_4$ is (a) —O—$CH_2CH_2$—Y, where Y is $C_1$–$C_3$ alkylamino, di($C_1$–$C_3$)alkylamino where the alkyl groups are the same or different, $C_3$–$C_6$ alkyleneimino, optionally substituted will 1 or 2 $C_1$–$C_3$ alkyl, (b) —$NR_{220}CH_2CH_2$—Y, where $R_{220}$ is —H or $C_1$–$C_3$ alkyl and Y is as defined above, (c) —$(CH_2)_g$—$N(R_{220})$—$X_2$, where g is 2, 3 or 4, and where $R_{220}$ and $X_2$ are as defined above, [H]

(5) —$(CH_2)_m$—$NR_{222}R_{223}$, where $R_{222}$ is —H or $C_1$–$C_3$ alkyl and $R_{223}$ is —$X_1$ or —$X_2$ as defined above, or $R_{222}$ and $R_{223}$ are taken together with the attached nitrogen atom to form a saturated mono-nitrogen $C_3$–$C_6$ heterocyclic ring and where m is as defined above, [I]

(6) —$(CHCH_3)_b$—$(CH_2)_f$—$R_{224}$, where b is 0 and f is 1 through 3 or b is one and f is 0 through 3, where $R_{224}$ is phenyl substituted with 1 through 3 —OH, $C_1$–$C_3$ alkoxy, —$NR_{225}R_{226}$ where $R_{225}$ and $R_{226}$ are the same or different and are —H, $C_1$–$C_3$ alkyl or are taken together with the attached nitrogen atom to form a $C_{4-C7}$ cyclicamino ring, [J]

(7) —$(CH_2)_i$—$X_2$, where i is 1 through 4 and $X_2$ is as defined above, [K]

(8) (1-piperazinyl)acetyl substituted in the 4- position by $X_2$ where $X_2$ is as defined above, [L]

(9) (1-piperazinyl)carbonylmethyl substituted in the 4- position by —$X_2$ where $X_2$ is as defined above, and [M]

(B) $R_{210}$ is (1) —H, (2) $C_1$–$C_3$ alkyl, (3) $C_5$–$C_7$ cycloalkyl, (4) —$(CH_2)_m$—$NR_{211}$—$X_2$, where m, $R_{221}$ and $X_2$ are as defined above, [A]

(5) (1-piperazinyl)-($C_2$–$C_4$)alkyl optionally substituted in the 4-position with —$X_1$ or —$X_2$ as defined above, [B]

(6) —$(CH_2)_m$—$X_4$, where m and $X_4$ are as defined above, [H]

(7) —$(CH_2)_m$—$NR_{222}R_{223}$, where m, $R_{222}$ and $R_{223}$ are as defined above, [I]

(8) —$(CHCH_3)_b$—$(CH_2)_f$—$R_{224}$, where b, f and $R_{224}$ are as defined above, [J]

(C) $R_{21}$ and $R_{210}$ are taken together with the attached nitrogen atom to form a heterocyclic ring selected from the group consisting of (1) 2-(carboxy)-1-pyrrolidinyl optionally as the $C_1$–$C_3$ alkyl ester or as a pharmaceutically acceptable salt [C-1]

(2) 2-(carboxy)-1-piperidinyl optionally as the $C_1$–$C_3$ alkyl ester or as a pharmaceutically acceptable salt, [C-2]

(3) 2-(carboxy)-1-hexamethyleneimino optionally as the $C_1$–$C_3$ alkyl ester or as a pharmaceutically acceptable salt, [C-3]

(4) 2-(carboxy)-1-heptamethyleneimino optionally as the $C_1$–$C_3$ alkyl ester or as a pharmaceutically acceptable salt, [C-4]

(5) 1-piperazinyl substituted in the 4- position with $R_{228}$—CO—$(CH_2)_j$— where $R_{228}$ is —$X_1$, —$NR_{229}X_1$ and 2-furanyl, where $R_{229}$ is —H or $C_1$–$C_3$ alkyl, where j is 0 through 3 and $X_1$ is as defined above, [D]

(6) 1-piperazinyl substituted in the 4- position with $X_2$—$(CH_2)_j$—, where $X_2$ and j are as defined above, [E]

(7) 1-piperazinyl substituted in the 4- position with $X_1$—$(CH_2)_j$—, where $X_1$ and j are as defined above, [F]

(8) 4-hydroxy-1-piperidinyl substituted in the 4-position with $X_1$ as defined above, [G]

(9) 1-piperazinyl substituted in the 4- position with $X_2$—$NR_{229}$—CO—$(CH_2)_i$—, where $X_2$, $R_{229}$ and i are as defined above; [N]

(D-II) $R_{16}$ is $\alpha$-$R_{163}$:$\beta$-$R_{164}$ where one of $R_{163}$ and $R_{164}$ is —H and the other is —H, —F, —$CH_3$ or —OH, and $R_{17}$ is =CH—$(CH_2)_p$—$NR_{21}R_{210}$, where p is 1 or 2, where $R_{21}$ and $R_{210}$ are as defined above;

(D-III) $R_{16}$ is $\alpha$-$R_{165}$:$\beta$-$R_{166}$ and $R_{17}$ is $\alpha$-$R_{175}$:$\beta$-$R_{176}$, where $R_{165}$ is —H, —OH, —F or —$CH_3$ and $R_{166}$ is —H, —OH, —F, or —$CH_3$, with the proviso that at least one of $R_{165}$ and $R_{166}$ is —H, where $R_{175}$ is —H, —OH, —$CH_3$, —$CH_2CH_3$, $C_2$–$C_7$ alkanoyloxy or —O—CO—$X_1$, where $X_1$ is as defined above, and where $R_{176}$ is —C(=Z)—$(CH_2)_n$—$NR_{21}R_{210}$, where Z, n, $R_{21}$ and $R_{210}$ are as defined above;

(D-IV) the 16,17-acetonide of a compound where $R_{165}$ is —OH, $R_{166}$ is —H, $R_{175}$ is —OH and $R_{176}$ is —C(=Z)—$(CH_2)_n$—$NR_{21}R_{210}$, where Z, n, $R_{21}$ and $R_{210}$ are as defined above;

and pharmaceutically acceptable salts thereof, and hydrates and solvates thereof;

with the following overall provisos that:

(I) one of $R_{161}$ or $R_{162}$ is taken together with one of $R_{171}$ or $R_{172}$ to form a second bond between $C_{16}$ and $C_{17}$, only when $R_{10}$ is $\alpha$-$R_{101}$:$\beta$-$R_{102}$, $\alpha$-$R_{103}$:$\beta$-$R_{104}$, $\alpha$-$R_{107}$:$\beta$-$R_{108}$ or $\alpha$-$R_{109}$:$\beta$-$R_{1010}$, (II) $R_{17}$ is =CH—$(CH_2)_p$—$NR_{21}R_{210}$, only when $R_{10}$ is $\alpha$-$R_{101}$:$\beta$-$R_{102}$, $\alpha$-$R_{103}$:$\beta$-$R_{104}$, $\alpha$-$R_{107}$:$\beta$-$R_{108}$ or $\alpha$-$R_{109}$:$\beta$-$R_{1010}$, (III) $R_5$ and $R_{10}$ taken together are =CH—CH=C(OR$_3$)—CH=, only when $R_{17}$ is α-$R_{175}$:β-$R_{176}$ or the 16,17-acetonide of a compound where $R_{16}$ is α-OH:β-H and $R_{17}$ is α-OH:β-C(=Z)—(CH$_2$)$_n$—NR$_{21}$R$_{210}$, and (IV) $R_5$ is α-$R_{57}$:β-$R_{58}$, only when $R_{17}$ is α-$R_{175}$:β-$R_{176}$ or α-OH:β-C—(=Z)—(CH$_2$)$_n$—NR$_{21}$R$_{210}$, or the 16,17-acetonide thereof.

Preferred compounds of formula (XI) are the amino substituted steroids where:

(A-I) $R_{16}$ is α-$R_{61}$:β-$R_{62}$, $R_{10}$ is α-$R_{101}$:β-$R_{102}$ and $R_7$ is α-H:β-H, where one of $R_{61}$ and $R_{62}$ is —H, and the other is —H, —F, or $C_1$-$C_3$ alkyl, $R_{102}$ is —CH$_3$, $R_{10}$, and $R_5$ taken together are —(CH$_2$)$_2$—C(=R$_{33}$)—CH= or —CH=CH—CO—CH=, where $R_{33}$ is =O or α-H:β-OR$_{34}$ or α-OR$_{34}$:β-H, where $R_{34}$ is —H, —CO—CH$_3$, —CO—C$_2$H$_5$, —CO—C$_6$H$_5$, —CO—O—CH$_3$ or —CO—O—C$_2$H$_5$;

(A-II) $R_5$ is α-$R_{53}$:β-$R_{54}$, $R_6$ is α-$R_{63}$:β-$R_{64}$, $R_{10}$ is α-$R_{103}$:β-$R_{104}$ and $R_7$ is α-H:β-H, where one of $R_{63}$ and $R_{64}$ is —H, and the other taken together with one of $R_{53}$ and $R_{54}$ forms a second bond between $C_5$ and $C_6$, $R_{104}$ is —CH$_3$, $R_{103}$ and the other of $R_{53}$ and $R_{54}$ taken together is —(CH$_2$)$_2$—C(H)(OH)—CH$_2$—;

(A-III) $R_{10}$ and $R_5$ taken together are =CH—CH=C(OR$_3$)—CH= where $R_3$ is —H, $C_1$-$C_3$ alkyl, —CO—H, $C_2$-$C_4$ alkanoyl or benzyl, $R_6$ is α-$R_{65}$:β-$R_{66}$ where one of $R_{65}$ and $R_{66}$ is —H, and the other is —H, —F, or $C_1$-$C_3$ alkyl and $R_7$ is α-H:β-H;

(A-IV) $R_5$ is α-$R_{57}$:β-$R_{58}$, $R_6$ is α-$R_{67}$:β-$R_{68}$, $R_7$ is α-H:β-H and $R_{10}$ is α-$R_{107}$:β-$R_{108}$, where one of $R_{57}$ and $R_{58}$ is —H, $R_{107}$ and the other of $R_{57}$ and $R_{58}$ taken together are —(CH$_2$)$_2$—C(=R$_{33}$)—CH$_2$, where $R_{33}$ is as defined above, $R_{108}$ is —CH$_3$, where one of $R_{67}$ and $R_{68}$ is —H and the other is —H, —F, or $C_1$-$C_3$ alkyl;

(A-V) $R_6$ is $R_{69}$:$R_{610}$, $R_7$ is $R_{79}$:$R_{710}$, $R_{10}$ is α-$R_{109}$:$R_{1010}$, where one of $R_{69}$ and $R_{610}$ is —H and the other taken together with one of $R_{79}$ and $R_{710}$ forms a second bond between $C_6$ and $C_7$, and the other of $R_{79}$ and $R_{710}$ is —H, $R_{1010}$ is —CH$_3$, $R_{109}$ and $R_5$ taken together are —(CH$_2$)$_2$—C(=R$_{33}$)—CH= or —CH=CH—CO—CH=, where $R_{33}$ is as defined above;

where:

(C-I) $R_{11}$ is α-$R_{111}$:β-$R_{112}$, where one of $R_{111}$ and $R_{112}$ is taken together with $R_9$ to form a second bond between $C_9$ and $C_{11}$ and the other of $R_{111}$ and $R_{112}$ is —H;

(C-II) $R_9$ is —Cl and $R_{11}$ is =O or α-H:β-$R_{114}$ where $R_{114}$ is —Cl or —OH;

(C-III) $R_9$ is —H or —F and $R_{11}$ is =O or α-$R_{115}$:β-$R_{116}$, where one of $R_{115}$ and $R_{116}$ is —H, and the other of $R_{115}$ and $R_{116}$ is —H, —OH or $C_1$-$C_{12}$ alkoxy;

(C-IV) $R_9$ is —H or —F and $R_{11}$ is α-O—CO—$R_{117}$:β-H, where $R_{117}$ is
(A) $C_1$-$C_3$ alkyl,
(B) $C_1$-$C_{12}$ alkoxy,
(C) furanyl,
(D) —NR$_{122}$R$_{123}$, where one of $R_{122}$ and $R_{123}$ is —H, methyl or ethyl and the other is —H, $C_1$-$C_4$ alkyl or phenyl,
(E) —$X_3$-$X_1$, where $X_3$ is —O— or a valence bond, where $X_1$ is phenyl optionally substituted with 1 through 2 —Cl, $C_1$-$C_3$ alkoxy, —NH$_2$, $C_1$-$C_3$ alkylamino, di($C_1$-$C_3$)alkylamino, where the alkyl groups are the same or different, 1-pyrrolidinyl-, 1-piperidinyl, $C_2$-$C_4$ acylamino and —NH—CHO;

where:

(D-III) $R_{16}$ is α-$R_{165}$:β-$R_{166}$ and $R_{17}$ is α-$R_{175}$:β-$R_{176}$, where $R_{165}$ is —H, —OH, —F or —CH$_3$ and $R_{166}$ is —H, —OH, —F, or —CH$_3$, with the proviso that at least one of $R_{165}$ and $R_{166}$ is —H, where $R_{175}$ is —H, —OH, —CH$_3$, —CH$_2$CH$_3$, $C_2$-$C_7$ alkanoyloxy or —O—CO—$X_1$, where $X_1$ is as defined above, and where $R_{176}$ is —C(=Z)—(CH$_2$)$_n$—NR$_{21}$R$_{210}$, where Z is =O, =CH$_2$ or $R_{179}$:-H, where $R_{179}$ is —H or —CH$_3$, where n is 1, where (C) $R_{21}$ and $R_{210}$ are taken together with the attached nitrogen atom to form a heterocyclic ring selected from the group consisting of (6) 1-piperazinyl substituted in the 4- position with $X_2$—(CH$_2$)$_j$—, where j is 0 and where $X_2$ is:
(a) pyridin-2-, 3- or 4-yl or the N-oxide thereof optionally substituted by 1 or 2 $R_{212}$, being the same or different, where $R_{212}$ is
(iv) $C_1$-$C_3$ allyl,
(v) —CH$_2$—CH=CH$_2$,
(vi) —$X_1$, where $X_1$ is as defined above,
(vii) —NR$_{213}$R$_{213}$ where the $R_{213}$'s are or same or different and are —H, $C_1$-$C_3$ alkyl or —CH$_2$—CH=CH$_2$,
(viiiα) *CH$_2$—(CH$_2$)$_q$—CH$_2$—N*— where the atoms marked with an asterisk (*) are bonded to each other resulting in the formation of a ring, where q is 1 through 3,
(viiiβ) *CH$_2$—CH$_2$—(CH$_2$)$_c$—G—(CH$_2$)$_d$—CH$_2$—CH$_2$—N*— where the atoms marked with an asterisk (*) are bonded to each other resulting in the formation of a ring, where G is —O—, —S—, —SO—, —SO$_2$— or —NHR$_{214}$, where $R_{214}$ is —H, $C_1$-$C_3$ alkyl, or $X_1$ as defined above, where c and d are the same or different and are 0 through 2 with the proviso that the total number of ring carbon atoms is 4 or 5, [a]
(ix) 3-pyrrolin-1-yl, [b]
(x) pyrrol-1-yl optionally substituted with $C_1$-$C_3$ alkyl, [c]
(xi) piperidin-1-yl optionally substituted with 1 or 2 $C_1$-$C_3$ alkyl, [d]
(xii) 1,2,3,6-tetrahydropyridin-1-yl, [e]
(xiv) 1,4-dihydro-1-pyridinyl substituted in the 4-position by two $C_1$-$C_3$ alkyl being the same or different, [g]
(xvi) $C_1$-$C_3$ alkoxy,
(xviii) pyridin-2-, 3- or 4-yl,
(b) 1,3,5-triazin-2-yl or the N-oxide thereof optionally substituted at the 4- and/or 6- position with $R_{212}$ is as defined above, (4)
(c) pyrimidin-4-yl or the N-oxide thereof optionally substituted at the 2- and/or 6- position with $R_{212}$ is as defined above, (5)
(d) pyrimidin-2-yl optionally substituted at 4- and/or 6-position with 1 or 2 $R_{212}$ as is defined above,
(n) 1,2,4-triazol-3-yl optionally substituted at the 5- and/or 6-position with $R_{212}$ as is defined above, (14)
(7) 1-piperazinyl substituted in the 4-position with $X_1$—(CH$_2$)$_j$—, where $X_1$ and j are as defined above, [F]
(8) 4-hydroxy-1-piperidinyl substituted in the 4-position with $X_1$ as defined above, [G]

and pharmaceutically acceptable salts thereof,
and hydrates and solvates thereof.

More preferred compounds of formula (XI) are the amino substituted steroids where:

(A-I) $R_6$ is $\alpha\text{-}R_{61}{:}\beta\text{-}R_{62}$, $R_{10}$ is $\alpha\text{-}R_{101}{:}\beta\text{-}R_{102}$ and $R_7$ is $\alpha\text{-H}{:}\beta\text{H}$, where one of $R_{61}$ and $R_{62}$ is —H, and the other is —H, —F, or $C_1$–$C_3$ alkyl, $R_{102}$ is —$CH_3$, $R_{101}$ and $R_5$ taken together are —$(CH_2)_2$—$C(=R_{33})$—$CH=$ or —$CH=CH$—$CO$—$CH=$, where $R_{33}$ is $=O$;

where:

(C-I) $R_{11}$ is $\alpha\text{-}R_{111}{:}\beta\text{-}R_{112}$, where one of $R_{111}$ and $R_{112}$ is taken together with $R_9$ to form a second bond between $C_9$ and $C_{11}$ and the other of $R_{111}$ and $R_{112}$ is —H;

(C-III) $R_9$ is —H and $R_{11}$ is $\alpha\text{-}R_{115}{:}\beta\text{-}R_{116}$, where both $R_{115}$ and $R_{116}$ are —H;

where:

(D-III) $R_{16}$ is $\alpha\text{-}R_{165}{:}\beta\text{-}R_{166}$ and $R_{17}$ is $\alpha\text{-}R_{175}{:}\beta\text{-}R_{176}$, where $R_{165}$ is —H, —OH, —F or —$CH_3$ and $R_{166}$ is —H, —OH, —F, or —$CH_3$, with the proviso that at least one of $R_{165}$ and $R_{166}$ is —H, where $R_{175}$ is —H, —OH, —$CH_3$, —$CH_2CH_3$, $C_2$–$C_7$ alkanoyloxy or —O—CO—$X_1$, where $X_1$ is as defined above, and where $R_{176}$ is —$C(=Z)$—$(CH_2)_n$—$NR_{21}R_{210}$, when Z is $=O$, $=CH_2$ or $R_{179}{:}$—H, where $R_{179}$ is —H or —$CH_3$, where n is 1, where (C) $R_{21}$ and $R_{210}$ are taken together with the attached nitrogen atom to form a heterocyclic ring selected from the group consisting of (6) 1-piperazinyl substituted in the 4- position with $X_2$—$(CH_2)_j$—, where j is 0 and where $X_2$ is:

(a) pyridin-2-, 3- or 4-yl or the N-oxide thereof optionally substituted by 1 or 2 $R_{212}$, being the same or different, where $R_{212}$ is (iv) $C_1$–$C_3$ alkyl, (v) —$CH_2$—$CH=CH_2$, (vi) —$X_1$, where $X_1$ is as defined above, (vii) —$NR_{213}R_{213}$ where the $R_{213}$'s are the same or different and are —H, $C_1$–$C_3$ alkyl or —$CH_2$—$CH=CH_2$, (viii$\alpha$) *$CH_2$—$(CH_2)_q$—$CH_2$—N*— where the atoms marked with an asterisk (*) are bonded to each other resulting in the formation of a ring, where q is 1 through 3, (viii$\beta$) *$CH_2$—$CH_2$—$(CH_2)_c$—G—$(CH_2)_d$—$CH_2$—N*— where the atoms marked with an asterisk (*) are bonded to each other resulting in the formation of a ring, where G is —O—, —S—, —SO—, —$SO_2$— or —$NHR_{214}$, where $R_{214}$ is —H, $C_1$–$C_3$ alkyl, or $X_1$ as defined above, where c and d are the same or different and are 0 through 2 with the proviso that the total number of ring carbon atoms is 4 or 5, [a]

(ix) 3-pyrrolin-1-yl, [b]

(x) pyrrol-1-yl optionally substituted with $C_1$–$C_3$ alkyl, [c]

(xi) piperidin-1-yl optionally substituted with 1 or 2 $C_1$–$C_3$ alkyl, [d]

(xii) 1,2,3,6-tetrahydropyridin-1-yl, [e]

(xiv) 1,4-dihydro-1-pyridinyl substituted in the 4-position by two $C_1$–$C_3$ alkyl being the same or different, [g]

(xvi) $C_1$–$C_3$ alkoxy, (xviii) pyridin-2-, 3- or 4-yl, (b) 1,3,5-triazin-2-yl or the N-oxide thereof optionally substituted at the 4- and/or 6- position with $R_{212}$ is as defined above, (4)

(c) pyrimidin-4-yl or the N-oxide thereof optionally substituted at the 2- and/or 6- position with $R_{212}$ is as defined above, (5)

(d) pyrimidin-2-yl optionally substituted at 4- and/or 6-position with 1 or 2 $R_{212}$ as is defined above, (6)

(n) 1,2,4-triazol-3-yl optionally substituted at the 5- and/or 6-position with $R_{212}$ as is defined above, (14)

(7) 1-piperazinyl substituted in the 4- position with $X_1$—$(CH_2)_j$—, where $X_1$ and j are as defined above, [F]

(8) 4-hydroxy-1-piperidinyl substituted in the 4-position with $X_1$ as defined above, [G]

and pharmaceutically acceptable salts thereof, and hydrates and solvates thereof Also disclosed is the amino steroid of formula (Ia and Ib) where: $R_6$ is $\alpha\text{-}R_{61}{:}\beta\text{-}R_{62}$ and $R_{10}$ is $\alpha\text{-}R_{101}{:}\beta\text{-}R_{102}$, where one of $R_{61}$ and $R_{62}$ is —H, and the other is —H, —F or $C_1$–$C_3$ alkyl, $R_{102}$ is —$CH_3$, $R_{101}$ and $R_5$ taken together are —$(CH_2)_2$—$C(=R_{33})$—$CH=$ or —$CH=CH$—$CO$—$CH=$, where $R_{33}$ is $=O$ or $\alpha\text{-H}{:}\beta\text{-OR}_{34}$ or $\alpha\text{-OR}_{34}{:}\beta\text{-H}$, where $R_{34}$ is —H, —$CO$—$CH_3$, —$CO$—$C_2H_5$, —$CO$—$C_6H_5$, —$CO$—O—$CH_3$ or —$CO$—O—$C_2H_5$ or $R_5$ is $\alpha\text{-}R_{53}{:}\beta\text{-}R_{54}$, $R_6$ is $\alpha\text{-}R_{63}{:}\beta\text{-}R_{64}$ and $R_{10}$ is $\alpha\text{-}R_{103}{:}\beta\text{-}R_{104}$ where one of $R_{63}$ and $R_{64}$ is —H, and the other taken together with one of $R_{53}$ and $R_{54}$ forms a second bond between $C_5$ and $C_6$, $R_{104}$ is —$CH_3$, $R_{103}$ and the other of $R_{53}$ and $R_{54}$ taken together is —$(CH_2)_2$—$C(H)(OH)$—$CH_2$—, $R_7$ is $\alpha\text{-H}{:}\beta\text{-H}$ and $R_{16}$ is $\alpha\text{-}R_{165}{:}\beta\text{-}R_{166}$ and $R_{17}$ is $\alpha\text{-}R_{175}{:}\beta\text{-}R_{176}$, where $R_{165}$ is —H, —OH, —F or —CH, and $R_{166}$ is —H, —OH, —F, or —$CH_3$, with the proviso that at least one of $R_{165}$ and $R_{166}$ must be —H, where $R_{175}$ is —H, —OH, —$CH_3$, —$CH_2CH_3$, $C_2$–$C_7$ alkanoyloxy or —O—CO—$X_1$, and where $R_{176}$ is —$C(=Z)$—$(CH_2)_n$—$NR_{21}R_{210}$; where ... is a single or double bond and __ indicates that there are 2 possible orientations for the attached group, (1) $\alpha$ or $\beta$ when attached to the steroid ring and (2) cis or trans when attached to a carbon atom of a double bond.

Disclosed are the amino steroids of EXAMPLES 1, 4–8, 10–25, 27, 28, 30–43, 45–57, 59–70, 72–91, 94–98, 104–108, 111, 112, 114–124, 126–128, 132, 133, and 137–141.

It is preferred that the amino substituted steroid (XI) be 16$\alpha$-methyl-21-[4-[2,6-bis(1-pyrrolidinyl)-4-pyrimidinyl]-1-piperazinyl]pregna-1,4,9(11)-triene-3,20-dione, 21-[4-[3,6-bis(diethylamino)-2-pyridinyl]-1-piperazinyl]-16$\alpha$-methylpregna-1,4,9(11)-triene-3,20-dione and 21-[4-[6-(ethylamino)-2-pyridinyl]piperazinyl]-16$\alpha$-methylpregna-1,4,9(11)-triene-3,20-dione.

The preferred amino substituted steroid (XI) is 16$\alpha$-methyl-21-[4[2,6-bis(1-pyrrolidinyl)-4-pyrimidinyl]-1-piperazinyl]pregna-1,4,9(11)-triene-3,20-dione. More preferred is 16$\alpha$-methyl-21-[4-[2,6-bis(1-pyrrolidinyl)-4-pyrimidinyl]-1-piperazinyl]pregna 1,4,9(11)-triene-3,20-dione monomethanesulfonate, 16$\alpha$-methyl-21-[4-[2,6-bis(1-pyrrolidinyl)-4-pyrimidinyl]-1-piperazinyl]pregna1,4,9(11)-triene-3,20-dione bismethanesulfonate and 16$\alpha$-methyl-21-[4-[2,6-bis(1-pyrrolidinyl)-4-pyrimidinyl]-1-piperazinyl]pregna-1,4,9(11)-triene-3,20-dione hydrochloride. Most preferred is 16$\alpha$-methyl-21-[4-[2,6-bis(1-pyrrolidinyl)-4-pyrimidinyl]-1-piperazinyl]pregna-1,4,9(11)-triene-3,20-dione monomethanesulfonate.

Further disclosed is an aromatic amino steroid of formula (II) where: $R_{10}$ and $R_5$ taken together are $=CH$—$CH=C(OR_3)$—$CH=$ where $R_3$ is —H, $C_1$–$C_3$ alkyl, —CO—H, $C_2$–$C_4$ alkanoyl or benzyl, $R_6$ is $\alpha\text{-}R_{65}{:}\beta\text{-}R_{66}$ where one of $R_{65}$ and $R_{66}$ is —H, and the other is —H, —F or $C_1$–$C_3$ alkyl, $R_7$ is $\alpha\text{-H}{:}\beta\text{-H}$ and $R_{16}$ is $\alpha\text{-}R_{165}{:}\beta\text{-}R_{166}$ and $R_{17}$ is $\alpha\text{-}R_{175}{:}\beta\text{-}R_{176}$, where $R_{165}$ is —H, —OH, —F or —$CH_3$ and $R_{166}$ is —H, —OH, —F, —$CH_3$, with the proviso that at least one of $R_{165}$ and $R_{166}$ must be —H, where $R_{175}$ is —H, —OH, —CH$_3$, —CH$_2$CH$_3$, C$_2$–C$_7$ alkanoyloxy or —O—CO—X$_1$, and where $R_{176}$ is —C(=Z)—(CH$_2$)$_n$—NR$_{21}$R$_{210}$. Disclosed aromatic amino steroids of formula (H) are the compounds of EXAMPLES 125 and 129.

Additionally disclosed is $\Delta^{16}$ amino steroid of formula (IIIa and IIIb) where: $R_6$ is -R$_{61}$:β-R$_{62}$ and $R_{10}$ is α-R$_{101}$:β-R$_{102}$, where one of $R_{61}$ or $R_{62}$ is —H, and the other is —H, —OH, —F, C$_1$–C$_3$ alkyl or phenyl, $R_{102}$ is —CH$_3$, $R_{101}$ and $R_5$ taken together are —(CH$_2$)$_2$—C(=R$_{33}$)—CH= or —CH=CH—CO—CH=, where $R_{33}$ is =O or α-H:β-OR$_{34}$ or α-OR$_{34}$:β-H, where $R_{34}$ is —H, —CO—CH$_3$, —CO—C$_2$H$_5$, —CO—C$_6$H$_5$, —CO—O—CH$_3$ or —CO—O—C$_2$H$_5$ or $R_5$ is α-R$_{53}$:β-R$_{54}$, $R_6$ is α-R$_{63}$:β-R$_{64}$ and $R_{10}$ is α-R$_{103}$:β-R$_{104}$ where one of $R_{63}$ and $R_{64}$ is —H, and the other taken together with one of $R_{53}$ and $R_{54}$ forms a second bond between C$_5$ and C$_6$, $R_{104}$ is —CH$_3$, $R_{103}$ and the other of $R_{53}$ and $R_{54}$ taken together is —(CH$_2$)$_2$—C(H)(OH)—CH$_2$—, $R_7$ is α-H:β-H and $R_{16}$ is R$_{161}$:R$_{162}$ and $R_{17}$ is R$_{171}$:R$_{172}$, where one of $R_{161}$ and $R_{162}$ is —H or —CH$_3$ and the other taken together with one of $R_{171}$ and $R_{172}$ forms a second bond between C$_{16}$ and C$_{17}$, and the other of $R_{171}$ and $R_{172}$ is —C(=Z)—(CH$_2$)$_n$— NR$_{21}$R$_{210}$; where ⋯is a single or double bond and where _ indicates that there are 2 possible orientations for the attached group, (1) α or β when attached to the steroid ring and (2) cis or trans when attached to a carbon atom of a double bond. Disclosed $\Delta^{16}$ amino steroids of formula (III) are the compounds of EXAMPLES 58 and 113.

Also disclosed is a reduced A-ring amino steroid of formula (IV) where: $R_5$ is α-$_{57}$:β-R$_{58}$, $R_6$ is α-R$_{67}$:β-R$_{68}$ and $R_{10}$ is α-R$_{107}$:β-R$_{108}$, where one of $R_{57}$ and $R_{58}$ is —H, $R_{107}$ and the other of $R_{57}$ and $R_{58}$ taken together are —(CH$_2$)$_2$—C(R$_{33}$)—CH$_2$, where $R_{33}$ is =O or α-H:β-OR$_{34}$ or α-OR$_{34}$:β-H, where $R_{34}$ is —H, —CO—CH$_3$, —C$_2$H$_5$, —CO—C$_6$H$_5$, —CO— O—CH$_3$ or —CO—O—C$_2$H$_5$, $R_{108}$ is —CH$_3$, where one of $R_{67}$ and $R_{68}$ is —H and the other is —H, —F or C$_1$–C$_3$ alkyl, $R_7$ is α-H:β-H and $R_{16}$ is α-$_{165}$:β-R$_{166}$ and $R_{17}$ is α-R$_{175}$:β-R$_{176}$, where R$_{165}$ is —H, —OH, —F or —CH$_3$ and R$_{166}$ is —H, —OH, —F or —CH$_3$, with the proviso that at least one of $R_{165}$ and $R_{166}$ must be —H, where $R_{175}$ is —H, —OH, —CH$_3$, —CH$_2$CH$_3$, C$_2$–C$_7$ alkanoyloxy or —O—CO—X$_1$, and where $R_{176}$ is —C(=Z)—(CH$_2$)$_n$—NR$_{21}$R$_{210}$; where ⋯is a single or double bond and where _ indicates that there are 2 possible orientations for the attached group, (1) α or β when attached to the steroid ring and (2) cis or trans when attached to a carbon atom of a double bond. Disclosed reduced ring amino steroids of formula (IV) are the compounds of EXAMPLES 44, 99, 130, 131, and 136.

Further disclosed is a $\Delta^{17}$ amino steroid of formula (Va and Vb) where: $R_6$ is α-R$_{61}$:β-R$_{62}$ and $R_{10}$ is α-R$_{101}$:β-R$_{102}$, where one of $R_{61}$ or $R_{62}$ is —H, and the other is —H, —F or C$_1$–C$_3$ alkyl, $R_{102}$ is —CH$_3$, $R_{101}$ and $R_5$ taken together are —(CH$_2$)$_n$—C(= R$_{33}$)—CH= or —CH=CH—CO—CH=, where $R_{33}$ is =O or α-H:β-OR$_{34}$ or α-OR$_{34}$:β-H, where $R_{34}$ is —H, —CO—CH$_3$, —CO—C$_2$H$_5$, —CO—C$_6$H$_5$, —CO—O—CH$_3$ or —CO—O—C$_2$H$_5$ or $R_5$ is α-R$_{53}$:β-R$_{54}$, $R_6$ is α-R$_{63}$:β-R$_{64}$ and $R_{10}$ is α-R$_{103}$:β-R$_{104}$ where one of $R_{63}$ and $R_{64}$ is —H, and the other taken together with one of $R_{53}$ and $R_{54}$ forms a second bond between C$_5$ and C$_6$, $R_{104}$ is —CH$_3$, $R_{103}$ and the other of $R_{53}$ and $R_{54}$ taken together is —(CH$_2$)$_2$—C(H)(OH)—CH$_2$—, $R_7$ is α-H:β-H and $R_{16}$ is αR$_{162}$:β-R$_{164}$ where one of $R_{163}$ and $R_{164}$ is —H and the other is —H, —OH, —F or —CH$_3$, and $R_{17}$ is =CH—(CH$_2$)$_p$—NR$_{21}$R$_{210}$, where p is 1 or 2, where ⋯is a single or double bond and where _ indicates that there are 2 possible orientations for the attached group, (1) α or β when attached to the steroid ring and (2) cis or trans when attached to a carbon atom of a double bond.

Disclosed are $\Delta^{9(11)}$-steroids of formula (VI) where: (A-I) $E_6$ is α-E$_{61}$:β-E$_{62}$ and $E_{10}$ is α-E$_{101}$:β-E$_{102}$, where one of $E_{61}$ and $E_{62}$ is —H, and the other is —H, —F, —Cl, —Br or C$_1$–C$_3$ alkyl, E$_{101}$ and $E_5$ taken together are —(CH$_2$)$_2$—C(=E$_{33}$)—CH= or —CH=CH—CO—CH=, where $E_{33}$ is =O or α-H:β-OE$_{34}$ or α-OE$_{34}$:β-H, where $E_{34}$ is —H, —CO—CH$_3$, —CO—C$_2$H$_5$, —CO— C$_6$H$_5$, —CO—O—CH$_3$ or —CO—O—C$_2$H$_5$, where $E_{102}$ is —CH$_3$;

(A-II) $E_5$ is α-E$_{53}$:β-E$_{54}$, $E_6$ is α-E$_{63}$:β-E$_{64}$ and $E_{10}$ is α-E$_{103}$:β-E$_{104}$, where one of E$_{63}$ and E$_{64}$ is —H, and the other taken together with one of $E_{53}$ and $E_{54}$ forms a second bond between C$_5$ and C$_6$, $E_{104}$ is —CH$_3$, $E_{103}$ and the other of $E_{53}$ and $E_{54}$ taken together are —(CH$_2$)$_2$—C(H)(OH)—CH$_2$—;

(A-IV) $E_5$ is α-E$_{57}$:β-E$_{58}$, $E_6$ is α-E$_{67}$:β-E$_{68}$ and $E_{10}$ is αE$_{107}$:β -E$_{108}$, where one of $E_{57}$ and $E_{58}$ is —H, $E_{107}$ and the other of $E_{57}$ and $E_{58}$ taken together are —(CH$_2$)$_2$—C(=E$_{33}$)—CH$_2$, where $E_{33}$ is as defined above, $E_{108}$ is —CH$_3$, where one of $E_{67}$ and $E_{68}$ is —H and the other is —H, —F or C$_1$–C$_3$ alkyl;

where:

(D-I) $E_{16}$ is α-E$_{161}$:β-E$_{162}$, where one of $E_{161}$ and $E_{162}$ is —H and the other is —H, —F, —CH$_3$ or —OH;

(D-II) $E_{17}$ is —H, —CH$_3$, —CH$_2$H$_5$, —OH or —O—CO—E$_{171}$, where E$_{171}$ is C$_1$–C$_6$ alkyl or X$_1$, where X$_1$ is phenyl optionally substituted with 1 through 2 —Cl, —Br, C$_1$–C$_3$ alkoxy, —COOH, —NH$_2$, C$_1$–C$_3$ alkylamino, di(C$_1$–C$_3$)alkylamino, where the alkyl groups are the same or different, 1-pyrrolidinyl-, 1-piperidinyl, 1-hexamethyleneimino-, 1-heptamethyleneimino-, C$_2$–C$_4$ acylamino and —NH—CHO or with 1 —F or —CF$_3$;

(D-III) Z is =O, =CH$_2$, E$_{20}$:-H where $E_{20}$ is —H or —CH$_3$;

(D-IV) J is
1-(4-methyl)-piperazinyl, [J-1]
1-(4-acetyl)-piperazinyl, [J-2]
1-(4-hydroxy)-piperidinyl [J-3]
1-piperidinyl optionally substituted with 2-hydroxyethyl, [J-4]
4-morpholino [J-5]

and the 16,17-acetonide thereof when $E_{161}$ and $E_{17}$ are both —OH; and pharmaceutically acceptable salts thereof, and hydrates and solvates thereof Disclosed $\Delta^{9(11)}$-steroids of formula (VI) are the compounds of EXAMPLES 93, 100 and 101.

Also disclosed are the amines of PREPARATIONS A-1, A-3, A-9 thru A-11, A-13, A-15 thru A-24, A-26, A-28, A-29, A-34, A-40, A-42, and A-44 thru A-50. The preferred amines are A-22, A-23, A-26, A-45 thru A-47 and A-49. Most preferred is A-22, A-47 and A-49.

Further disclosed are the steroids of PREPARATIONS S-10, S-16, S-22 thru S-24, S-28, S-29, S-31 thru S-35, S-41 and S-42. More preferred is the steroids S-22 and S-24.

Disclosed are the p-fluoro amino substituted steroids of EXAMPLES 26 and 29.

Disclosed are the amino substituted steroids of EXAMPLES 142–147.

Disclosed are the amines of PREPARATIONS A-58 thru A-61.

DETAILED DESCRIPTION OF THE INVENTION

The invention is amino substituted steroids (XI), namely the amino steroids (Ia and Ib), aromatic steroids (II), $\Delta^{16}$- steroids (IIIa and IIIb), reduced A/B-ring steroids (IV) and $\Delta^{17(20)}$-steroids (Va and Vb) as well as the $\Delta^{9(11)}$-steroids (VI). Also included are the novel amine and steroidal reactants used to prepare the amino substituted steroids (XI), see PREPARATIONS "A" (amines) and "S" (steroids) respectively.

With the aromatic steroids (II) the A-ring functionality at $C_3$ is a hydroxy group or substituted hydroxy group (ether or ester). However, with the amino steroids (Ia and Ib), $\Delta^{16}$-steroids (IIIa and IIIb), reduced A/B-ring steroids (IV), $\Delta^{17(20)}$-steroids (Va and Vb) and $\Delta^{9(11)}$-steroids (VI) the A-ring functionality at $C_3$ is either hydroxyl or ketone. When the A-ring functionality at $C_3$ is hydroxy, the hydroxyl group can be in either the $\alpha$ or $\beta$ configuration. When the A-ring functionality at $C_3$ is hydroxy, there will be either a reduced A/B-ring, $\Delta^4$ or $\Delta^5$ double bond present but no double bond at $C_1$ for the steroids of formulas (Ia, Ib, IIIa, IIIb, Va, Vb and VI). When the A-ring functionality at $C_3$ is a ketone, then there will be a reduced A/B-ring or a $\Delta^4$ double bond present and no $\Delta^5$ double bond or there will be a $\Delta^{1,4}$-4-diene A-ring functionality. The reduced A/B-ring steroids of formula (IV) have no double bond in either rings A or B and have at $C_3$ either a hydroxyl group or a ketone.

The amino substituted steroids (XI) and $\Delta^{9(11)}$-steroids (VI) of the present invention are prepared by methods known to those skilled in the art from steroidal and amine reactants which are either known to those skilled in the art or which are readily prepared from compounds known to those skilled in the art by methods known to those skilled in the art.

When n is 0, the amino substituted steroids (XI) are amides and are produced in a preferred process by starting with the acid (—COOH at $C_{17}$) and reacting it first with a condensing reagent such as carbonyldiimidazole or DCC in the presence of HOBT, followed by reaction with the free amine corresponding to the desired amine substituent as is known to those skilled in the art, see for example U.S. Pat. No. 4,438,130; see also EXAMPLES 56, 57 AND 103. The amine starting materials are either known to those skilled in the art or are readily prepared from compounds known to those skilled in the art by methods known to those skilled in the art. Suitable solvents include, acetonitrile, DMF, dioxane, THF, methylene chloride, and mixtures thereof.

When n is 1 through 6, the amino substituted steroids (XI) and the $\Delta^{9(11)}$-steroids (VI) are produced in a preferred process by reacting a steroid corresponding to the desired amino steroid (Ia and Ib), aromatic steroid (II), $\Delta^{16}$-steroid (IIIa and IIIb), reduced A/B-ring steroid (IV), $\Delta^{17(20)}$-steroid (Va and Vb) and the $\Delta^{9(11)}$-steroid (VI) but having a substituent at the terminal carbon atom, at $C_{21}$ (n=1) through $C_{26}$ (n=6), such as a halogen atom (chlorine, bromine or iodine), a mesyl or tosyl group, with the desired amine in an aprotic solvent (DMF, THF, methylene chloride, acetonitrile, DMA, ether) containing a base (carbonate, bicarbonate, triethylamine, diisopropylethylamine) as is known to those skilled in the art for the formation of amines. When n is 1, the $C_{21}$-halo, mesyl or tosyl substituted steroids are known to those skilled in the art or are readily prepared from compounds known to those skilled in the art by methods known to those skilled in the art. It is preferred that the halo substituent be a bromine atom but an iodine or chlorine atom is suitable. When n is 2 through 6, the halo, mesyl or tosyl substituted steroid is prepared by reacting the corresponding 17β-carboxylate ester, of the desired steroid, with an organometallic reagent of the formula $Li(CH_2)_n$—OR to form an intermediate with the desired $C_{17}$ carbon side-chain length, followed by displacement of "OR" with the desired leaving group, see PREPARATION S-42.

The derivatives of the 3($\alpha$/$\beta$)-hydroxy steroids are prepared by methods known to those skilled in the art when the 3-hydroxy steroid starting materials contain other free hydroxy or amino functionality these groups must be protected as is known to those skilled in the art. The free hydroxy groups are protected, for example, as the THP derivatives and the free amino groups are protected, for example, as the t-butyloxycarbonyl derivatives. The 3-O-acyl derivatives (steroid-O—COR) are prepared by first dissolving the 3-hydroxy compound in a solvent such as pyridine or methylene chloride and with a base such as triethylamine present. The mixture is cooled in an ice bath and treated with the acylating agent such as acetyl chloride, acetic anhydride, propionyl chloride, benzoyl chloride, etc. The reaction mixture is then partitioned between an organic solvent such as methylene chloride and aqueous bicarbonate. The organic phase is separated, dried, concentrated and purified, for example by chromatography. Likewise, 3-carbonates are produced by reacting the 3-hydroxy steroid with a reagent such as RO—CO—Cl.

The $\Delta^{4,6}$ and $\Delta^{1,4,6}$ derivatives are prepared by reacting the corresponding $\Delta^4$ starting material with a reagent such as chloranil following the general procedure of Campbell and Babcock, J. Am. Chem. Soc. 81, 4069 (1959). If a $\Delta^{1,4,6}$ derivative is desired, the $\Delta^1$ double bond is subsequently added by methods well known to those skilled in the art such as by fermentation or with DDQ.

When the substituent at $C_{17\alpha}$ is a methyl or ethyl group and the substituents at $C_{16}$ are hydrogen atoms, the compounds are prepared by first treating the corresponding $\Delta^{16}$-steroid with lithium in liquid ammonia and then trapping the enolate with methyl or ethyl iodide. During this methylation the A-ring must be protected as is known to those skilled in the art. When the substituent at $C_{16\alpha}$ is a methyl group and at $C_{16\beta}$ is a —H, the compounds are prepared by first adding methyl magnesium chloride in the presence of a copper propionate and trapping the enolate with methyl or ethyl iodide.

Alternatively, in principle, a form of the steroid not necessarily desired as the final product (XI), can be reacted in its $C_{terminal}$ form, for example when n is 1, 21-halo, 21-mesyl or 21-tosyl form with the appropriate amine to form a 21-amino steroid. Following this, the steroid nucleus itself can be modified. While this is an alternative process, in principle, to produce the amino substituted steroids (XI), of the present invention, in practice it is an undesirable method compared to the preferred process of reacting the $C_{terminal}$ halo, tosyl or mesyl analog corresponding to the steroidal portion of desired amino substituted steroids (XI), with the amine corresponding to the amine portion of the desired amino substituted steroids (XI) as is apparent to one skilled in the art—with the exception of the esters of the 11α-hydroxy steroids, see EXAMPLES 28, 31 AND 32.

Yet another alternative procedure, in principle, to produce some of the steroids of the invention involving amino substituents which can be thought of as having 2 or more components, can be produced by first reacting the 21-halo, tosyl or mesyl steroid with a portion of the desired amine substituent to form a steroid in which there is an amine substituent at the 21-position followed by further reaction of the amino portion of the amino substituted steroid to produce the complete substituent at the 21-position. For some steroids of this invention (EXAMPLES 9 and 10) this method is preferable, but as stated above for the other alternative procedure, while this is an alternative process in principle, in practice it is usually undesirable compared to the preferred process.

For the amino substituted steroids (XI), it is preferred that the steroid be the amino steroid (Ia and Ib), more preferably the amino steroid (Ia). It is preferred that the A-ring be $\Delta^4$-3-keto or $\Delta^{1,4}$-3-keto. At $C_6$, it is preferred that $R_{61}$, $R_{65}$ and $R_{67}$ be —H and $R_{62}$, $R_{66}$ and $R_{68}$ be —H or —$CH_3$. It is preferred that $R_7$ be $\alpha$-H:$\beta$-H. For the C-ring it is preferred that $R_9$ be —H or the C-ring be $\Delta^{9(11)}$, more preferably $\Delta^{9(11)}$. It is preferred that the substituent(s) at $C_{16}$ be —H if there is only one substituent, or if two substituents, either two —H's or a —H and a —$CH_3$. If —$CH_3$ it is preferred that it be in the $\alpha$ configuration. It is preferred that $R_{175}$ be a —H, —OH, $C_2$-$C_7$ alkanoyloxy or —O—CO—$X_1$; it is more preferred that $R_{175}$ be —H. With regard to the side chain at $C_{17}$, it is preferred that it be —C(=Z)—$(CH_2)_n NR_{21}R_{210}$. It is preferred that Z be =O. It is preferred that n be 1. Regarding $R_{21}$ and $R_{210}$ it is preferred that $R_{21}$ and $R_{210}$ are taken together with the attached nitrogen atom to form a cyclic amino substituent selected from 1-piperazinyl substituted in the 4- position with $X_2$—$(CH_2)_j$— [E] and 1-piperazinyl substituted in the 4-position with $X_1$—$(CH_2)_j$— [F]. It is preferred that j be 0. With the substituent [E] it is preferred that $X_2$ be selected from the group consisting of 1,3,5-triazin-2-yl substituted in the 4- and/or 6- position with 2-pyridinyl, pyrimidin-4-yl substituted in the 2- and/or 6- position with 1-pyrrolidinyl, pyrimidin-4-yl substituted in the 2- and/or 6- position with 4-morpholino, 1,3,5-triazin-2-yl substituted in the 4- and 6- position with 1-pyrrolidinyl and pyridinyl substituted in the 3- position with —$NR_{213}R_{213}$ where one of $R_{213}$ is —H and the other is $C_2$ alkyl. It is preferred that the compounds not be the N-oxide. With the substituent [F], it is preferred that $X_1$ be phenyl optionally substituted with 1,2 or 3 methoxy groups.

It is preferred that the amino substituted steroid (XI) be selected from the group consisting of 17$\alpha$-hydroxy-21-[4-(2-pyridinyl)-1-piperazinyl]pregna-4,9(11)diene-3,20-dione, 21-[4-[2-amino-6-(diethylamino)-4-pyrimidinyl]-1-piperazinyl]-17$\alpha$-hydroxypregna- 4,9(11)-dione-3,20-dione, 17$\alpha$-hydroxy-21-[4-[2,6-bis(diethylamino)-4-pyrimidinyl]-1-piperazinyl]pregna-4,9 (11)-diene-3,20-dione, 21-[4-[2,6-bis(diethylamino)-4-pyrimidinyl]-1-piperazinyl]-17$\alpha$-hydroxy-16$\alpha$ -methylpregna-1,4,9(11)-triene-3,20-dione, 21-[4-(2-pyridinyl)-1-piperazinyl]pregna-1,4-diene-3,20-dione, 21-[4-[2,6-bis(diethylamino)-4-pyrimidinyl]-1-piperazinyl]-11$\alpha$,17$\alpha$-dihydroxypregn- 4-ene-3,20-dione, 17$\alpha$-hydroxy-16$\alpha$-methyl-21-[4-[2,6-bis(1-pyrrolidinyl)-4-pyrimidinyl]- 1-piperazinyl]pregna-1,4,9(11)-triene-3,20-dione, 17$\alpha$-hydroxy-21-[4-[2,6-bis(1-pyrrolidinyl)-4-pyrimidinyl]-1-piperazinyl]pregna- 1,4,9(11)-triene-3,20-dione, 16$\alpha$methyl-21-[4-[2,6-bis(1-pyrrolidinyl)-4-pyrimidinyl]-1-piperazinyl]pregna- 1,4,9(11)-triene-3,20-dione, 11$\alpha$-hydroxy-16$\alpha$-methyl-21-[4-[2,6-bis(1-pyrrolidinyl)-4-pyrimidinyl]-1 -piperazinyl]pregna-1,4-diene-3,20-dione, 16$\alpha$-methyl-21-[4-[2,6-bis(1-pyrrolidinyl)-4-pyrimidinyl]-1-piperazinyl]pregna- 1,4-diene-3,20-dione, 16$\alpha$-methyl-21-[4-[2,6-bis(4-morpholino)-4-pyrimidinyl]-1-piperazinyl]pregna- 1,4,9(11)-triene-3,20-dione, 11$\alpha$-hydroxy-16$\alpha$-methyl-21-[4-[2,6-bis(4-morpholino)-4-pyrimidinyl]- 1-piperazinyl]pregna-1,4-diene-3,20-dione, 16$\alpha$-methyl-21-[4-[2,6-bis(4-morpholino)-4-pyrimidinyl]-1-piperazinyl]pregna-1,4 -diene-3,20-dione, 21-[4-[3,6-bis(diethylamino)-2-pyridinyl]-1-piperazinyl]-16$\alpha$-methylpregna- 1,4,9(11)-triene-3,20-dione, 21-[4-[6-(ethylamino)-2-pyridinyl]piperazinyl]-16$\alpha$-methylpregna-1,4,9(11)-triene- 3,20-dione, 16$\alpha$-methyl-21-[4-[4,6-bis(2-pyridinyl)-1,3,5-triazin-2-yl]-1-piperazinyl] pregna-1,4,9(11)-triene-3,20-dione and pharmaceutically acceptable salts, hydrates and solvates thereof.

It is more preferred the amino substituted steroid (XI) be

16$\alpha$-methyl-21-[4-[2,6-bis(1-pyrrolidinyl)-4-pyrimidinyl]-1-piperazinyl] pregna-1,4,9(11)-triene-3,20-dione, 21-[4-[6-(ethylamino)-2-pyridinyl]piperazinyl]-16$\alpha$-methylpregna-1,4,9(11)-triene- 3,20-dione or 21-[4-[6-(ethylamino)-2-pyridinyl]piperazinyl)-16$\alpha$-methylpregna1,4,9(11)-triene- 3,20-dione.

The amino substituted steroids (XI) and the $\Delta^{9(11)}$steroids (VI) of the present invention are reacted with acids to form amine salts by methods known to those skilled in the art and the resulting salts are more water soluble and therefore preferable to use when an aqueous formulation is desired such as a solution for IV use. Generally the amino substituted steroids (XI) and $\Delta^{9(11)}$steroids (VI) possess one or more basic nitrogen atoms to be converted to an acid addition pharmaceutically acceptable salt. However, when n is 0 and Z is =O (i.e. amides) and the compound does not contain another nitrogen atom, they will not form salts suitable as pharmaceuticals. The pharmaceutically acceptable salt forms of the amino substituted steroids (XI and VI) are generally preferred over the free base form since the salts have greater water solubility and form crystals more suitable for pharmaceutical purposes. An acid addition salt of the amino substituted steroids (XI) and the $\Delta^{9(11)}$steroids (VI) can be converted to the free base, which can be converted to any desired pharmaceutically acceptable acid addition salt by methods known to those skilled in the art. It is preferred that the acid addition salt be prepared by reacting the free base of the amino substituted steroids (XI) and the $\Delta^{9(11)}$steroids (VI) with an approximately stoichiometric amount of an acid, such as hydrochloric, hydrobromic, hydroiodic, sulfuric, phosphoric, acetic, lactic, citric, succinic, benzoic, salicylic, pamoic, cyclohexanesulfamic, methanesulfonic, naphthalenesulfonic, p-toluenesulfonic, maleic, fumaric, oxalic acid and the like. It is preferred that the acid be selected from the group consisting of hydrochloric, maleic, methanesulfonic and fumaric adds.

The amino substituted steroids (XI) and the $\Delta^{9(11)}$steroids (VI) and acid addition salts can be isolated as hydrates or solvates, and such forms are regarded as equivalent to the corresponding amino substituted steroids (XI) and the $\Delta^{9(11)}$steroids (VI) not containing water or solvent.

The amino substituted steroids (XI) and the $\Delta^{9(11)}$steroids (VI) of the present invention are useful pharmaceutical agents in treating a number of different medical conditions in humans and useful warm blooded animals.

In humans, the amino substituted steroids (XI) and the $\Delta^{9(11)}$steroids (VI) of the present invention are useful in treating spinal trauma, mild and/or moderate to severe head injury, subarachnoid hemorrhage and subsequent cerebral vasospasm, ischemic (thromboembolic) stroke, excess mucous secretion, asthma, muscular dystrophy, adriamycin-induced cardiac toxicity, Parkinsonism, Alzheimer's disease, other degenerative neurological disorders, multiple sclerosis, organ damage during reperfusion after transplant, skin graft rejection, hemorrhagic, traumatic and septic shock, and conditions such as severe burns, ARDS, inflammatory diseases such as osteo- or rheumatoid arthritis, nephrotic syndrome (immunological), systemic lupus erythematosis, allergic reactions, atherosclerosis, inflammation (for example dermatological, inflammatory and psoriasis conditions), emphysema, stress induced ulcers, cluster headaches, complications from brain tumors, radiation damage and damage after MI, infant hypoxia syndrome and such ophthalmic disorders such as uveitis and optic neuritis. Amino substituted steroids (XI) having the amine functionality 4-[2,6-bis(4-alkyl-1-piperazinyl)-4-pyrimidinyl]-1-piperazinyl are useful in treating burn victims for burn healing, useful in promoting wound healing and for post MI heart recovery.

In humans, the amino substituted steroids (XI) and the $\Delta^{9(11)}$steroids (VI) are useful in preventing damage following cardiopulmonary resuscitation, neurological or cardiovascular surgery and from cardiac infarction.

Generally, the amino substituted steroids (XI) and the $\Delta^{9(11)}$steroids (VI) are useful in the same way as glucocorticoid pharmaceuticals for the treatment of the above human conditions as well as the animal conditions listed below. While the amino substituted steroids (XI) and the $\Delta^{9(11)}$steroids (VI) are useful in both humans and animals in treating many of the same conditions and preventing damage from the same problems as the glucocorticoids, the amino substituted steroids (XI) and the $\Delta^{9(11)}$steroids (VI) are useful in treating a number of conditions and preventing damage from conditions where the glucocorticoids are not useful. The amino substituted steroids (XI) and the $\Delta^{9(11)}$steroids (VI) have diminished glucocorticoid activity and therefore, unlike the glucocorticoids, they can be given daily for long periods of time (used chronically) without the side effects associated with the glucocorticoids. This is a distinct advantage.

It is to be understood that each of the amino substituted steroids (XI) and the $\Delta^{9(11)}$steroids (VI) is useful for a number of the above conditions but not each and every compound is useful for each and every condition. It is well within the ability of those skilled in the art to easily determine which particular amino substituted steroids (XI) and the $\Delta^{9(11)}$steroids (VI) are useful for each particular condition without undue experimentation. For example, the arachidonic acid $LD_{50}$ test of Kohler, Thrombosis Res., 9, 67 (1976), identifies compounds which are antioxidants, which inhibit lipid peroxidation, and/or which inhibit the prostaglandin cascade and are useful in treating spinal trauma, mild and/or moderate to severe head injury, degenerative neurological disorders, etc. Another method useful for determining which particular compounds inhibit lipid peroxidation and which are therefore useful in treating spinal trauma, mild and/or moderate to severe head injury, degenerative neurological disorders, etc is described by Pryor in Methods of Enzymology 105, 293 (1984). Further, the mouse head injury assay of Hail, J. Neurosurg., 62, 882 (1980) discloses an assay from which one skilled in the art can readily determine which particular amino substituted steroids (XI) and the $\Delta^{9(11)}$steroids (VI) are useful in the acute treatment of spinal trauma or mild and/or moderate to severe head injury. Additionally, the cat 48 hr motor nerve degeneration model of Hall et al, Exp. Neurol., 79, 488 (1983) discloses a routine assay from which one skilled in the art can readily determine which particular amino substituted steroids (XI) and the $\Delta^{9(11)}$steroids (VI) are useful in treating chronic degenerative neurological disorders such as Parkinsonism, Alzheimer's disease etc. H. Johnson in Int. Arch. Allergy Appl. Immunol., 70, 169 (1983) has described the ascaris sensitized rhesus monkey assay for anti-asthma drugs.

The standard conditions for treatment are to give the amino substituted steroids (XI) and the $\Delta^{9(11)}$steroids (VI) orally or parenterally, e.g. IV (that is by injection, infusion or continuous drip) or IM, with a standard dose of about 0.05 to about 100 mg/kg/day, one to four times daily.

For a number of the conditions to be treated with the amino substituted steroids (XI) and $\Delta^{9(11)}$steroids (VI) the preferred route of administration is parenteral. When certain of the amino substituted steroids (XI) are administered IV, hemolysis occurs in test animals. To prevent hemolysis it is preferred to use the following formulation: amino substituted steroid (XI) 1.5 mg/ml, citric acid-hydrate 20 mM, sodium citrate-dehydrate 3.2 mM, sodium chloride 4.5 mg/ml, pH=3.0, osmolality 183 mOsm/kg. The solution is prepared by first dissolving the amino substituted steroid (XI) in acidic media then adding the other excipients. After dilution with water to the final volume, the solution is sterilized by filtering thru a 0.22 μm cartridge or disc and filled into sterile vials. The vials are stored at 4° to maintain stability.

For treating spinal trauma, mild and moderate to severe head injury, damage following cardiopulmonary resuscitation, cardiac infarction, organ damage during reperfusion after transplant, hemorrhagic, traumatic and septic shock, severe burns, ARDS, and nephrotic syndrome and preventing skin graft rejection, the standard conditions are used. Typical treatment will involve an initial loading dose, e.g. an IV dose of 0.01 mg to 1 mg/kg followed by maintenance dosing e.g. IV infusion for a day to a week depending on the particular condition of the patient and the particular compound used. This may be supplemented with IM or oral dosing for days, weeks or months to prevent delayed neuronal degeneration in neurological applications (eg spinal trauma, head injury).

In treating subarachnoid hemorrhage and subsequent cerebral vasospasm or ischemic (thromboembolic) stroke the standard conditions are used and patients at risk are pre-treated orally.

In treating excess mucous secretion and asthma the amino substituted steroids (XI) and the $\Delta^{9(11)}$steroids (VI) are administered orally, IV and by inhalation in the standard dose. In treating excess mucous secretions the dose of the amino substituted steroids (XI) and the $\Delta^{9(11)}$steroids (VI) used is from about 0.05 to about 100 mg/kg/day. The frequency of administration is one through 4 times daily. The oral administration of the amino substituted steroids (XI) all the $\Delta^{9(11)}$steroids (VI) to treat excess mucous secretions may go on for months or even years. The susceptible individuals can be pre-treated a few hours before an expected problem. The IV dose is about 0.05 to about 50 mg/kg/day. The aerosol formulation contains about 0.05 to about 1.0% of the amino substituted steroids (XI) and the $\Delta^{9(11)}$steroids (VI) and is administered or used about four times daily as needed.

In treating muscular dystrophy, Parkinsonism, Alzheimer's disease and other degenerative neurological disorders (amyotrophic lateral sclerosis; multiple sclerosis) the amino substituted steroids (XI) and the $\Delta^{9(11)}$steroids (VI) are administered orally using a dose of about 0.05 to about 100 mg/kg/day, administered or used one to four times a day. The treatment may go on for years.

In addition, utility in disorders or physiological phenomena dependent on angiogenesis or neovascularization such as embryo implantation (antifertility), arthritis, and atherosclerosis is exhibited with the amino substituted steroids (XI) and the $\Delta^{9(11)}$steroids (VI) with or without co-administered oral heparin or systemic heparin fragments, see Science 221, 719 (1983).

In treating adriamycin-induced cardiac toxicity the amino substituted steroids (XI) and the $\Delta^{9(11)}$steroids (VI) are administered orally or IV using a dose of about 0.05 to about 100 mg/kg/day (orally) or (IV). The amino substituted steroids (XI) and the $\Delta^{9(11)}$steroids (VI) are preferably given concomitantly with IV adriamycin or the individual is pretreated with the amino substituted steroids (XI) and the $\Delta^{9(11)}$steroids (VI).

For prophylaxis prior to and preventing damage after neurological or cardiovascular surgery the amino substituted steroids (XI) and the $\Delta^{9(11)}$steroids (VI) are used according to the standard conditions. The patient can be pretreated with a single IV or IM dose just prior to surgery or orally before and after surgery.

In treating osteo- or rheumatoid arthritis and other inflammatory diseases the amino substituted steroids (XI) and the $\Delta^{9(11)}$steroids (VI) are given orally or IM in doses of about 0.05 to about 100 mg/kg/day, one to four times daily. Orally the drug will be given over a period of months or years alone or with other steroidal agents. The initial dose with some severe rheumatoid patients may be given IV and followed with an IV drip for up to 24 hr or more. In addition, intra-articular administration may be employed.

In treating drug allergic reactions the amino substituted steroids (XI) and the $\Delta^{9(11)}$steroids (VI) are given orally or IV in a dose of about 0.05 to 100 mg/kg/day, administered one to four times daily orally and IV. Typical treatment would be an initial IV loading dose followed by oral dosing for a few days or more.

In treating atherosclerosis and emphysema the amino substituted steroids (XI) and the $\Delta^{9(11)}$steroids (VI) are given orally in a dose of about 0.05 to about 100 mg/kg/day, one to four times daily for months or years.

In treating dermatological inflammatory conditions including psoriasis the amino substituted steroids (XI) and the $\Delta^{9(11)}$steroids (VI) are given orally in a dose of about 0.05 to about 100 mg/kg/day, one to four times daily or applied topically as a cream, ointment or lotion or equivalent dosage form in a concentration of about 0.05 to about 5% as long as needed. In treating these conditions the amino substituted steroids (XI) and the $\Delta^{9(11)}$steroids (VI) can be used with other steroidal agents.

In promoting burn healing and wound healing the amino substituted steroids (XI) and the $\Delta^{9(11)}$steroids (VI) are given orally or IV in a dose of about 0.05 to about 100 mg/kg/day administered one to four times daily orally and IV. Typical treatment would be an initial IV loading dose of 0.01 to 1 mg/kg followed by oral dosing for a few days.

The amino substituted steroids (XI) and the $\Delta^{9(11)}$steroids (VI) are useful in the prevention and treatment of stress ulcers and of gastric intolerance caused by drugs such as non-steroidal anti-inflammatory compounds (NOSAC). Stress ulcers are ulcers that develop after exposure to severe conditions such as trauma, burns, sepsis, extensive surgery, acute illnesses, and the like. Patients in intensive care units are particularly prone to develop stress ulcers. Stress ulcers also include lesions that can lead to upper gastrointestinal bleeding; such bleeding is likely to be prevented or stopped by these compounds. NOSAC includes drugs such as ibuprofen, aspirin, indomethacin, naproxen, piroxicam and the like that are usually taken for analgesia, and that are often associated with gastrointestinal intolerance characterized by pain and lesions that may lead to bleeding. The amino substituted steroids (XI) and the $\Delta^{9(11)}$steroids (VI) will be administered preferentially by the oral route either as tablets, capsules or liquids, in doses ranging from 5 to 500 mg, two to four times a day. The treatment would be either preventive, i.e., starting before ulcers have formed in patients at risk of developing such lesions, or therapeutic, i.e., once the ulcers have formed. In patients whose clinical condition precludes swallowing the oral dosage forms, the amino substituted steroids (XI) and the $\Delta^{9(11)}$steroids (VI) would be given either through a nasogastric tube, or parenterally, i.e., IV or IM. The parenteral doses would range from about 1 to about 100 mg and be administered one to four times a day or by IV.

In dogs, the amino substituted steroids (XI) and the $\Delta^{9(11)}$steroids (VI) are useful in treating head and spinal trauma, intervertebral diseases (slipped disk), traumatic shock, flea bite and other allergies.

In horses, the amino substituted steroids (XI) and the $\Delta^{9(11)}$steroids (VI) are useful in treating endotoxic or septic shock which follows colic, pretreatment before surgery for colic and treatment of Founder (laminitis).

In cattle, the amino substituted steroids (XI) and the $\Delta^{9(11)}$steroids (VI) are useful in treating acute coliform mastitis, bovine mastitis and acute allergic reaction to feed lot vaccination.

In pigs, the amino substituted steroids (XI) and the $\Delta^{9(11)}$steroids (VI) are useful in treating porcine stress syndrome and thermal stress syndrome.

The term treatment or treating as used in this patent is used broadly and includes both treatment of an existing condition as well as preventing the same condition from occurring where such is possible as is well known to those skilled in the art. For example, the amino substituted steroids (XI) and the $\Delta^{9(11)}$steroids (VI) can be used to treat existing asthma conditions and to prevent future ones from occurring. For example, the amino substituted steroids (XI) and the $\Delta^{9(11)}$steroids (VI) treat spinal a and prevent rejection of skin grafts.

The exact dosage and frequency of administration depends on the particular amino substituted steroids (XI) and the $\Delta^{9(11)}$steroids (VI) used, the particular condition being treated, the severity of the condition being treated, the age, weight, general physical condition of the particular patient, other medication the individual may be taking as is well known to those skilled in the art and can be more accurately determined by measuring the blood level or concentration of the amino steroid (I), aromatic steroid (II), $\Delta^{16}$-steroid (III), reduced A/B-ring steroid (IV), $\Delta^{17(20)}$-steroid (V) and $\Delta^{9(11)}$-steroid (VI) in the patient's blood and/or the patients response to the particular condition being treated.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "Z" or "$R_i$" where "i" is an integer. These variable substituents are either monovalent or bivalent, that is represent a group attached to the formula by one or two chemical bonds. For example, a group Z would represent a bivalent variable if attached to the formula $CH_3-C(=Z)H$. Groups $R_i$ and $R_j$ would represent monovalent variable substituents if attached to the formula $CH_3$—$CH_2$—$C(R_i)(R_j)H_2$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain, more specifically it represents a carbon-carbon bond. Thus $CH_3$—O—$CH_2$—$C(R_i)H$—$CH_3$ represents a 2-substituted-1-methoxypropane compound. In a similar fashion, the symbol "=" represents a double bond, e.g., $CH_2$=$C(R_i)$—O—$CH_3$, and the symbol "≡" represents a triple bond, e.g., HC≡C—$CH(R_i)$—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=$C(CH_3)$—CH=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*—$(CH_2)_2$—$N(C_2H_5)$—$CH_2$—C*$H_2$.

A cyclic (ring) structure for any compound herein defines an orientation with respect to the plane of the ring for substituents attached to each carbon atom of the cyclic compound. In formulas depicting such compounds, a substituent attached to a carbon atom below the plane of the ring is identified as being in the alpha (α) configuration and is indicated by a broken, dashed or dotted line attachment to the carbon atom, i.e., by the symbol "- - -" or "...". The corresponding substituent attached above the plane of the ring is identified as being in the beta (β) configuration. When a variable substituent is bivalent, the valences may be taken together or separately or both in the definition of the variable. For example, a variable $R_i$ attached to a carbon atom as —C(=$R_i$)— might be bivalent and be defined as oxo or keto (thus forming a carbonyl group (—CO—) or as two separately attached monovalent variable substituents α-$R_{ij}$ and β-$R_{ik}$. When a bivalent variable, $R_i$, is defined to consist of two monovalent variable substituents, the convention used to define the bivalent variable is of the form "α-$R_{ij}$:β-$R_{ik}$" or some variant thereof. In such a case both α-$R_{ij}$ and β-$R_{ik}$ are attached to the carbon atom to yield —C(α-$R_{ij}$)(β-$_{ik}$)—. For example, when the bivalent variable $R_6$, —C(=$R_6$)— is defined to consist of two monovalent variable substituents, two monovalent variable substituents are α-$R_{61}$:β-$R_{62}$, ... α-$R_{69}$:β-$R_{610}$, etc, yielding —C(α-$R_{61}$)(β-$R_{62}$)—, ... —C(α-$R_{69}$)(β-$R_{610}$)—, etc. Likewise, for the bivalent variable $R_{11}$, —C(=$R_{11}$)—, two monovalent variable substituents are α-$R_{111}$:β-$R_{112}$. For a ring substituent for which separate α and β orientations do not exist (e.g. due to the presence of a carbon carbon double bond in the ring), and for a substituent bonded to a carbon atom which is not part of a ring the above convention is still used, but the α and β designations are omitted.

Just as a bivalent variable may be defined as two separate monovalent variable substituents, two separate monovalent variable substituents may be defined to be taken together to form a bivalent variable. For example, in the formula —$C_1(R_i)H$—$C_2(R_j)H$— ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation "... $R_i$ and $R_j$ are taken together to form —$CH_2$—$CH_2$—O—CO— ..." means a lactone in which the carbonyl is bonded to $C_2$. However, when designated "... $R_j$ and $R_i$ are taken together to form —$CH_2$—$CH_2$—O—CO— the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus C2-C4 alkoxycarbonyl describes a group $CH_3$—$(CH_2)_n$—O—CO— where n is zero, one or 2. By the second method the carbon atom content of only each portion of the definition is indicated separately by enclosing the "Ci-Cj" designation in parentheses and placing it immediately (no intervening space) before the portion of the definition being defined. By this optional convention (C1-C3)alkoxycarbonyl has the same meaning as C2-C4 alkoxycarbonyl because the "C1-C3" refers only to the carbon atom content of the alkoxy group. Similarly while both C2-C6 alkoxyalkyl and (C1-C3)alkoxy(C1-C3)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a (cyclic) substituent, at the end of the phrase naming/designating that particular substituent will be a notation in [brackets] or in (parentheses) which will correspond to the same name/designation in one of the CHARTS which will also set forth the chemical structural formula of that particular substituent.

II. DEFINITIONS

All temperatures are in degrees Centigrade.

TLC refers to thin-layer chromatography.

TBF refers to tetrahydrofuran.

DMF refers to dimethylformamide.

DMA refers to dimethylacetamide.

DBU refers to 1,5-diazabicyclo[5.4.0]undec-5-ene.

DBN refers to 1,5-diazabicyclo[3.4.0]non-5-ene.

DCC refers to dicyclohexylcarbodiimide.

DDQ refers to 2,3-dichloro-5,6-dicyano-14-benzoquinone.

HOBT refers to 1-hydroxybenzotriazole.

DMSO refers to dimethylsulfoxide.

p-TSA refers to p-toluenesulfonic acid.

Saline refers to an aqueous saturated sodium chloride solution.

Physiological (normal) saline refers to 0.9% aqueous sodium chloride solution.

UV refers to ultraviolet spectroscopy.

IR refers to infrared spectroscopy.

NMR refers to nuclear (proton) magnetic resonance spectroscopy, chemical shifts are reported in ppm ($\delta$) downfield from tetramethylsilane.

MS refers to mass spectrometry expressed as m/e or mass/change unit $[M+H]^+$ refers to the positive ion of a parent plus a hydrogen atom.

dec refers to decomposition.

Amino substituted steroids (XI) refer to the amino steroids (Ia and Ib), aromatic steroids (II), $\Delta^{16}$-steroids (IIIa and IIIb), reduced A-ring steroids (IV) and $\Delta^{17(20)}$-steroids (Va and Vb) and pharmaceutically acceptable salts thereof and hydrates thereof.

The steroids of the Examples were chromatographed on 40–60 micron silica get by flash chromatography.

The hplc system used in the Examples is a paired ion, gradient, C-18 system. Solvent A is t-butylammonium phosphate (1 g) in buffer (pH 3, 900 ml) and acetonitrile (100 ml). Solvent B is t-butylammonium phosphate (1 g) in acetonitrile (1000 ml). The flow is 1.5 ml/min. The gradient is 90% of A to 80% of B over 25 min. Detection is by UV light at 254 nm.

Ether refers to diethyl ether.

Alcohol refers to ethyl alcohol.

Allyl refers to 2-propen-1-yl.

ARDS refers to acute/adult respiratory distress syndrome.

IV refers to intravenous, including injection, infusion and continuous drip.

IM refers to intramuscular.

IA refers to intra-arterial.

Pharmaceutically acceptable refers to those properties and/or substances which are acceptable to the patient from a pharmacological/toxicological point of view including bioavailability and patient acceptance or to the manufacturing chemist from a physical-chemical point of view regarding composition, formulation, stability and isolatability.

When solvent pairs are used, the ratios of solvents used are volume/volume (v/v).

_ indicates that there are 2 possible orientations for the group, (1) $\alpha$ or $\beta$ when attached to the steroid ring and (2) cis or trans when attached to a carbon atom of a double bond.

Aqueous workup (organic solvent, drying agent) refers to quenching the reaction mixture with water, dilution with the indicated organic solvent, separation of the organic layer, extraction of the aqueous layer several times with the organic solvent, drying the combined organic layers with the indicated drying agent and removal of the organic solvent using a rotary evaporator under reduced pressure.

Basic workup (organic solvent, aqueous base, drying agent) refers to a workup procedure similar to aqueous work-up, except the indicated aqueous base is used instead of water.

Acidic workup (organic solvent, organic solvent, drying agent) refers to dilution of the reaction mixture with the first indicated organic solvent, extraction of the organic mixture several times with hydrochloric acid (1N), basification of the combined acidic layers with solid sodium or potassium hydroxide, extraction of the basic mixture with the second indicated organic solvent several times, drying the organic phases with the indicated drying agent and removal of the solvent with a rotary evaporator under reduced pressure.

[NNNNNN-NN-N] refers to Chemical Abstracts Service (CAS, Columbus, Ohio) registry numbers where each N is an integer from 0 through 9, but deleting leading zeros in the 6-digit portion of the number. Registry numbers are assigned to a particular chemical compound by CAS only when there is sufficient proof according to CAS criteria that the compound has been found to exist and it has been characterized in some way. Compounds published from approximately 1967 to the present are registered publicly and the registry number is the key to finding references in the CAS data base for such a registered compound. The CAS database is publicly available from several database vendors such as STN International, System Development Corporation (SDC) Orbit Search Service, Lockheed Dialog, Bibliographic Retrieval Systems, Quester, etc. CAS registry numbers are included in the EXAMPLES for some of the compounds which have been registered.

Aldrich item refers to an item listed for sale by Aldrich Chemical Co., P.O. Box 355, Milwaukee, Wisc., 53201, U.S.A. in their 1984–1985 catalog.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION A-1

Methyl[2-(methyl-2-pyridinylamino)ethyl]amine

A mixture of N,N'-dimethylethylene-diamine (25 g) and 2-chloropyridine (1.3 g) is warmed at 85° with stirring for 18 h. The excess dimethylethylenediamine is removed by distillation at reduced pressure. The distillation residue is distributed between ethyl acetate (150 ml) and water (100 ml). The organic phase is separated, dried over sodium sulfate and the organic solvent removed under reduced pressure to give the title compound.

PREPARATION A-2

2-Carboxy-1-piperidine

[535-75-1], see Aldrich item P4,585-0.

PREPARATION A-3

4-(2-Furonylcarbonyl)piperazine

See Example 6B.

PREPARATION A-6

4-(2-Pyridinyl)piperazine

[34803-66-2], see French Patent 7253 M.

PREPARATION A-7

4-(2-Pyridinylmethyl)piperazine

[55579-01-6], see European Patent application 49,683.

PREPARATION A-8

4-(6-Methoxy-2-pyridinyl)piperazine

[51047-54-2], see Canadian Patent 979,894.

PREPARATION A-9

4-[(3-Hydroxy-2-pyridinyl)methyl]piperazine

A mixture of t-butyloxycarbonylpiperazine (2.3 g), 3-hydroxypyridine (0.98 g), formaldehyde (37%, 2.0 ml) and absolute ethanol (25 ml) are heated at 78° for 44 hr. The ethanol is removed under reduced pressure and the residue distributed between chloroform (150 ml) and sodium carbonate (0.1N, 100 ml). The aqueous phase is extracted with chloroform (100 ml). The organic phases are combined and washed with saline, dried over sodium sulfate and concentrated to a solid. The solid is dissolved in chloroform and chromatographed on a flash column using silica gel (150 g) eluting with ethyl acetate/methanol/ammonium hydroxide (9.9/0.8/0.2). The appropriate fractions are pooled and concentrated to give 4-[(3-hydroxy-2-pyrinidinyl)-methyl]-1-piperazinecarboxylic acid t-butyloxy ester. This material is dissolved in methylene chloride (10 ml), cooled to 0° in an ice/water bath. Trifluoroacetic acid (10 ml) is added over 3 min. The mixture is stirred at 0° for 30 min and then allowed to warm to 20°–25° for 1 hr. The solvents are removed under induced pressure and the residue is distributed between chloroform (100 ml) and saturated sodium bicarbonate (100 ml). The aqueous phase is extracted (2×) with chloroform (75 ml). The organic phases are combined, dried over sodium sulfate and concentrated to an oil. The aqueous bicarbonate phase is extracted with ethyl acetate for 48 hr. The ethyl acetate is removed under reduced pressure to leave an oil. These oils are combined to give the title compound, m.p. 254°; MS 193 (electron impact) m/e.

PREPARATION A-10

4-[6-(1-Pyrrolidinyl)-2-pyridinyl]piperazine

A solution of 2,6-dichloropyridine (10 g) and piperazine (25 g) in pyridine (30 ml) is stirred at 65° for 3 h and at 20°–25° overnight. The reaction mixture is concentrated, the residue is partitioned between ether and aqueous potassium carbonate. The organic phase is separated, washed with saline, dried over sodium sulfate and concentrated. The residue is added to pyrrolidine (15 g), pyridine (100 ml) and heated at 100° for 6 days. The reaction mixture is concentrated. The residue is partitioned between methylene chloride and aqueous sodium bicarbonate. The organic phase is separated, dried and concentrated. The residue is chromatographed on silica gel, eluting with methanol/ammonium hydroxide/methylene chloride (15/1/84). The appropriate fractions are pooled and concentrated to give the title compound, NMR (CDCL$_3$) 1.9, 2.9, 3.4, 5.75, 6.5, 7.3 δ.

PREPARATION A-11

4-[3-Amino-6-(diethylamino)-2-pyridinyl]piperazine

Diethylamine (3.29 ml) is added dropwise over 1 hr to a mixture of 2,6-dichloro-3-nitropyridine (6.13 g), acetonitrile (100 ml) and potassium carbonate (5.2 g) precooled to 0°. The resulting mixture is allowed to slowly warm to 20°–25° and is stirred for 16 hr. The mixture is filtered, the filtrate combined with piperazine (12.2 g) and potassium carbonate (6.0 g). The resulting mixture is heated at reflux for 24 hr and allowed to cool to 20°–25°. Aqueous workup (methylene chloride, water wash of organic layers and potassium carbonate) and purification by flash chromatography over silica gel eluting with methylene chloride/methanol (20/1 to 5/1), pooling and concentration of the appropriate fractions gives 6-N,N-diethylamino-3-nitro-2-(1-piperazinyl)piperidine.

A mixture of 6-N,N-diethylamino-3-nitro-2-(1-piperazinyl)piperidine (21.8 g), ethanol (275 ml), hydrochloric acid (1.2N, 27 ml) and palladium on charcoal (10%, 5.25 g) is exposed to hydrogen at 50 psi in a Parr flask. After 16 h the residue is filtered through celite, concentrated and partitioned between chloroform and 5% sodium hydroxide. The organic phase is separated, dried over potassium carbonate, concentrated and the residue passed through a plug of silica gel eluting with chloroform/methanol/ammonium hydroxide (4/1/0.25). The appropriate fractions are pooled and concentrated to give the title compound, IR (nujol) 3309, 2967, 2828, 1581, 1474, 1451, 1258 and 803 cm$^{-1}$; NMR (CDCl$_3$) 1.05, 2.9–3.1, 3.2, 3.2–3.4, 6.25 and 6.94 δ; MS (electron impact) 2.49, 2.20, 207, 193, 177 and 163.

PREPARATION A-13

4-[6-(Diethylamino)-3-(dimethylamino)-2-pyridinyl]piperazine

Sodium cyanoborohydride (0.5 g) is added to a mixture of 3-amino-6-N,N-diethylamino- 2-((4-t-butylcarbamate)piperazin-1-yl)piperidine (1.1 g), formalyn (37%, 11 ml) and acetonitrile (33 ml). The mixture is stirred for 24 h at 20°–25°, basic workup (chloroform, sodium carbonate, sodium sulfate) and flash chromatography over silica gel eluting with hexane ethyl acetate (4/1) provides the protected form of the title compound. The protected amine (967 ml), ethyl acetate (20 ml) and hydrochloric acid (3.0N, 50 ml) is stirred for 3 h at 20°25°. Basic workup (chloroform, 10% sodium hydroxide, sodium carbonate) gives the title compound, IR (nujol) 3289, 2935, 2820, 1589, 1566, 1479, 1445, 1429, 1373, 1263, 1236 and 940 cm$^{-1}$; NMR (CDCl$_3$) 2.9–3.1, 3.3–3.5, 3.51, 6.06 and 7.10 δ.

PREPARATION A-14

4-[4,6-Bis(2-propenylamino)-1,3,5-triazin-2-yl]piperazine

A solution of 2-chloro-4,6-bis(2-propenylamino)-1,3,5-triazine (10.44 g) and 15.95 g of piperazine in 150 ml of DMF is heated under reflux for about 18 hours. The reaction mixture is cooled and stored at 5° and crystals are deposited. The soluble fraction is concentrated and the residue is extracted with ethyl acetate. The extracts are washed with aqueous potassium carbonate, 50% saline and saline and dried over magnesium sulfate and concentrated to give a gum. Chromatography on silica gel (400 g) and elution (200 ml fractions) with 20% acetonemethylene chloride gives the formamide. The formamide (9.2 g) in 200 ml of methanol is heated to reflux, then cooled under nitrogen and mixed with 4 ml of 45% potassium hydroxide solution. The mixture is heated under reflux for about 20 hours, then cooled and concentrated. The residue is partitioned between ethyl acetate and water. The organic extracts are washed with water and saline, dried over magnesium sulfate and concentrated to give a gum. Crystallization from 50 ml of carbon tetrachloride gives the title compound, mp 93°–94.5°.

PREPARATION A-15

4-[2,6-Bis(diethylamino)-4-pyrimidinyl]piperazine

See Example O.

PREPARATION A-16

4-[6-Amino-4-(diethylamino)-2-pyrimidinylpiperazine

Dry piperazine (3.59 g) and 2-amino-4-diethylamino-6-chloropyrimidine (1.55 g) are heated at 100° in ethylene glycol (20 ml) for 4 h. The mixture is partitioned between methylene chloride and aqueous sodium bicarbonate. The phases are separated, the organic phase is dried with sodium sulfate and concentrated. The residue is chromatographed on silica gel eluting with ethyl acetate to 1% methanol/ethyl acetate to 20% methanol/1% ammonia/ethyl acetate. The appropriate fractions are pooled and concentrated to give the title compound, TLC (ethyl acetate/0.5% ammonium hydroxide) $R_f$=0.7.

PREPARATION A-17

4-[2,6-Bis(dimethylamino)-4-pyrimidinyl]piperazine

A mixture of dimethylamine (16.6 g, 25% in water), triethylamine (20 g) and 1,3,5-trichloropyrimidine (8.3 g) in ethanol (100 ml) is stirred at 20°–25° for 2 h. The mixture is stored at 0° overnight. Additional dimethylamine solution (2 g) is added and the reaction is stirred at 20°–25° for 2 h. The mixture is partitioned between methylene chloride and aqueous sodium bicarbonate. The organic phase is dried over sodium sulfate and concentrated. The residue is chromatographed over silica gel eluting with 10% ethyl acetate/hexane to give pure 2,4-bis[dimethylamino]-6-chloropyrimidine. This bis-adduct is heated with piperazine (2.6 g) in ethanol (100 ml) for 1 h. The mixture is partitioned between methylene chloride and aqueous sodium bicarbonate. The phases are separated, the organic phase is dried over sodium sulfate and concentrated. The residue is crystallized from ether and hexane to give the title compound, NMR (CDCl$_3$) 2.05, 3.0, 3.75 and 5.7 δ.

PREPARATION A-18

4-[2-(Diethylamino)-6-(1-pyrrolidinyl)-pyrimidinyl]piperazine

A solution of 2-diethylamino-4-piperazino-6-chloropyrimidine (4.10 g) in pyrrolidine (4.10 g) is heated at 100° for 12 h. The mixture is concentrated and the residue is partitioned between aqueous sodium bicarbonate and methylene chloride. The phases are separated and the organic phase is dried and concentrated to give the title compound, NMR (CDCl$_3$) 1.15, 1.90, 2.90, 3.45, 3.70 and 4.75 δ.

PREPARATION A-19

4-[2,6-Bis(4-methyl-1-piperazinyl)-4-pyrimidinyl]piperazine

Trichloropyrimidine is added in portions to an ice cool solution of N-methylpiperazine (40 g) in ethanol (200 ml). The mixture is then heated at 60° for 2 h. The mixture is concentrated and chromatographed on silica gel with 2–5% methanol and methylene chloride to give 2,4-bis[4-methylpiperazinol-6-chloropyrimidine. This material is heated at 130° in water (30 ml) with piperazine (32 g) in a Parr bomb for 20 h. The product is partitioned between methylene chloride and aqueous sodium carbonate. The phases are separated and the organic phase is dried over sodium sulfate and concentrated to give the title compound, TLC (methylene chloride/methanol/ammonium hydroxide—91.5/8/0.5) $R_f$=0.3.

PREPARATION A-20

4-[2-(Diethylamino)-6-(4-methyl-1-piperazinyl)-4-pyrimidinyl]piperazine

2-Diethylamino-4,6-dichloropyrimidine (10 g) is reacted with piperazine (14.45 g) in ethanol (200 ml) at reflux for 2 hr. The mixture is concentrated and the product isolated by silica gel chromatography giving 2-diethylamino-4-piperazino-6-chloropyrimidine. The 2-diethylamino-4-piperazino-6-chloropyrimidine (8 g) and N-methylpiperazine (8 g) is heated neat at 70° for 16 hr. Then water (2.5 ml) is added and the mixture is heated at 100° for 50 hr. The mixture is chromatographed on silica gel, the appropriate fractions are pooled and concentrated to give the title compound, NMR (CDCl$_3$) 1.15, 2.80, 2.85, 2.90, 3.30, 3.70 and 4.95 δ.

PREPARATION A-21

4-[2-(Diethylamino)-6-(1-piperidinyl)-4-pyrimidinyl]piperazine

A solution of 2-diethylamino-4,6-dichloropyrimidine (4 g) in piperidine (6 g) is heated at 80° for 20 min. The mixture is stirred at 20°–25° for 15 h and then partitioned between methylene chloride and aqueous sodium carbonate. The phases are separated, the organic phase is dried over sodium sulfate and concentrated. The residue and piperazine (8 g) are refluxed in pyridine (100 ml) for 6 h. The reaction is partitioned between methylene chloride and aqueous potassium carbonate. The organic phase is dried over sodium sulfate, concentrated to a residue which is chromatographed on silica gel eluting with methylene chloride to 6% methanol/1% ammonium hydroxide/methylene chloride. The appropriate fractions are pooled and concentrated to give the title compound, NMR (CDCl$_3$) 1.15, 1.53, 2.90, 3.45 and 4.95 δ.

PREPARATION A-22

4-[2,6-Bis(1-pyrrolidinyl)-4-pyrimidinyl]piperazine

A solution of pyrrolidine (80 g) in THF (500 ml) is chilled in an ice water bath and stirred mechanically under nitrogen. With a syringe pump of 2,4,6-trichloropyrimidine (50 g) is added over 35 minutes. The reaction is stirred in the ice bath for 1 hour and is then warmed to 20°–25° over 4 h. Pyridine (100 ml) is added to the reaction and the mixture stirred at 20°–25° overnight. The reaction is concentrated. The residue is partitioned between methylene chloride and aqueous sodium bicarbonate. The organic phase is concentrated and the residue chromatographed on silica gel (10% ethyl acetate/hexane) to yield 51 g of crystalline 2,4-bis[pyrrolidino] -6-chloropyrimidine. Immediately after the initial addition of reagents, two spots are seen with 25% ethyl acetate on a silica gel plate. These are the 2- and the 4-adducts. The bis product forms over time. It moves between these first two spots. The 51 g of product is reacted with piperazine (40 g) in 100 ml of dry pyridine at 100° for 50 h. The reaction is concentrated. The residue is partitioned between methylene chloride and sodium bicarbonate solution. The organic phase is dried and concentrated. The residue is chromatographed on silica gel eluting with methylene chloride to 10% methanol/1% ammonia/methylene chloride to give the title compound, NMR (CDCl$_3$) 1.90, 2.9, 3.35 and 4.80 δ.

PREPARATION A-23

4-[2,6-Bis(4-morpholino)-4-pyrimidinyl]piperazine

A solution of 160 g of morpholine in 1000 ml of methylene chloride is treated dropwise with 100 g of 2,4,6-trichloropyrimidine. The reaction is immersed in an ice water bath. After 1 h, 300 ml of pyridine is added. The reaction is stirred for two days and concentrated. The residue is partitioned between methylene chloride and aqueous sodium bicarbonate. The residue is chromatographed on silica gel (10% ethyl acetate/hexane to 25% to methylene chloride) to give 2,4-[bis(4-morpholino)]-6-chloropyrimidine. A solution of 40 g of 2,4-[bis-morpholino]-6 -chloropyrimidine and 34 g of piperazine in 60 g of pyridine is heated at 100° for 24 h. The mixture is partitioned between methylene chloride and aqueous potassium carbonate. The organic phase is filtered through sodium sulfate and concentrated. The residue is chromatographed (methylene chloride to 4% methanol/1% ammonium hydroxide/methylene chloride) to give the title compound, NMR (CDCl$_3$) 2.90, 3.50, 3.75, 3.80 and 5.10 δ.

PREPARATION A-24

4-[2,6-Bis(allylamino)-4-pyrimidinyl]piperazine

Following the general procedure for PREPARATION A-22, and making non-critical variation but substituting allylamine for pyrrolidine the title compound is obtained.

PREPARATION A-25

4-(2-Pyrimidinyl)piperazine [20980-22-7]

See U.S. Pat. No. 4,409,223.

PREPARATION A-26

4-[4,6-Bis(diethylamino)-2-pyrimidinyl]piperazine

Diethylamine (80 g) is reacted with trichloropyrimidine (50 g) in THF. The reaction after chromatography yields a mixture of the mono- and di-adduct. This material is dissolved in pyridine (58 g) and reacted with diethylamine (35 g) at 50° for 3 h. The reaction is concentrated to a residue. The residue is partitioned between methylene chloride and aqueous sodium bicarbonate. The organic phase is separated and concentrated. The residue is chromatographed on silica gel, eluting with ethyl acetate/hexane (10/90). The appropriate fractions are pooled and concentrated to give 2,4-bis [diethylamino]-6-chloropyrimidine. This material is dissolved in pyridine (100 g) and reacted with piperazine (40 g) at 100° for 50 h. Following the above workup procedure the title compound is obtained, NMR (CDCl$_3$) 1.15, 2.90, 3.45 and 4.9 δ.

PREPARATION A-27

4-(3,6-Dimethylpyrazinyl)piperazine [59215-42-8]

See Canadian Patent 979,894.

PREPARATION A-28

4-[(5-Methyl)-4-phenyl-4H-1,2,4-triazol-3-yl]piperazine

A mixture of 3-bromo-5-methyl-4-phenyl-4H-1,2,4-triazole (4.16 g), 15.07 g of piperazine and 20 ml of pyridine is stirred at 100° under nitrogen for 22 h. The reaction is monitored by TLC (8% methanol/methylene chloride) and after this period of time no change occurs. The mixture is subsequently placed in a Parr bomb and heated in an oil bath at 180° for 24 h. Bomb pressure increases by 40 psi. The mixture is worked up by partitioning between chloroform and water. The organic phase is washed with saturated aqueous sodium bicarbonate (2×) and with saline (2×), dried over sodium sulfate and concentrated to a solid, the product is recrystallized in ethyl acetate, MS [M+H]$^+$ 243.1484

PREPARATION A-29

4-(Benzo[b]thien-2-yl)piperazine

2-Chlorobenzothiazole (5 g) is heated in ethanol (75 ml) with piperazine (3.05 g) for 20 h. The mixture is partitioned between methylene chloride/ether and aqueous sodium bicarbonate. The organic phase is separated, dried with sodium sulfate and concentrated to give the title compound.

PREPARATION A-30

4-(2-Methoxyphenyl)piperazine

[35386-24-4], see Aldrich item M2,260-1.

PREPARATION A-31

4-(4-Methoxyphenyl)piperazine

[70849-64-8], see Aldrich item M2,300-4.

PREPARATION A-32

4-[(3,4-Dimethoxyphenyl)methyl]piperazine

See French Patent 7031 M.

PREPARATION A-33

4-(4-Fluorophenyl)piperazine

[2252-6-3-3], see Aldrich item 19,133-7.

PREPARATION A-34

4-[2-Amino-5-(1-pyrrolidinyl)phenyl]piperazine

Pyrrolidine (2.0 ml) is added to a mixture of 2,4-dichloronitrobenzene (4.50 g), acetonitrile (25 ml) and potassium carbonate 4.90 g). After stilling for 48 hr at 20°–25° basic workup gives 1-nitro-2-piperazinyl-4-pyrrolidinylbenzene.

A mixture of 1-nitro-2-piperazinyl-4-pyrrolidinylbenzene (4.57 g), ethanol (110 ml), hydrochloric acid (1.2N, 6 ml) and palladium on carbon (10%, 1 g) is exposed to hydrogen 51 psi at 20°–25° in a Parr flask. After 16 h (49 psi total uptake) the mixture is filtered. Basic workup (chloroform, potassium carbonate) and column chromatography silica gel (50 g) eluting with chloroform/methanol (4/1) gives the title compound as an oil, IR (nujol) 3315, 2947, 2816, 1512, 1258, 1001 and 753 cm$^{-1}$; NMR (CDCl$_3$) 1.8–2.0, 2.9–3.2, 6.52 and 6.6–6.8 δ; MS (electron impact) 246, 204 and 189.

PREPARATION A-35

4-[[4-(Dimethylamino)phenyl]methyl]piperazine

See U.S. Pat. No. 4,421,753.

PREPARATION A-36

4-Hydroxy-4-[4-(trifluoromethyl)phenyl]piperidine [39757-71-6]

See U.S. Pat. No. 3,936,464.

PREPARATION A-37

(2-Diethylaminoethyl)amine

[111-74-0], see Aldrich item 12,694-2.

PREPARATION A-38

[2-(3,4-Dimethoxyphenyl)ethyl]amine

[120-20-7], see Aldrich item D13,620-4.

PREPARATION A-39

[2-(2,4-Dimethoxyphenyl)-1-methylethyl]amine

See J. Pharm. Sci. 60, 1232 (1971).

PREPARATION A-40

[2-(3,4-Dimethoxyphenyl)ethyl][3,4,5-trimethoxyphenyl)-methyl]amine

A mixture of 3,4-dimethoxyphenylamine (2.87 g), 3,4,5-trimethoxybenzaldehyde (3.15 g), benzene (100 ml) and p-TSA (276 ml) is heated at reflux in a Dean Stark apparatus. After 16 hours, the mixture is allowed to cool to 20°–25°. Basic workup (methylene chloride, sodium bicarbonate, magnesium sulfate) gives an imine. Sodium borohydride (1.2 g) is added in several portions over 2 hours to the imine in methanol (65 ml) and hydrochloric acid (1.2N, 7.4 ml). After 3 hours, acidic workup (ether, chloroform, sodium carbonate) gives the title compound as an oil, IR (Nujol) 2939, 1591, 1516, 1463, 1420, 1236 and 1128 cm$^{-1}$; NMR (CDCl$_3$) 2.7–3.0, 3.7–4.0 and 6.5–6.9 δ; MS (chemical ionization) [M+H]$^+$ 360, 199, 182, 181.

PREPARATION A-41

[2-(3,4-Dimethoxyphenyl)ethyl][[4-(dimethylamino)phenyl]methyl]amine

[13159-97-2], see Chem. Abst. 65:7001f.

PREPARATION A-42

[(3,4-Dihydroxyphenyl)methyl][2-(3,4-dimethoxyphenyl)-ethyl]amine

A mixture of 3,4-dihydroxybenzaldehyde (1.25 g) t-butyldimethylsilyl chloride (3.5 g), dimethylformamide (10 ml) and imidazole (1.54 g) is stirred for 18 h at 20°–25°. The mixture is diluted with ether and washed successively with dilute hydrochloric acid and dilute sodium bicarbonate. The organic phase is separated and dried over magnesium sulfate and concentrated to give an oil homogeneous by TLC. The oil (3.3 g), 3,4-dimethoxyethylamine (1.77 g) toluene (50 ml) and p-TSA (150 ml) is heated at reflux in a Dean Stark apparatus for 24 h. Afterwards the solution is permitted to cool to 20°–25°, methanol (35 ml), hydrochloric acid (1.2N, 4.2 ml) and sodium borohydride (1 g) are added. After 2 h the mixture is concentrated, basic workup (chloroform, sodium carbonate, sodium sulfate) gives a compound which is purified by flash chromatography over silica gel diluting with chloroform/methanol (30/1). The appropriate fractions are pooled and concentrated to give the title compound as an oil, IR (nujol) 2931, 2858, 1511, 1297, 1259, 909, 840 and 782 cm$^{-1}$; NMR (CDCl$_3$) 0.19, 0.99, 2.7–2.9, 3.68, 3.87, and 6.6–6.9 δ; MS (chemical ionization) [M+H]$^+$ 532, 386, 351.

PREPARATION A-43

(2-Pyridinyl)methylamine

[3731-51-9], see Aldrich item A6,520-4.

PREPARATION A-44

4-[2-[4-[2,6-Bis(1-pyrrolidinyl)-4-pyrimidinyl]-1-piperazinyl] ethyl]piperazine

Several batches of di-t-butyl dicarbonate (17.7 g) is added to a stirred mixture of 2-hydroxyethylpiperazine (10.6 g) in ether (300 ml). The mixture is stirred at 20°–25° for 1.5 hr and then washed with sodium hydroxide (5%, 200 ml), saline (200 ml), dried over sodium sulfate, and filtered. The organic solvent is removed under reduced pressure to give an oil. The oil is flash chromatographed on silica gel (100 g), eluting with ethyl acetate/methanol/ammonium hydroxide (9.5/0.4/0.1). The appropriate fractions are pooled and concentrated to give the N-protected 2-hydroxyethylpiperazine.

The N-protected 2-hydroxyethylpiperazine (3.0 g), triethylamine (1.42 g) and methylene chloride (30 ml) is cooled to 0° in an ice bath under nitrogen. A mixture of methanesulfonyl chloride (1.64 g) in methylene chloride (30 ml) is added dropwise over 10 min. The cooling bath is removed and the mixture allowed to warm to 20°–25° for 30 min. The mixture is then washed with water (60 ml), dried over sodium sulfate and the solvent removed to give crude mesylate. 4-[2,6-Bis(1-pyrrolidinyl)-4-pyrimidinyl]piperazine (4.23 g), potassium carbonate (1.93 g) and acetonitrile (150 ml) are added to the crude mesylate. The mixture is heated at reflux for 18 hr. The acetonitrile is removed under reduced pressure and the residue distributed between chloroform (200 ml) and water (200 ml). The phases are separated, the organic phase is washed with saline, dried over sodium sulfate and the solvent removed under reduced pressure to give an oil. The oil is flash chromatographed on silica gel (200 g) with ethyl acetate/methanol/ammonium hydroxide (9.5/0.4/0.1). The appropriate fractions are pooled and concentrated to give the N-protected form of the title compound as a solid, mp 148°–149°.

This solid (0.75 g) in methylene chloride (10 ml) is stirred and cooled to 0° in an ice/water bath. Trifluoroacetic acid (10 ml) is added dropwise over 5 min. The cooling bath is removed and the mixture is stirred at 20°–25° for 1 hr. The organic solvent is removed under reduced pressure and the residue is distributed between methylene chloride (50 ml) and sodium hydroxide (10%, 50 ml). The organic phase is separated, and dried over sodium sulfate. The solvent is removed to give the title compound.

PREPARATION A-45

4-[4,6-Bis(1-pyrrolidinyl)-1,3,5-triazin-2-yl]-1-piperazine

Pyrrolidine (28.5 g) is cooled on an ice bath. 1,3,5-Trichlorotriazine (18.4 g) is added with vigorous stirring. After 1–1.5 h the mixture is permitted to warm to 20°–25°. The solid is filtered and rinsed several times with water and dried under reduced pressure to give the monochloro-bis(1-pyrrolidinyl)triazine.

This material (23.18 g) in piperazine (31.55 g) at DMF (295 ml) is refluxed under nitrogen. When the reaction is complete (TLC) the solvent is removed under reduced pressure. The mixture is transferred to a separatory funnel containing ethyl acetate (100 ml) and potassium carbonate (100 ml). The layers are separated, the organic layer is washed with saline (100 ml) and back-washed with ethyl acetate (2×100 ml). The organic layers are combined, dried over magnesium sulfate at room temperature, filtered and concentrated under reduced pressure. This material is chromatographed on a silica gel column (500 g) eluting with acetone/methylene chloride (5/95). The appropriate fractions (500 ml) are pooled and concentrated to give a solid.

The solid (10.13 g) is refluxed in methanol (200 ml) and cooled under nitrogen. Potassium hydroxide (45% aqueous, 4 ml) is added, the mixture degassed with nitrogen and heated to reflux. After 8 h the mixture is cooled to room temperature and concentrated under reduced pressure. The solid is transferred to a separatory funnel containing ethyl acetate (200 ml) and water (100 ml). The phases are separated, the organic layer is washed with water (2× 100 ml) and 50% brine (100 ml) followed by brine (2×100 ml). The aqueous washes are back-washed with 200 ml of ethyl acetate, the organic phases are combined, dried over magnesium sulfate, filtered, concentrated under reduced pressure to give the title compound, m.p. 162.5°–166°.

PREPARATION A-46

4-[5,6-Bis(diethylamino)-2-pyridinyl]piperazine

Diethylamine (3.29 ml) is added dropwise over 1 h to a mixture of 2,6-dichloro-3-[nitropyridine (6.13 g), acetonitrile (100 ml) and potassium carbonate (5.2 g) precooled to 0°. The mixture is allowed slowly to warm to 20°–25° and stirred for 16 h. The mixture is filtered, the filtrate combined with piperazine (12.2 g) and potassium carbonate (6 g). The resulting mixture is heated at reflux for 24 h and then permitted to cool to 20°–25°. Aqueous workup (methylene chloride, water washed over organic layers, potassium carbonate) and purification by flash chromatography (silica gel) eluting with chloroform/methanol (20:1 25:1) gives 2-N,N-diethylamino- 3-nitro-6-(1-piperazinyl)pyridine.

This material (21.8 g), ethanol (275 ml), hydrochloric acid (1.2N, 27 ml) and 10% palladium on charcoal (5.25 g) is exposed to hydrogen at 50 pounds per square inch in a Parr flask. After 16 h the residue is filtered through celite, concentrated and partitioned between chloroform and sodium hydroxide (5%). The organic layers are separated, dried using potassium carbonate, concentrated. The concentrate is passed through a plug of silica gel, eluting with chloroform/methanol/ammonium hydroxide (4/1/0.25) to give 5-amino-6-N,N-diethylamino- 2-(1-piperazinyl)pyridine.

A solution of di t-butyl dicarbonate (11.8 g) and methylene chloride (25 ml) is added dropwise over 30 min to a mixture of 5-amino-6-N,N-diethylamino-2-(1-piperazinyl)pyridine (13.5 g), triethylamine (8.33 ml) and methylene chloride (400 ml) precooled to 0°. The resulting mixture is allowed to slowly warm to 20°–25°. After 16 h using basic workup (methylene chloride, sodium bicarbonate, potassium carbonate) the t-butyl carbonate as a solid is obtained.

The protected piperazinyl pyridine (4 g) as an aldehyde (12.8 ml), acetonitrile (80 ml) is mixed. Sodium cyanoborohydride (1.73 g) is added to the pyridine mixture. The resultant solution is stirred for 48 h at 20°–25°. After 24 h additional sodium cyanoborohydride (500 ml) and acid aldehyde (5 ml) is added. Basic workup (chloroform/potassium carbonate, potassium carbonate) and purification by flash chromatography using silica gel and eluting with hexane ethyl acetate (5/1) gives an oil. The oil (2.36 g), ethyl acetate (50 ml), and hydrochloric acid (3.0N, 37.5 ml) are stirred for 16 h at 20°–25°. Basic workup (chloroform, 10% sodium hydroxide, potassium carbonate) gives the title compound, MS (electron impact) 305.

PREPARATION A-47

4-[3-(Ethylamino)-2-pyridinyl]piperazine 2-(1-piperazinyl)-3-nitropyridine (24.50 g), ethanol (445 ml) and hydrochloric acid (1.2 N, 44 ml) are combined and hydrogenated overnight at 40 psi, refilling when necessary. The mixture is filtered through celite, washed with ethanol, chloroform, ethanol and water. The organic solvents are removed with heat and reduced pressure. The remaining material is partitioned between methylene chloride (3×250 ml) and sodium bicarbonate. The organic layers are combined, dried over potassium carbonate, filtered and concentrated under reduced pressure to give an oil which slowly solidified upon standing to give 3-amino-2-(1-piperazinyl)pyridine.

3-Amino-2-(1-piperazinyl)pyridine (19.58 g), methylene chloride 600 ml), triethylamine (17.2 ml) are combined and cooled to 6°. Di-t-butyl-dicarbonate (24.34 g) in methylene chloride (50 ml) is added to the pyridine mixture over 30 min and permitted to stand at 0° for 1 hr, then allowed to warm to 20°–25°. After 30 min, TLC indicates no starting material remains. The reaction mixture is partitioned between sodium bicarbonate (500 ml) and methylene chloride (3×250 ml). The organic phases are combined, dried over potassium carbonate, filtered and concentrated under reduced pressure and heat to give a solid which is recrystallized from ethyl acetate to give 3-amino-2-[(4-t-butyldicarbonate)-1-piperazinyl]piperidine.

3-Amino-2-[(4-t-butyldicarbonate)-1-piperazinyl]piperidine (2.361 g), methanol (23.6 ml) and acetaldehyde (2.1 ml) are combined at 20°–25° to form a solution. Sodium cyanoborohydride (586 mg) is added and the mixture stirred overnight. The organic solvent is removed with reduced pressure and heat, the remaining mixture is partitioned between sodium bicarbonate (50 ml) and chloroform (3×50 ml). The chloroform extracts are combined and dried over potassium carbonate and filtered. The filtrate is concentrated with heat and reduced pressure. The concentrate is column chromatographed on silica gel 60 (40 63µ) eluting with hexane/ethyl acetate (2/1) containing triethylamine (1%). The appropriate fractions are pooled and concentrated to give 3-ethylamino-2-[(4-t-butyldicarbonate)-1-piperazinyl] piperidine.

3-Ethylamino-2-[(4-t-butyldicarbonate)-1-piperazinyl]piperidine (2.47 g), ethyl acetate (67 ml) and hydrochloric acid (3N, 49 ml) are combined and stirred for 2 hr at 20°–25°. TLC indicates no starting material. Potassium hydroxide (14 g) and water (80 ml) is added. The organic layer is removed and extracted with chloroform (3×60 ml). The organic layers are combined, dried over potassium carbonate, filtered and the filtrate concentrated to give the title compound, NMR (CDCl$_3$) 1.25, 1.50, 3.1, 3.5, 6.90 and 7.75 δ.

PREPARATION A-48

4-[3-(Diethylamino)-2-pyridinyl]piperazine

Following the general procedure of PREPARATION A-47 and making non-critical variation but reacting the protected ethylamine compound with additional acetaldehyde and again inducing the title compound is obtained, NMR (CDCl$_3$) 0.95, 3.25, 6.80, 7.20 and 7.90 δ.

PREPARATION A-49

4-[4,6-Bis(2-pyridinyl)-1,3,5-triazin-2-yl]piperazine

A mixture of 4-formyl-piperazinecarboximidamide hydroiodide (prepared according to U.S. Pat. No. 4,351,832) in ethanol (4 ml) and ethanolic sodium ethoxide (1.4N, 6.8 ml) is stirred for 15 min, then 2-cyanopyridine (2.08 g) is added. The mixture is concentrated at atmospheric pressure and heated at about 200° for 5 hr, then cooled and chromatographed on silica gel eluting with methanol/methylene chloride (30/70). The appropriate fractions are pooled and concentrated to give the 1-formyl 4-[4,6-bis(2-pyridinyl)-1,3,5-triazin-2-yl]piperazine. Hydrolysis of the formamide in the usual way (PREPARATION A-14) gives the title compound.

PREPARATION A-50

4-[5,6-Bis(2-pyridinyl)-1,2,4-triazin-3-yl]piperazine

A mixture, of 4-formyl-piperazinecarboximidamide hydroiodide (prepared according to U.S. Pat. No. 4,351,832) in ethanol (4 ml) and ethanolic sodium ethoxide (1.4N, 6.8 ml) is stirred for 15 min and then anhydrous hydrazine (0.32 g) in ethanol (3 ml) is added. The mixture is stirred an additional 15 min, then 2,2'-pyridil (2.12 g) is added. The mixture is stirred for 12 hours at 25° and concentrated. The residue is chromatographed on silica gel eluting with a methylene chloride/methanol mixture. The appropriate fractions are pooled and concentrated to give 1-formyl 4-[5,6-bis(2-pyridinyl)-1,2,4-triazin-3-yl]-piperazine. Hydrolysis of the formamide in the usual way (PREPARATION A-14) gives the title compound.

PREPARATION A-51

4-[2,6-Bis(2-pyridinyl)-4-pyrimidinyl]piperazine

4-Chloro-2,6-bis(2-pyridinyl)pyrimidine [prepared by the method of J.A.C.S. 32, 1591 (1967), 4.2 g] piperazine (13.44 g) and ethanol (70 ml) are heated at reflux for 2 hr. The mixture is allowed to cool and the solvent is removed under reduced pressure. The residue is dissolved in chloroform (250 ml), washed with water (twice), dried over sodium sulfate and concentrated under reduced pressure to give an oil. The oil is crystallized from ether to give the title compound, m.p. 159°–161°; MS (m/e) 318 (M$^+$)

PREPARATION A-55

3,6-Bis(2-pyridinyl)-4-pyridazine

PREPARATION A-56

6-Methoxy-2-morpholino-4-(1-piperazinyl)pyrimidine

A solution of 2,4,6-trichloropyrimidine (55 g), methanol (50 ml) and collidine (50 g) is heated in dry tetrahydrofuran (400 ml) for 48 hr. Ether is added and the precipitate is collected. The precipitate is column chromatographed on silica gel to give 6-methoxy-2,4-dichloropyrimidine. This product is mixed with morpholine in THF and stirred at 20°–25° to give 6-methoxy-2-morpholino-4-chloropyrimidine. The 6-methoxy-2-morpholino-4-chloropyrimidine is heated with piperazine in pyridine at 60° for 24 hr to give the title compound.

PREPARATION A-57

4-(3-Chlorophenyl)piperazine

[65369-76-8], see Aldrich catalog, 1986-7, 12,518-0.

PREPARATION A-58

4-[3-Diethylamino)-2-pyridinyl]piperazine

Sodium cyanoborohydride (3.06 g) is added to a solution of 2-(3 -ethylamino)pyridinylpiperazine (5.38 g), acetaldehyde (5.0 ml) and methanol (54 ml). The mixture is stirred for 10 days at 20°–25°. Acetaldehyde (5.0 ml) is added at 2, 3, 4 and 7 days. Sodium cyanoborohydride (3.06 g) is added at 3 and 7 days. After 10 days no further change in the reaction occurred as measured by TLC. Basic workup (chloroform/sodium bicarbonate/magnesium sulfate) gives an oil. The crude residue is resubmitted to the above reaction conditions. After 5 days the reaction is worked up as described above. Purification by flash chromatography (hexane/ethyl acetate; 5/1) provides the carbamate of the title compound, NMR (CDCl$_3$) 0.98, 1.49, 3.21, 3.35–3.65, 6.82, 7.16 and 7.92 δ; IR (neat) 2974, 1699, 1577, 1438, 1234 and 1172 cm$^{-1}$; MS (EI) m/e (relative percent) 334 (79), 205 (64), 178 (45), 162 (56), 57 (100).

The carbamate (1.17 g), ethyl acetate (29.0 ml) and hydrochloric acid (3N, 21.2 ml) are stirred at 20°–25° for 1.5 hr. Potassium hydroxide (8 g) and water (30 ml) are added. Aqueous workup (chloroform/potassium carbonate) gives the title compound, IR (nujol) 2957, 2925, 1574, 1450, 1249 and 776 cm$^{-1}$; NMR (CDCl$_3$) 0.96, 3.16, 3.15–3.3, 3.7–3.85, 6.84, 7.17 and 7.91 δ; MS (EI, relative percent) 234 (60), 178 (66), 162 (100) and 148 (67).

PREPARATION A-59

4-[4-Diethylamino-2-pyridinyl]piperazine

2-Chloro-5-nitropyridine (25 g) is dissolved in acetonitrile (150 ml) and the mixture is added dropwise over 30 min to a stirred suspension of piperizine (61.3 g) and potassium carbonate (26.2 g) in acetonitrile (550 ml). The reaction mixture is stirred at 20°–25° for 16 hr. The solvent is removed on a rotary evaporator and the residue is diluted with methylene chloride/water. The organic layer is separated and washed with water (twice) and saline, dried over potassium carbonate and concentrated to give 1-(4-nitro-2-pyridinyl)piperazine, IR 3338, 3102, 3068, 1603, 1570, 1482, 1347, 1340, 1320, 1306 and 1253 cm$^{-1}$.

The nitro compound (30.7 g) is dissolved in ethanol (500 ml), and palladium/carbon (10%, 10 g) and hydrochloric acid (1.2N, 55 ml) are added and the mixture hydrogenated on a Parr apparatus (50 psi) for 4 hr. The mixture is then filtered thru celite and the filtrate evaporated to dryness to give an oil. The residue is partitioned between saturated sodium bicarbonate and chloroform, the layers are separated, the aqueous layer is reextracted with chloroform (2×250 ml) and the organic phases are combined, dried over potassium carbonate and concentrated under reduced pressure. The pH of the aqueous phase is raised to 11 by the addition of solid potassium hydroxide, the mixture reextracted with chloroform, dried and concentrated to give the crude 4-amino compound. The aqueous layer is concentrated to half the volume, excess sodium chloride is added and the mixture is reextracted with chloroform. The extract is dried and concentrated to obtain additional 4-amino compound.

The amine (21 g), triethylamine (17.9 g) and methylene chloride (600 ml) are cooled to 0°. Di-t-butyl dicarbonate (25.8 g) in methylene chloride (200 ml) is added over 30 min at 0°. The reaction mixture is stirred at 0° for 1 hr and allowed to warm to 20°–25°. The reaction mixture is washed with saturated sodium bicarbonate (3×200 ml), dried over potassium carbonate and the solvent removed under reduced pressure to give a solid. The solid is dissolved in ether, petroleum ether is added until the mixture is cloudy, the mixture is filtered thru celite and the filtrate is concentrated to give piperazine protected compound.

The piperazine protected compound (2.6 g) and acetaldehyde (1.7 g) in methanol (25 ml) is cooled to 0°. Sodium cyanoborohydride (0.62 g) is added in one portion. The cooling bath is removed and the mixture is permitted to warm to 30°. The mixture is stirred at 20°–25° for 2 hr. The methanol is removed under reduced pressure and the residue is partitioned between methylene chloride and a saturated sodium bicarbonate solution. The phases are separated and the organic phase is washed with saturated sodium bicarbonate solution, saline, dried over magnesium sulfate and concentrated under reduced pressure to give an oil. The oil is purified by HPLC on silica gel, MS (M$^+$) 334.

The oil (2.1 g), aqueous hydrochloric acid (3N, 42 ml) and ethyl acetate (57 ml) are stirred for 1 hr at 20°–25°. The mixture is cooled in ice, basified (pH=11) with potassium hydroxide (20%), the phases separated and the aqueous phase extracted again with ethyl acetate. The combined extracts are washed with saline, dried over magnesium sulfate, and concentrated under reduced pressure to give the title compound. NMR was in agreement.

PREPARATION A-60

4-[5-(Ethylamino)-6-(diethylamino)-2-pyrimidinyl]piperazine

A solution of di-t-butyldicarbonate (4.78 g) and methylene chloride (20 ml) is added to a mixture of 4-(5-amino-6-diethylamino)pyrimidinylpiperazine (4.97 g), methylene chloride (70 ml), triethylamine (3.33 ml) and dimethylaminopyridine (10 mg). The mixture is stirred overnight. Basic workup (sodium bicarbonate/methylene chloride/magnesium sulfate) and purification by flash chromatography (hexane/ethyl acetate; 2/1) gives the carbamate of 4-(5-amino-6-diethylamino)pyrimidinylpiperazine, MS (EI, relative percent) 350 (100), 251 (38), 207 (38) and 194 (89).

Sodium cyanoborohydride (0.300 g) is added to a solution of the carbamate (0.652 g), methanol (13 ml) and acetaldehyde (2.1 ml). The mixture is stirred for 1 week at 20°–25°. At two day intervals similar amounts of sodium cyanoborohydride and acetaldehyde are added. Concentration and basic workup (chloroform/sodium bicarbonate/magnesium sulfate) and purification by flash chromatography (hexane/ethyl acetate; 2/1) give the carbamate of the title compound, MS (EI, relative percent) 378 (100), 322 (21), 293 (43), 277 (18) and 249 (44).

The carbamate of the title compound (465 mg), ethyl acetate (9.5 ml) and hydrochloric acid (3N, 7 ml) are stirred at 20°–25° for 2 hr. Basic workup (chloroform/solid potassium hydroxide/magnesium sulfate) provide the title compound, NMR (CDCl$_3$) 1.06, 1.07, 2.98, 2.95 3.1, 3.25 and 3.35–3.45 δ.

PREPARATION A-61

4-[5-amino-6-(diethylamino)-2-pyrimidinyl]piperazine

A solution of diethylamine (4.0 ml) and acetonitrile (25 ml) is added dropwise over 40 min to a mixture of 4,6-dichloro-5-nitropyrimidine (7.5 g), acetonitrile (150 ml) and potassium carbonate (6.41 g) at 0°. The mixture is stirred for an additional 50 min at 0° and is then allowed to warm to 20°–25°. After 16 hr, the mixture is filtered, and the residue washed with acetonitrile (2×25 ml).

The crude filtrate, piperazine (25.8 g) and potassium carbonate (6.41 g) are combined and heated at reflux for 6 hr. After cooling to 20°–25°, basic workup (sodium bicarbonate/chloroform/magnesium sulfate) and purification by flash chromatography (chloroform/methanol/ammonium hydroxide; 200/10/1) an oil is obtained which solidifies upon standing to give 5-nitro-6-diethylamino-4-piperazinylpyrimidine, MS (CI, relative percent) 281 (100), 265 (13), 249 (18) and 234 (71).

5-Nitro-6-diethylamino-4-piperazinylpyrimidine (0.980 g), ethanol (25 ml) and palladium/carbon (10%, 0.25 g) are exposed to hydrogen (50 psi) for 24 hr. The mixture is filtered and the residual solids are washed with chloroform/ethanol. The combined filtrates are concentrated under reduced pressure. Basic workup (aqueous potassium hydroxide, chloroform, magnesium sulfate) provided a solid mp 58°–59°; NMR (CDCl$_3$) 1.11, 2.95–3.05, 3.15–3.4 and 3.29 δ.

PREPARATION S-1

21-Bromo-17α-hydroxypregna-4,9-diene-3,20-dione

See U.S. Pat. No. 4,041,055 (Ex 59).

PREPARATION S-2

21-Bromo-17α-hydroxypregn-4-ene-3,11,20-trione

[26987-70-2], see J. Chem. Soc. B., 4, 748 (1970).

PREPARATION S-3

11α,17α,21-Trihydroxypregn-4-ene-3,20-dione 21-tosylate

Tosyl chloride (freshly recrystallized, 3.48 g) in pyridine (10 ml) is added dropwise over 15 min to a solution of 11α,17α,21-trihydroxypregn-4-ene-3,20-dione (British Patent 1,100,505, 6 g) in pyridine (90 ml) precooled to 0°. The resulting mixture is stirred for 1.5 h at 0° and 1 h at 20°–25°. The mixture is quenched with aqueous sodium bicarbonate and ethyl acetate. Aqueous workup (chloroform, magnesium sulfate) provides the crude tosylate. Tosylate can be purified by flash chromatography on silica gel eluting with chloroform/methanol (15/1).

PREPARATION S-4

11α,21-Dihydroxypregn-4-ene-3,20-dione

[600-67-9], see U.S. Pat. No. 4,013,688.

PREPARATION S-5

21-Bromo-17α-hydroxypregn-4-ene-3,20-dione

[20380-17-0], see U.S. Pat. No. 4,500,461.

PREPARATION S-6

21-Bromopregn-4-ene-3,11,20-trione

[51297-00-8], see U.S. Pat. No. 3,983,111.

PREPARATION S-7

21-Hydroxypregna-4,9(11),16-triene-3,20-dione

[24510-86-9], see Tetrahedron Lett. 25, 2581 (1984).

PREPARATION S-8

21-Iodopregna-4,9(11)-diene-3,20-dione

[95288-91-8].

PREPARATION S-9

21-Bromopregn-4-ene-3,20-dione

[26987-66-6], see J. Org. Chem., 50, 81 (1985).

PREPARATION S-10

17β-Carboxy-17α-hydroxyandrost-4-ene-3-one

17α-21-Dihydroxypregna-4-ene-3,20-dione (7.41 g) in methanol (150 ml) at 0° is added over 5 min to a solution of sodium metaperiodate (6.02 g) in water (50 ml). The pH is adjusted to about 6.3 using dilute sulfuric acid. The mixture is stirred at about 45° for 3 h. The mixture is then diluted with water (110 ml), stirred in an ice bath for 30 min and filtered. The solids are washed with ice cold water (200 ml) and air dried. The solids are dissolved in acetone (200 ml) and heated on a steam bath for 15 min and filtered. The filtrate is concentrated and dissolved in water (100 ml) containing sodium hydroxide (50%, 1.4 ml, pH greater than 11). The mixture is washed with toluene (2×300 ml) and the toluene backwashed with water (100 ml). The aqueous extracts are combined and filtered. The filtrate is acidified with acetic acid (20%, 10 ml) to form a slurry. The slurry is stirred at 20°–25° overnight and filtered to obtain the title compound, NMR (CDCl$_3$) 1.85, 3.20 δ; MS 332 (M$^+$ at m/e); UV (ethanol) $\iota_{max}$=241 mμ (ε=15,800).

PREPARATION S-12

11β,17α-Dihydroxy-21-iodo-6α-methylpregna-1,4-diene-3,20-dione

[85847-53-6], see J. Pharm. Soc., 74, 365 (1985).

PREPARATION S-13

21-Bromo-11β,17α-dihydroxypregna-1,4-diene-3,20-dione

[55706-94-0], see U.S. Pat. No. 3,856,956.

PREPARATION S-14

17α-Hydroxy-21-iodo-16α-methylpregna-1,4,9(11)-triene-3,20-dione

[23776-76-3], see U.S. Pat. No. 3,455,968.

PREPARATION S-15

17α,21-dihydroxy-6α-methylpregna-1,4,9(11)-triene-3,20-dione

[93269-35-3], see West German DE 3,322,120.

PREPARATION S-16

17α,21-Dihydroxypregna-1,4,9(11)-triene-3,20-dione 21-tosylate

A mixture of prednisolone (100 g), triethylamine (38.8 ml), acetic anhydride (26.3 ml), methylene chloride (1200 ml) and 4-[dimethylamino]pyridine is stirred under nitrogen at 20°–25° for 3 days. The reaction mixture is diluted with ether and filtered through celite 521. The solid is dissolved with THF and concentrated. Additional 21-acetate is obtained from the mother liquor.

The 21-acetate (63.25 g), pyridine (70 ml) and DMF (200 ml) is cooled in an ice/acetone bath to less than 0°. In a separate flask sulfur dioxide gas is bubbled for 7 min into pyridine (77.99 g) in an ice bath. The sulfur dioxide solution is poured into the steroid mixture. This mixture is stirred at 0°–5° and N-bromosuccinimide (30.93 g) is added slowly keeping the temperature less than 5°. The reaction mixture is left at less than 0° for 2 h under nitrogen. The mixture is diluted with water and partitioned with methylene chloride. The phases are separated, the organic phase is washed with dilute aqueous hydrochloric acid, water dilute aqueous sodium bicarbonate and again with water. The organic phase is dried over sodium sulfate and concentrated. The crude material is triturated with ether and filtered to give the Δ$^{9(11)}$-21-acetate. Sodium methoxide (1.7 ml) (4.1N in methanol) is added to a stirred mixture of the Δ$^{9(11)}$-21-acetate (17.03 g) in methanol (550 ml) under nitrogen at 20°–25°. After about 15 min, a precipitate forms. The reaction is left for 3 h and then diluted with cold water and filtered to give the $\Delta^{9(11)}$-21-hydroxy compound which can be purified by HPLC if desired.

The $\Delta^{9(11)}$-21-hydroxy steroid (0.58 g) p-toluenesulfonyl chloride (0.42 g) and pyridine (25 ml) are stirred under nitrogen at 20°–25° for 24 h. After 24 h additional tosyl chloride (0.42 g) is added. The mixture is partitioned between methylene chloride and water, the organic phase is separated, washed with saturated aqueous sodium bicarbonate, twice with saline and dried over sodium sulfate. The mixture is concentrated without heat to give the title compound.

PREPARATION S-17

17α-Hydroxy-21-iodopregna-1,4-diene-3,11,20-trione

[55786-16-8], see J. Med. Chem., 28, 171 (1985).

PREPARATION S-18

21-Bromopregna-1,4-diene-3,20-dione

[97453-07-1], see Bull. Chem. Soc. Jpn. 58, 981 (1985).

PREPARATION S-19

11α,17α,21-Trihydroxypregna-1,4-diene-3,20-dione 21-tosylate

A solution of tosyl chloride (1.16 g) and pyridine (3 ml) is added dropwise over 10 min to a solution of 11α-17α-21-trihydroxypregna-1,4-diene-3,20-dione (600-90-8, West German DE 2,715,854, 2.0 g) and pyridine (30 ml) at 0°. The resulting mixture is stirred for 1.5 h at 0° and 1.5 h at 20°–25°. The mixture is quenched with ethyl acetate (8 ml) and aqueous sodium bicarbonate (20 ml). Aqueous workup (chloroform, magnesium sulfate) provides the title compound.

PREPARATION S-21

17α,21-Dihydroxypregna-1,4,9(11)-triene-3,20-dione

[10184-69-7], see West German DE 3,322,120.

PREPARATION S-22

21-Iodo-16α-methylpregna-1,4,9(11)-triene-3,20-dione

A solution of 150 g (0.41 mol) of 21-hydroxypregna-1,4,9(11),16-tetraene-3,20-dione 21-acetate (U.S. Pat. No. 2,864,834, 150 g) and 90 ml of 1.9 molar copper propionate in THF is cooled in an ice acetone bath. Methyl magnesium chloride (1.96 molar in THF, 240 ml) is added dropwise over 30 minutes. The reaction is checked by TLC (1:1 ethyl acetate/hexane on silica gel). Additional Grignard reagent can be added if the reaction is not complete. After 1 h, the reaction is quenched with 375 ml of 25% concentrated hydrochloric acid in methanol. The reaction is partitioned between water and toluene. The organic phase is washed with water, filtered through sodium sulfate and concentrated. The residue is crystallized from ether and hexane. The crystals are triturated with ether to give the desired (16α-methyl) Michael addition product.

This is stirred in 1500 ml of methanol and is treated with 5.0 ml of 25% sodium methoxide in methanol for 30 min. The mixture is partitioned between methylene chloride and sodium bicarbonate. The organic phase is washed with sodium bicarbonate, filtered through sodium sulfate and concentrated. The residue is crystallized from ether to give a 21-hydroxy steroid.

72.45 g of this material is dissolved in 145 g of pyridine and is treated with 86.94 g of tosyl chloride. Reaction temperature is 0°. After 15 min, the reaction is warmed to 20°–25°. After 1 h, the reaction is cooled in an ice bath and 30 g of lactic acid is added to destroy excess tosyl chloride. The mixture is partitioned between methylene chloride and aqueous sodium bicarbonate. The organic phase is washed with bicarbonate, filtered through sodium sulfate and concentrated. The residue is chromatographed on silica gel (1:1 ethyl acetate/hexane) to give a pale solid which is dissolved in 500 ml of acetone. Sodium iodide (40 g) is added and the mixture is stirred for 4.25 h. The mixture is partitioned between methylene chloride and water. The organic phase is washed with water, filtered through sodium sulfate and concentrated. The residue is chromatographed (1:1 ethyl acetate-hexane) to give a single spot material which is crystallized from ether to give the title compound, NMR (CDCl$_3$) 0.67, 1.05, 1.4, 0.8–3, 2.75, 5.25, 5.55, 6.05, 6.20, 6.35 and 7.2 δ.

PREPARATION S-23

11α-Hydroxy-21-iodo-16α-methylpregna-1,4-diene-3,20-dione

A mixture of 11α-hydroxy-16α-methylprogesterone (3.44 g) and DDQ (1.1 eq) in 250 ml of benzene is heat under reflux for about 20 hours. The organic layer is then washed (2× 100 ml 1N sodium hydroxide, 2×100 ml water and 1×100 ml saline) and the aqueous layers backwashed (2×100 ml ether). The extracts are dried and concentrated to give a foam which is chromatographed on silica gel (300 g), eluting with 8 l of 10% acetone—methylene chloride and 20% acetone—methylene chloride. The appropriate fractions (200 ml) are pooled and concentrated to give the $\Delta^{1,4}$-steroid.

The $\Delta^{1,4}$-steroid (1.7 g) in methanol (5 ml) and carbon tetrachloride (10 ml) is mixed with 0.17 ml of 10% calcium chloride in methanol and stirred for 0.25 hours. Calcium oxide (1.73 g) is added, followed by slow addition (4 hours) of a suspension of 2.44 g of iodine in 3.9 ml of 10% calcium chloride in methanol. The mixture is stirred for an additional 0.5 hours, then is filtered through celite (wet with methanol). The filtrate is concentrated to give a gum. Chromatography on silica gel (600 g) and elution with 8 l of 10% and 4 l of 20% acetone-methylene chloride gives the title compound as a foam which is crystallized from acetone-hexane, mp 153°.

PREPARATION S-24

21-Iodo-16α-methylpregna-1,4-diene-3,20-dione

A mixture of 16α-methylprogesterone (792 mg), DDQ (575 mg) and benzene are heated at reflux for 28 hr, after 20 hr additional DDQ (70 mg) is added. After refluxing, the mixture is cooled to 20°–25°, filtered followed by basic workup (ether—potassium carbonate—magnesium sulfate) to give 16α-methylpregna-1,4-diene-3,20-dione.

16α-Methylpregna-1,4-diene-3,20-dione (2.26 g), carbon tetrachloride (15 ml), methanol (7.3 ml) and calcium chloride in methanol (10%, 0.24 ml) are combined and stirred for 15 min at 20°–25°. Calcium oxide (2.50 g) is added and the mixture stirred an additional 5 min. A mixture of iodine (3.54 g), calcium chloride (10%, 5.4 ml) and methanol (2.4 ml) is added dropwise over 1 hr to the steroid mixture. After an additional 30 min the mixture is diluted with methylene chloride (100 ml), filtered through celite and concentrated. The residue is partitioned between methylene chloride and water, the phases are separated, the organic phase is washed with sodium sulfite, dried over magnesium sulfate and then concentrated to give the title compound, NMR (CDCl$_3$) 0.7, 0.9, 1.2, 5.25, 5.35, 6.0, 6.2 and 7.0 δ.

PREPARATION S-25

17α,21-Dihydroxy-16β-methyl-5α-pregn-9(11)-ene-3,20-dione

[80163-64-0], see U.S. Pat. No. 4,336,200.

PREPARATION S-26

21-Bromo-3α,17α-dihydroxy-5β-pregnane-11,20-dione

[95044-38-5]

PREPARATION S-28

11β-Hydroxypregn-5-ene-21-al 3-ethylene glycol ketal

Following the general procedure of PREPARATION S-29 and making non-critical variations but starting with 21-carboxy-11β-hydroxypregna-5,17(20)-diene 3-ethylene glycol ketal 21-methyl ester, the title compound is obtained, MS (electron impact) 374, 273 and 99; m.p. 162°–166°.

PREPARATION S-29

Pregna-5,9(11)-dien-21-al 3-ethylene glycol ketal

21-Carboxypregna-5,9(11),17(20)-triene 3-ethylene glycol ketal 21-methyl ester (4.0 g) in dry THF (60 ml) is added to a stirred suspension of lithium aluminum hydride (1.58 g) in anhydrous ether (50 ml) cooled in an ice/water bath. After the addition is complete the cooling bath is removed and the mixture stirred at 20°–25° for 18 hr. The mixture is cooled in an ice/water bath and sequentially treated dropwise with ethyl acetate (10 ml), water (1.6 ml), sodium hydroxide (15%, 1.6 ml) and water (4.8 ml). Additional ether (50 ml) is added. The mixture is filtered and the solids washed with ethyl acetate. The combined wash and filtrate is concentrated under reduced pressure to about 25 ml. This material is flash chromatographed in silica gel (150 g) with hexane/ethyl acetate (1/1) as the eluent. The appropriate fractions are pooled and concentrated to give the title compound, m.p. 161°–162°; MS (electron impact) 356 and 99.

PREPARATION S-30

17α,21-Dihydroxypregn-4-ene-3,11,20-trione 21-mesylate

A mixture of cortisone (10 g), pyridine (100 ml) and methanesulfonyl chloride (3.2 g) is stirred at 20°–25° for one hr. The bulk of the pyridine is removed under reduced pressure and the residue dissolved in methylene chloride (300 ml). The mixture is washed with cold hydrochloric acid (10%, 200 ml) and dried over sodium sulfate. The solvent is removed under reduced pressure to give the title compound, NMR (CDCl$_3$) 0.74, 1.09, 1.18, 0.8–2.5, 2.99, 4.2 and 6.73 δ.

PREPARATION S-31

21-Hydroxy-20-methylpregn-4-en-3-one 21-mesylate

A solution of glacial acetic acid (40 ml) is treated with portions of sodium borohydride (0.83 g) below 20°. After the final portion is added, the mixture is stirred at 20° for 5 min. 3-Oxo-bisnor-4-cholen-22-al (3.28 g) is added over a period of 5 min. The mixture is stirred at 20°–25° for 2 h. Excess acetic acid is removed at 45° to leave a residue. The residue is diluted with a 50/50 mixture of water and 10% aqueous sodium hydroxide. This aqueous mixture is extracted with methylene chloride which is washed with 10% aqueous sodium hydroxide followed by water and saline, then dried over sodium sulfate and concentrated to give 21-hydroxy- 20-methylpregn-4-en-3-one.

A solution of methanesulfonyl chloride (0.37 ml) in methylene chloride (10 ml) is added dropwise to an ice cold solution of the 20-hydroxy steroid (1.44 g) and triethylamine (0.7 ml) in methylene chloride (40 ml). The mixture is stirred for 30 min and then poured into ice cold dilute sodium bicarbonate. The layers are separated, the organic phase is washed with water, dried over sodium sulfate and concentrated to give the title compound.

PREPARATION S-32

Δ$^1$-Bisnoraldehyde

A solution of bisnoraldehyde (15.5 g) in benzene (500 ml) and DDQ (17 g) is refluxed under nitrogen for 16 h. The mixture is cooled to 20°–25° and the solids filtered using a celite pact funnel. The filtrate is concentrated to a foaming residue which is dissolved in chloroform and flash chromatographed on silica gel eluting with ethyl acetate-chloroform (30/70). The appropriate fractions are pooled and concentrated to give the title compound, NMR (CDCl$_3$) 0.79, 1.12, 1.23, 0.8–2.5, 6.0, 6.21, 7.05 and 9.56 δ.

PREPARATION S-33

21-Hydroxypregna-1,4,9(11),16-tetraene-3,20-dione 21-mesylate

A mixture of 21-hydroxypregna-1,4,9(11),16-tetraene-3, 20-dione (9 g) and triethylamine (3.35 g) in methylene chloride (200 ml) at 0° under nitrogen is treated dropwise with a mixture of methanesulfonyl chloride (3.5 g) in methylene chloride (50 ml) over a period of 30 min. The mixture is stirred in ice for 1–1.2 h and then allowed to warm to 20°–25° over 2 h. Additional methanesulfonyl chloride (1.75 g) and triethylamine (2.3 ml) is added and the mixture stirred for 30 min at 20°–25°. The mixture is stored at less than 0° overnight. The mixture is washed with cold dilute sodium bicarbonate, water, 2% hydrochloric acid, saline and dried over sodium sulfate and concentrated to give the title compound, NMR (CDCl$_3$) 0.93, 1.43, 1.5–2.75, 3.21, 5.10, 5.6, 6.05, 6.25, 6.8 and 7.20 δ.

PREPARATION S-34

6α-Fluoro-17α,21-dihydroxy-16β-methylpregna-4,9(11)-diene-3,20-dione 21-tosylate The 21-tosylate is prepared from the corresponding 21-hydroxy steroid (U.S. Pat. No. 4,088,537, Preparation 3) by the procedure of PREPARATION S-19.

PREPARATION S-35

21-Iodo-16,α,17α-dimethylpregna-1,4,9(11)-triene-3,20-dione

A mixture of 21-hydroxypregna-1,4,9(11),16-tetraene-3,20-dione 21-acetate (150 g) and copper propionate (1.9M in THF, 90 ml) is cooled in an ice acetone bath. Methyl magnesium chloride (1.96M in THF, 240 ml) is added dropwise for 30 min. The reaction is monitored by TLC (ethyl acetate/hexane, 1/1). Additional Grignard reagent is added if needed. After 1 hr the reaction is quenched with methyl iodide (100 g) in THF (200 ml). The reaction mixture is partitioned between water and toluene. The phases separated, the organic phase is washed with water, filtered thru sodium sulfate and concentrated. The residue is crystallized from ether and hexane. The crystals are triturated with ether to give the Michael addition product with a 17α-methyl group.

This material (144.3 g) is stirred in methanol (1500 ml) and is treated with sodium methoxide (25%, 5 ml) for 30 min. The mixture is then partitioned between methylene chloride and sodium bicarbonate. The organic phase is separated, washed with sodium bicarbonate, filtered thru sodium sulfate and concentrated. The residue is crystallized from ether. This material is dissolved in pyridine (145 G) and treated with tosyl chloride (86.94 g). The reaction temperature is 0°. After 15 min, the reaction is warmed to 20°–25°. After 1 hr the reaction mixture is cooled in an ice bath and lactic acid (30 g) is added. The mixture is partitioned between methylene chloride and aqueous sodium bicarbonate. The organic phase is washed with bicarbonate, filtered thru sodium sulfate and concentrated. The residue is chromatographed on a silica gel column, elution with ethyl acetate/hexane (1/1). The appropriate fractions are pooled and concentrated to a solid, which is dissolved in acetone (500 ml). Sodium iodide (40 g) is added and the mixture stirred for 4.25 hr. The mixture is partitioned between methylene chloride and water. The organic phase is washed with water, filtered thru sodium sulfate and concentrated. The residue is chromatographed, eluting with ethyl acetate/hexane (1/1). The appropriate fractions are pooled and concentrated to give one spot material which is crystallized from ether to give the title compound.

PREPARATION S-37

21-Bromo-3,17α-dihydroxy-19-norpregna-1,3,5(10)-trien-20-one 3-methylether

See, JACS 80, 2226 (1958) for the 21-acetate.

PREPARATION S-38

3β-Hydroxy-21-iodo-16α-methylpregn-5-en-20-one

See, Helv Chim Acta 42, 2043 (1959) and Rev Romaine Chim 9, 147 (1964).

PREPARATION S-39

3α-Hydroxy-21-iodo-16α-methyl-5α-pregnan-20-one

A mixture of 3α-hydroxy-16α-methyl-5α-pregnan-20-one (21 g) methanol (80 ml), carbon tetrachloride (40 ml), THF (120 ml), calcium oxide (25 g) and calcium chloride in methanol (10%, 3 ml) is stirred at 25°–30°. A solution of iodine (20 g) in calcium chloride (10%, 70 ml) is added to the steroid mixture over 1 hr. The mixture is stirred an additional 2 hr at 30°, filtered through a pad of filter aid, and the filtrate concentrated under reduced pressure to an oil. The oil is dissolved in methylene chloride and flash chromatographed over silica gel (100 g) eluting with methylene chloride/ethyl acetate (4/1). The appropriate fractions are pooled, concentrated and the residue triturated with ether to give the title compound.

PREPARATION S-40

3β-Hydroxy-21-iodo-16α-methyl-5α-pregnan-20-one

Following the general procedure of PREPARATION S-39 and making non-critical variations but starting with the 3β-hydroxy isomer, the title compound is obtained.

PREPARATION S-41

21-Hydroxy-16α-methylpregna-1,4,6,9(11)-tetraene-3,20-dione

Following the general procedure, of Campbell and Babcock, JACS 81, 4069 (1959), a mixture of 21-hydroxy-16α-methylpregna-4,9(11)-diene-3,20-dione (21.05 g) and chloranil (15.0 g) in t-butanol (800 ml) is refluxed for 2 hr under nitrogen. The mixture is cooled and concentrated under reduced pressure at 35°. The residue is dissolved in a minimum amount of methylene chloride and chromatographed over neutral alumina (32–63 μm, 100 g) eluting with methylene chloride. The appropriate fractions are pooled and concentrated. The residue is dissolved in ethyl acetate/hexane (4/1) and washed repeatedly with aqueous sodium hydroxide (5%), then with water, dried over sodium sulfate and concentrated under reduced pressure to a solid. The solid is crystallized from acetone-hexane to give the $\Delta^{4,6}$-steroid, mp 125°.

The $\Delta^{4,6}$-steroid (3.81 g) and DDQ (2.84 g) in benzene is refluxed for 17 hr in a nitrogen atmosphere. The mixture is cooled, filtered and the precipitate is washed with methylene chloride. The combined filtrates are concentrated under induced pressure. The residue is dissolved in ethyl acetate/hexane (4/1) and washed repeatedly with aqueous sodium hydroxide (5%), then with water, dried over sodium sulfate and concentrated under reduced pressure to give the $\Delta^1$-steroid.

The $\Delta^1$-steroid (1.93 g) in methanol (20 ml) at 20°–25° in a nitrogen atmosphere is treated with a sodium methoxide in methanol solution (25%, 0.75 ml) for 10 min. The reaction is then diluted with ice-cold water (60 ml) and extracted with methylene chloride. Saline is added to the aqueous phase and again extracted with methylene chloride. The combine methylene chloride extracts are washed with water, dried over sodium sulfate, and concentrated under reduce pressure to give the title compound.

PREPARATION S-42

16α-Methyl-17β-(1-oxo-[4-mesyloxy]butyl)androsta-4,9(11)-dien-3-one

Step (A) 16α-Methylandrosta-4,9(11)-dien-3-one 17β-carboxylate

Periodic acid (14.73 g) is dissolved in water (162 ml) and is then slowly added to a stirred solution of 21-hydroxy-16α-methylpregna-4,9(11)-diene-3,20-dione (10.34 g) in methanol (675 ml) at 26°–28°. The reaction mixture is stirred for an additional hour at 20°–25° and then concentrated under reduced pressure with concurrent addition of water (1675 ml). The mixture is cooled and filtered to give 9.94 g of 16α-methylandrosta-4,9(11)-dien-3-one 17β-carboxylate.

Step (B) 16α-Methylandrosta-4,9(11)-dien-3-one 17β-carboxylate methyl ester

Methyl iodide (7.9 ml) is added to a solution of 16α-methylandrosta-4,9(11)-dien-3-one 17β-carboxylate (7.9 g) and diisopropylethylamine (17.5 ml) in acetonitrile (175 ml). The mixture is allowed to stand at 20°–25° for 2 hr and then a second addition of amine (9 ml) and iodide (4 ml) is made. The mixture is allowed to stand overnight at 20°–25° and then concentrated under reduced pressure. The residue is partitioned (water and methylene chloride) and the extract is concentrated and chromatographed on silica gel (750 g). Elution is performed with acetone/methylene chloride (2–5%/98–95%). The appropriate fractions are pooled and concentrated to give the title compound, m.p. 127.5° (acetone-hexane)

Step (C) 16α-Methylandrosta-5,9(11)-dien-3-one 17β-methoxy 3-ethylene ketal

A mixture of 1.47 g of the methyl ester, step (B), ethylene glycol (2.9 ml) and p-TSA hydrate (29 mg) in benzene (60 ml) is heated under reflux (water separator) for 4.5 hr. The mixture is then cooled and washed with aqueous bicarbonate, water and saline. The dried extracts are concentrated and the residue is chromatographed on silica gel. Elution is performed with acetone/methylene chloride (1/99, containing 0.1% triethylamine). The appropriate fractions are pooled and concentrated to give the 3-ketal.

Step (D) 16α-Methyl-17β-(1-oxo-[4-tetrahydropyranyloxy]butyl)-androsta-5,9(11)-dien- 3-one 3-ethylene ketal A mixture of 3.86 g of the 3-ketal, Step (C), in THF (75 ml) is stirred at −78° and organolithium reagent (1.25M, 10 ml) [prepared from adding a solution of 2-(3-chlorochloropropoxy)tetrahydro- 2H-pyran (11.6 g) in ether (100 ml) slowly (3.5 hr) to lithium (11 g, 0.6% sodium) in ether (150 ml) at −10°] is added. The mixture is allowed to warm slowly to 25°, is stirred overnight and then poured into ice and aqueous ammonium chloride. The mixture is extracted with ethyl acetate and concentrated to give 16α-methyl-17β-(1-oxo-[4-tetrahydropyranyloxy] butyl)-androsta-5,9(11)-dien-3-one 3-ethylene ketal.

Step (E) 16α-Methyl-17β-(1-oxo-[4-hydroxy]butyl)-androsta-4,9(11)-dien-3-one

16α-Methyl-17β-(1-oxo-[4-tetrahydropyranyloxy]butyl)-androsta-5,9(11)-dien-3-one 3-ethylene ketal, step (D), is dissolved in acetone (90 ml) and hydrochloric acid (1N, 10 ml) and allowed to stand at 20°–25° for several hours. Following addition of potassium bicarbonate (1N, 25 ml), the mixture is concentrated and extracted with ethyl acetate. The concentrate is chromatographed on silica gel eluting with acetone/methylene chloride. The appropriate fractions are pooled and concentrated to give 16α-methyl-17β-(1-oxo-[4-hydroxy]butyl)androsta- 4,9(11)-dien-3-one.

Step (F) 16α-Methyl-17β-(1-oxo-[4-mesyloxy]butyl)androsta-4,9(11)-dien-3-one

A solution of 16α-methyl-17β-(1-oxo-[4-hydroxy]butyl)androsta-4,9(11)-dien-3-one (5.0 g) in pyridine (38 ml) is cooled to −5° and methanesulfonyl chloride (1.7 ml) is added slowly. After two hr at −5° the reaction mixture is poured onto ice and hydrochloric acid (12N). The mixture is extracted with chloroform and concentrated. The concentrate is chromatographed on silica gel eluting with acetone/methylene chloride, the appropriate fractions are pooled and concentrated to give 16α-methyl-17β-(1-oxo-[4-mesyloxy]butyl)androsta-4,9(11)-dien-3-one.

PREPARATION S-43

21—Carboxy-3,3-dihydroxypregna-5,17(20)-trans-dien-11-one 3,3-dimethyl ether 21-methyl ester

EXAMPLE 0

2,4-Bis(diethylamino]-6-piperazinopyrimidine and 2-diethylamino- 4,6-dichloropyrimidine A solution of 2,4,6-trichloropyrimidine (34.0 g) in methylene chloride (400 ml) is stirred at 0°. To this solution is added dropwise a mixture of diethylamine (73 g) and triethylamine (50 g). The mixture is warmed to 20°–25° and is then refluxed for 1 hr. The mixture is partitioned between methylene chloride and aqueous sodium bicarbonate. The phases are separated and the organic phase is dried over sodium sulfate and concentrated. The concentrate is chromatographed on silica gel (400 g) eluting with 10% ethyl acetate/hexane to give the faster moving 2,4-bis(diethylamino)-6-chloropyrimidine and the slower moving 2-diethylamino- 4,6-dichloropyrimidine. The dichloro product is converted to the bis(diethylamino)-6-chloro pyrimidine by warming in pyridine with diethylamine.

A solution of the 2,4-[bis(diethylamino)]-6-chloropyrimidine (32.25 g) and piperazine (65 g) in pyridine (250 ml) is refluxed for 24 hr and then heated in a Parr bomb at 170° for 20 hr. The mixture is partitioned between ether and aqueous potassium carbonate. The phases are separated and the organic phase is washed with saline, dried over sodium sulfate and concentrated. The concentrate is chromatographed on silica gel (methylene chloride to 4% methanol/methylene chloride) to give 2,4-[bis-diethylamino]-6-piperazinopyrimidine, NMR (CDCl$_3$) 1.0–1.3, 2.75–3.0, 3.25–3.65 and 4.95 δ.

EXAMPLE 1

17α-Hydroxy-21-[4-(2-pyridinyl)-1-piperazinyl]-pregna-4,9(11)-diene- 3,20-dione (I)

17α-Hydroxy-21-iodopregna-4,9(11)-diene-3,20-dione (4.53 g) is stirred in acetonitrile (50 ml) with 1-(2-pyridinyl)piperazine (1.63 g) and potassium carbonate (1.34 g) at 60° for 5 hr and at 20°–25° for 17 hr. The reaction is partitioned between ether and aqueous sodium bicarbonate. The organic phase is washed with saline, dried over sodium sulfate and concentrated. The residue is chromatographed on silica gel with methanol/methylene chloride (4/96) to give the title compound.

EXAMPLE 2

17α-Hydroxy-21-[4-(2-pyridinyl)-1-piperazinyl]-pregna-4,9(11)-diene- 3,20-dione methanesulfonate 17α-Hydroxy-21-[4-(2-pyridinyl)-1-piperazinyl]pregna-4,9(11)-diene-3,20-dione (Example 1) is dissolved in methanol and treated with methane sulfonic acid (0.224 g). The solution is concentrated and the residue is crystallized from hot methanol and ethyl acetate to give a first crop of the title compound. A second crop of the mesylate is isolated.

EXAMPLE 3

17α-Hydroxy-21-[4-(2-pyridinyl)-1-piperazinyl]-pregna-4,9(11)-diene- 3,20-dione hydrogen chloride salt (I)

21-Bromo-17α-hydroxypregna-4,9(11)-dione-3,20-dione (26.0 g) is stirred in acetonitrile (800 ml) with 1-(2-pyridinyl)piperazine (13 g) and potassium carbonate (9 g). The reaction is stirred at 20°–25°. After 20 hr, another 4 g of the amine is added. After 5 hr, the reaction is concentrated and the residue partitioned between methylene chloride and aqueous sodium bicarbonate. The phases are separated, the organic phase is dried over sodium sulfate and concentrated. The residue is chromatographed on silica gel (methylene chloride to 2% methanol/methylene chloride) to give a product which is crystallized from hot ethyl acetate to a solid. The solid is dissolved in ethyl acetate and methanol and treated with excess hydrochloric acid/ether. The crystals are filtered and then triturated with hot ethyl acetate to give the title compound.

EXAMPLE 4

21-[4-[2-Amino-6-(diethylamino)-4-pyrimidinyl]-1-piperazinyl]-17α-hydroxypregna-4,9(11)-diene-3,20-dione (I)

2-Amino-4-diethylamino-6-chloropyrimidine (1.55 g) and dry piperazine (3.5 g) are heated at 100° in ethylene glycol (20 ml) for 4 hr. The mixture is partitioned between methylene chloride and aqueous sodium bicarbonate, the phases are separated, the organic phase is dried with sodium sulfate and concentrated. The residue is chromatographed on silica gel (ethyl acetate to 1% methanol/ethyl acetate to 20% methanol/1% ammonia/ethyl acetate) to yield 1.29 g of the pure amine product. This material is stirred at reflux in acetonitrile (60 ml) with 21-bromo-17α-hydroxypregna-4,9(11)-diene-3,20-dione and potassium carbonate (0.8 g) for 7 hr then at 20°–25° overnight. The reaction mixture is partitioned between methylene chloride and aqueous sodium bicarbonate. The phases are separated and the organic phase is dried with sodium sulfate and concentrated. The residue is chromatographed on silica gel eluting with methanol in methylene chloride (4/96) to give an oil with an NMR consistent with the desired product. The product is dissolved in ethyl acetate and treated with methane sulfonic acid (325 mg). The solid which insults is triturated with ether to give the title compound.

EXAMPLE 5

17α-Hydroxy-21-[4-hydroxy-4-(4-trifluoromethyl)-phenyl-1-piperidinyl]-pregna-4,9(11)-diene-3,20-dione (I)

4-Hydroxy-4-([4-trifluoromethyl]phenyl)piperidine (6.81 g) is stirred at reflux in acetonitrile (200 ml) with 21-bromo-17α-hydroxypregna-4,9(11)-diene-3,20-dione (11.39 g) and with potassium carbonate (3.83 g) for 8 hr. The reaction is concentrated, the mixture is partitioned between methylene chloride and aqueous sodium bicarbonate, the phases are separated, the organic phase is dried with sodium sulfate and concentrated. The concentrate is chromatographed on silica gel eluting with methanol/methylene chloride (2/98) to give the title compound which is crystallized from hot ethyl acetate.

EXAMPLE 6

17α-Hydroxy-21-[4-(2-furanylcarbonyl)-1-piperazinyl]-pregna-4,9(11)-diene- 3,20-dione (I)

STEP A 17α-Hydroxy-21-(1-piperazinyl)pregna-4,9(11)-diene-3,20-dione

A mixture of 21-bromo-17α-hydroxypregna-4,9(11)-diene-3,20-dione (40.0 g) piperazine (16.80 g) and potassium carbonate (13.2 g) are heated at 70° in acetonitrile (800 ml) for 2.5 hr. The mixture is partitioned between methylene chloride and aqueous sodium bicarbonate, the phases are separated, the organic phase is dried with sodium sulfate and concentrated. The residue is recrystallized from hot ethyl acetate to give 17α-hydroxy-21-(1-piperazinyl)pregna-4,9(11)-diene-3,20-dione.

STEP B 17α-Hydroxy-21-[4-(2-furonylcarbonyl)-1-piperazinyl]pregna-4,9(11)-diene- 3,20-dione (I)

17α-Hydroxy-21-(1-piperazinyl)pregna-4,9(11)-diene-3, 20-dione (Example 6A, 3.91 g) triethylamine (1.5 g) in dry tetrahydrofuran (120 ml) is reacted at 0° with 2-furoyl chloride (1.24 g). After the addition, the reaction is stirred under nitrogen for 2 days at 20°–25°. The mixture is partitioned between methylene chloride and aqueous sodium bicarbonate, the phases are separated, the organic phase is dried with sodium sulfate and concentrated. The concentrate is chromatographed on silica gel eluting with methanol/methylene chloride (3/97) to give the title compound which is recrystallized from hot ethyl acetate.

EXAMPLE 7

17α-Hydroxy-21-(4-(benzo[b]thien-2-yl)-1-piperazinyl)pregna-4,9(11)-diene- 3,20-dione (I)

2-Chlorobenzothiazole (5.00 g), is heated in alcohol (75 ml) with 3.05 g piperazine (3.05 g) for 20 hr. 1% mixture is partitioned between methylene chloride/ether and aqueous sodium bicarbonate, the phases are separated, the organic phase is dried with sodium sulfate and concentrated to give 2-piperazinobenzothiazole which is reacted at 70° in acetonitrile (200 ml) with 21-bromo-17α-hydroxypregna-4,9(11)-diene-3,20-dione (7.45 g) and potassium carbonate (2.44 g) for 6 hr and at 20°–25° for 3 days. The mixture is partitioned between methylene chloride and aqueous sodium bicarbonate, the phases are separated, the organic phase is dried with sodium sulfate and concentrated. The concentrate is chromatographed on silica gel eluting with methanol/methylene chloride (6/94) to give the title compound which is recrystallized from ethyl acetate.

EXAMPLE 8

17α-Hydroxy-21-[4-(2-pyrimidinyl)-1-piperazinyl]-pregna-4,9(11)-diene-3,20-dione (I)

A mixture of 2-chloropyrimidine (10.0 g) and piperazine (16 g) in alcohol (120 ml) is stirred for 21 hr. The mixture is partitioned between methylene chloride and aqueous sodium bicarbonate, the phases are separated and the organic phase is dried with sodium sulfate and concentrated to give 2-pyrimidinyl piperazine. The 2-pyrimidinyl piperazine (4.64 g) is stirred at 70° in acetonitrile (200 ml) with 21-bromo-17α-hydroxypregna-4,9(11)-diene-3,20-dione (11.52 g) and potassium carbonate (3.75 g) for 1.5 hr and at 20°–25° for 2 days. The mixture is partitioned between methylene chloride and aqueous sodium bicarbonate, the phases are separated and the organic phase is dried with sodium sulfate and concentrated. The concentrate is chromatographed on silica gel eluting with 4 to 6% methanol/ methylene chloride. The appropriate fractions are pooled and concentrated to give the title compound which is crystallized from ethyl acetate.

EXAMPLE 9

17α-Hydroxy-21-[4-(2-carboxybenzoyl)-1-piperazinyl]pregna-4,9(11)-diene-3,20-dione (I) also known as
2-[[4-(17-hydroxy-3,20-dioxopregna-4,9(11)-dien-21-yl)-1-piperazinyl]-carbonyl]-benzoic acid 17α-Hydroxy-21-(1-piperazinyl)pregna-4,9(11)-diene-3, 20-dione (Example 6A, 5.11 g) and phthalic anhydride (1.84 g) are stirred in acetonitrile (100 ml) and methylene chloride (100 ml) for 4 hr. The mixture is concentrated and the residue is recrystallized from ethyl acetate and ether to give the product which is chromatographed on silica gel (4% methanol/methylene chloride to 8%/1% acetic acid/methylene chloride) to give the title compound.

EXAMPLE 10

17α-Hydroxy-21-[4-[[(3-chlorophenyl)amino]-carbonyl)-1-piperazinyl]
pregna-4,9(11)-diene-3,20-dione (I)

17α-Hydroxy-21-(1-piperazinyl)pregna-4,9(11)-diene-3, 20-dione (EXAMPLE 6A, 5.00 g) is treated in DMF (20 ml) with m-chlorophenyliso-cyanate (1.94 g) for 3 days. The mixture is poured into water (200 ml). After 1 hr, the liquid is decanted. The solid is dissolved in methylene chloride and is extracted with aqueous sodium bicarbonate. The phases are separated and the organic phase is dried over sodium sulfate and concentrated. The concentrate is chromatographed on silica gel (3% methanol in methylene chloride to 4%) to give the title compound which is crystallized from hot ethyl acetate.

EXAMPLE 11

17α-Hydroxy-21-[4-(2-methoxyphenyl)-1-piperazinyl]pregna-4,9(11)-diene-3,20-dione (I)

A mixture of 2-chloro-6-methoxypyridine (20 g) and piperazine (32.9 g) with potassium carbonate (20.1 g) in water (50 ml) is stirred at 100° for 24 hr. The mixture is partitioned between methylene chloride and aqueous sodium bicarbonate, the phases are separated and the organic phase is dried over sodium sulfate and concentrated. The concentrate is dissolved in ether. The organic phase is extracted with hydrochloric acid (10%). The aqueous phase is washed with ether, neutralized with sodium hydroxide (10%) and extracted with methylene chloride. The organic phase is dried over sodium sulfate and concentrated to give 2-piperazino- 6-methoxypyridine. This material is stirred in acetonitrile (100 ml) with 21-bromo-17α -hydroxypregna-4, 9(11)-diene-3,20-dione (3.01 g) and potassium carbonate (1.3 g) at 20°–25° for 16 hr. The mixture is partitioned between methylene chloride and aqueous sodium bicarbonate. The phases are separated and the organic phase is dried over sodium sulfate and concentrated. The concentrate is chromatographed over silica gel (2% methanol in methylene chloride to 4%) to give the free base of the title compound which is 92% pure by HPLC. This material is dissolved in ethyl acetate and treated with methane sulfonic acid (0.606 g). The salt is filtered and recrystallized from methanol and ethyl acetate to give the title compound.

EXAMPLE 12

17α-Hydroxy-21-[4-[2,6-bis(dimethylamino)-4-pyrimidinyl]-1 -piperazinyl]pregna-4,9(11)-diene-3,20-dione hydrochloride salt (I)

A solution of dimethylamine (16.6 g) in water (66.4 ml), triethylamine (20 g), and 1,3,5-trichloropyrimidine (8.30 g) in alcohol (100 ml) is stirred at 20°–25° for 2 hr. The mixture is stored at 0° overnight. Another 2 g of dimethyl amine solution (25%) is added and the reaction mixture is stirred at 20°–25° for 2 hrs more. The mixture is partitioned between methylene chloride and aqueous sodium bicarbonate. The phases are separated, the organic phase is dried over sodium sulfate and concentrated. The concentrate is chromatographed over silica gel with ethyl acetate/hexane (10/90) to give 2,4-bis[dimethylamino]-6-chloropyrimidine. This bis adduct is heated with piperazine (2.60 g) in alcohol (100 ml) for 1 hr. The mixture is partitioned between methylene chloride and aqueous sodium bicarbonate. The phases are separated and the organic phase is dried over sodium sulfate and concentrated. The residue is crystallized from ether and hexane to give the desired $C_{21}$ substituent. This material (3.00 g) is stirred in acetonitrile (250 ml) with 21-bromo-17α-hydroxypregna-4,9(11)-diene-3,20-dione (5.97 g) and potassium carbonate (1.98 g) for 20 hr. The mixture is partitioned between methylene chloride and aqueous sodium bicarbonate. The phases are separated and the organic phase is dried over sodium sulfate and concentrated. The concentrate is chromatographed over silica gel (methylene chloride to 4% methanol/methylene chloride) to give the corresponding free amine base of the title compound. This compound is dissolved in ethyl acetate and treated with excess hydrogen chloride/ether. The product is filtered, washed with ether and triturated with hot ethyl acetate to give the title compound.

EXAMPLE 13

17α-Hydroxy-21-[4-(3,6-dimethylpyrazinyl)-1-piperazinyl]pregna-4,9(11)-diene- 3,20-dione monomethane sulfonate hydrate (I)

A solution of 3-chloro-2,5-dimethylpyrazine (5.00 g), 1-benzylpiperazine (6.20 g) and triethylamine (3.5 g) in ethylene glycol (25 ml) is heated at 100° for 10 hr. Another 3 g of the benzylpiperazine is added and the mixture is stirred at 100° for another 20 hr. The mixture is partitioned between methylene chloride and aqueous sodium bicarbonate. The phases are separated, the organic phase is dried over sodium sulfate and concentrated. The concentrate is chromatographed on silica gel (10% to 30% ethyl acetate in hexane) to give the free base of the 21-amino substituent. The material is dissolved in ethanol (100 ml) and methanol (2 ml) which is saturated with hydrogen chloride gas. This mixture is hydrogenated for 17 hr over palladium on carbon (10%, 900 mg) at 50 psi. The mixture is filtered through celite, and the solids are washed with methanol. The organic phase is concentrated to give the 21-amino substituent. This material is reacted in dry acetonitrile (200 ml) with 21-bromo-17α-hydroxypregna-4,9(11)-diene- 3,20-dione (3.60 g) and potassium carbonate (1.18 g) at 60° for 23 hr. The reaction mixture is partitioned between methylene chloride and aqueous sodium bicarbonate. The phases are separated and the organic phase is dried over sodium sulfate and concentrated. The concentrate is chromatographed on silica gel (2% methanol in methylene chloride) to give the free base of the desired product. This compound is converted to the mono methane sulfonic acid salt with methanesulfonic acid (0.56 g) in alcohol. The salt is crystallized from methanol/ethyl acetate to give the title compound.

EXAMPLE 14

21-[4-[2-(Diethylamino)-6-(1-pyrrolidinyl)-4-pyrimidinyl]-pyrimidinyl]
-1-piperazinyl]-17α-hydroxypregna-4,9(11)-
diene-3,20-dione dihydrochloride hydrate (I)

A solution of 2-diethylamino-4-piperazino-6-chloro-pyrimidine (4.10 g) in pyrrolidine (4.10 g) is heated for 12 hr at 100°, then concentrated. The concentrate is partitioned between aqueous sodium bicarbonate and methylene chloride. The phases are separated, the organic phase is dried and concentrated to give 2-diethylamino-4-piperazino-6-pyrrolidino-pyrimidine. A solution of this amine (4.01 g), 21-bromo-17α-hydroxypregna-4,9(11)-diene-3,20-dione (5.41 g), and potassium carbonate (1.75 g) are stirred in acetonitrile (200 ml) for 19 hr. The reaction mixture, is partitioned between methylene chloride and aqueous sodium bicarbonate. The phases are separated and the, organic phase is dried over sodium sulfate and concentrated. The concentrate is chromatographed on silica gel (methylene chloride to 4% methanol/methylene chloride) to give the free base corresponding to the title compound. An ethyl acetate solution of this compound is converted to the hydrochloride salt with ether/hydrochloric acid to give the title compound.

EXAMPLE 15

17α-Hydroxy-21-[4-[2-(diethylamino)-6-(4-methyl-1-piperazinyl)-4-pyrimidinyl]
-1-piperazinyl]pregna-4,9(11)-diene-3,20-dione hydrochloride hydrate (I)

A solution of 2-diethylamino-4-[4-methylpiperazinol-6-piperazinopyrimidine (prepared from 2-diethylamino-4,6-dichloropyrimidine of EXAMPLE 0, 4.14 g), 21-bromo-17α-hydroxypregna- 4,9(11)-diene-3,20-dione (4.85 g) and potassium carbonate (1.58 g) in acetonitrile (200 ml) is stirred at 20°–25° for 24 hr. The mixture is partitioned between methylene chloride and aqueous sodium bicarbonate. The phases are separated and the organic phase is concentrated and chromatographed on silica gel (methylene chloride to 2% methanol/methylene chloride) to give the free base of the title compound which is converted to the hydrochloride salt.

EXAMPLE 16

17α-Hydroxy-21-[4-[2,6-bis(diethylamino)
pyrimidinyl]-1-piperazinyl]pregna-
4,9(11)-diene-3,20-dione dihydrochloride hydrate
(I)

A solution of 2,4-bis(diethylamino]-6-piperazinopyrimidine (EXAMPLE 0, 6.47 g), 21-bromo- 17α-hydroxypregna-4,9(11)-diene-3,20-dione (11.48 g) and potassium carbonate (3.75 g) in acetonitrile (500 ml) is stirred at 20°–25° for 24 hr. The mixture is partitioned between methylene chloride and aqueous sodium bicarbonate. The phases are separated and the organic phase is concentrated and chromatographed on silica gel (methylene chloride to 4% methanol/methylene chloride) to give the free base corresponding to the title compound which is converted to the hydrochloride salt.

EXAMPLE 17

17α-Hydroxy-21-[4-[2-(diethylamino)-6-(1-piperidinyl)-4-pyrimidinyl]-1
-piperazinyl]pregna-4,9(11)-diene-3,20-dione
hydrochloride hydrate (I)

A solution of 2-diethylamino-4,6-dichloropyrimidine (EXAMPLE 0, 4.00 g) in piperidine (6.00 g) is heated at 80° for 20 min. The mixture is stirred at 20°–25° for 15 hr and then partitioned between methylene chloride and aqueous sodium bicarbonate. The phases are separated and the organic phase is dried over sodium sulfate and concentrated. The NMR is consistent with the mono-piperidine adduct. The residue and piperazine (8 g) are refluxed in pyridine (100 ml) for 6 hr. The reaction mixture is partitioned between methylene chloride and aqueous potassium carbonate. The phases are separated and the organic phase is dried over sodium sulfate, concentrated and chromatographed on silica gel (methylene chloride to 6% methanol-1% ammonium hydroxide-methylene chloride) to give 2-diethylamino-4-piperidino-6-piperazinopyrimidine.

This amine (2.04 g) is treated with 21-bromo-17α-hydroxypregna-4,9(11)-diene-3,20-dione (2.5 g) and potassium carbonate (0.87 g) in acetonitrile (150 ml) at 20°–25° for 67 hr. The reaction mixture is partitioned between methylene chloride and aqueous sodium bicarbonate. The phases are separated and the organic phase is dried over sodium sulfate, concentrated and chromatographed on silica gel (50/50 ethyl acetate-hexane to 82/20) to give the free base corresponding to the product. This compound is dissolved in ethyl acetate and converted to the hydrochloride salt which is triturated with ether and dried to give the title compound.

EXAMPLE 18

21-[4-[2,6-Bis(diethylamino)-4-pyrimidinyl]-1-piperazinyl]-17α-hydroxy-
16α-methylpregna-1,4,9(11)-triene-3,20-dione
hydrochloride hydrate (I)

17α-Hydroxy-21-iodo-16α-methylpregna-1,4,9(11)-triene-3,20-dione (2.60 g) is reacted with 2,4-[bis-diethylamino]-6-piperazinopyrimidine (1.39 g) all potassium carbonate (0.75 g) in acetonitrile (50 ml) at 20°–25° for 42 hr. The reaction mixture is partitioned between methylene chloride and aqueous potassium carbonate. The phases are separated and the organic phase is dried over sodium sulfate, concentrated and chromatographed on silica gel (methylene chloride to 2% methanol) to give the free base corresponding to the product. This compound is converted to the hydrochloride salt by use of ethyl acetate/etherhydrochloric acid.

EXAMPLE 19

17α-Hydroxy-21-[4-[2,6-bis(4-methyl-1-piperazinyl)A-pyrimidinyl]-1-piperazinyl]
-pregna-4,9(11)-diene-3,20-dione methanesulfonate
hydrate (I)

Trichloropyrimidine is added in portions to an ice cooled solution of N-methylpiperazine (40 g) in alcohol (200 ml). The mixture is then heated at 60° for 2 hr. The mixture is concentrated and chromatographed on silica gel with 2 to 5% methanol in methylene chloride to give 2,4-bis-[4-methylpiperazinol-6-chloropyrimidine. This material is heated at 130° in water (30 ml) with piperazine (32 g) in a Parr bomb for 20 hr. The product is partitioned between methylene chloride and aqueous sodium carbonate. The phases are separated and the organic phase is dried over sodium sulfate and concentrated to give 2,4-bis[1-(4-methylpiperazino)]-6 -piperazinopyrimidine. This triamine is stirred in acetonitrile (200 ml) with 21-bromo-17α-hydroxypregna- 4,9(11)-diene-3,20-dione (7.18 g) and potassium carbonate (2 g) for 20 hr. The mixture is partitioned between methylene chloride and aqueous sodium bicarbonate. The phases am separated and the organic phase is concentrated and chromatographed on silica gel (methylene chloride to 5% methanol and 0.5% ammonium hydroxide/methylene chloride) to give the free base corresponding to the title compound. The free base is dissolved in ethyl acetate and treated with methane sulfonic acid (2.22 g). The product is triturated with ether to give the title compound, bubbled at 110° without obvious decomp.

Following the general procedure of EXAMPLES 1-6A, 7, 8, 11–19, 83 and 126 and making non-critical variations but starting with (a) the corresponding $C_{17}$-terminally substituted halo (chlorine, bromine or iodine), methanesulfonate (mesylate) or toluenesulfonate (tosylate) steroid of the desired amino substituted steroid (XI) and (b) the corresponding free amine of the amino substituent of the desired amino substituted steroid (XI), the amino substituted steroids (XI) of EXAMPLES 20–27, 29, 30, 33–55, 58–101, 105, 109–111 and 113–132 are obtained.

Following the general procedure of EXAMPLE 31 (11-esters) and making non-critical variations, the amino substituted steroids (XI) of EXAMPLES 28 and 32 are obtained.

Following the general procedure of EXAMPLE 103 (where n=0) and making non-critical variations but starting with (a) the corresponding 17-acid of the desired amino substituted steroid (XI) and (b) the corresponding free amine of the amino substituent at $C_{20}$ of the desired amino substituted steroid (XI), the amino substituted steroids (XI) of EXAMPLES 56 and 57 are obtained.

Following the general procedure of EXAMPLE 104 (Z is not =O) and making non-critical variations but starting with (a) the corresponding 21-aldehyde or equivalent thereof of the desired amino substituted steroid (XI), and (b) the corresponding free amine of the amino substituent of the desired amino substituted steroid (XI), the amino substituted steroids (XI) of EXAMPLES 106–108 and 112 are obtained:

| EXAMPLE | Amino Substituted Steroid Product (XI) |
|---|---|
| 20 | 17α-hydroxy-21-[4-(2-pyridinyl)-1-piperazinyl-pregn-4-ene-,3,11,20-trione |
| 21 | 11β,17α-dihydroxy-6α-methyl-21-[4-(2-pyridinyl)-1-piperazinyl]pregna-1,4-diene-3,20-dione |
| 22 | 17α-hydroxy-21-[4-(6-methoxy-2-pyridinyl)-1-piperazinyl]pregna-4,9(11)-diene-3,20-dione monomethanesulfonate |
| 23 | 11αa,17α-dihydroxy-21-[4-(2-pyridinyl)-1-piperazinyl]pregn-4-ene-3,20-dione |
| 24 | 17α-hydroxy-21-[methyl[2-(methyl-2-pyridinylamino)ethyl]-amino pregna-4,9(11)-diene-3,20-dione dihydrochloride |
| 25 | 11↑,17α-dihydroxy-21-[4-(2-pyridinyl)-1-piperazinyl]pregna-1,4-diene-3,20-dione dihydrochloride |
| 26 | 11β,17α-dihydroxy-21-[4-(4-fluorophenyl)-1-piperazinyl]pregna-1,4-diene-3,20-dione dihydrochloride |
| 27 | 11β,17α-dihydroxy-21-[4-(4-methoxyphenyl)-1-piperazinyl]pregna-1,4-diene-3,20-dione dihydrochloride |

EXAMPLE 28

11α,17α-Dihydroxy-21-[4-(2-pyridinyl)-1-piperazinyl]pregn-4-ene-3,20-dione 11-(3,3-dimethyl-1-butyrate dihydrochloride Following the general procedure of EXAMPLE 31 and making noncritical variations and starting with the steroid of EXAMPLE 23 but using the appropriate acid chloride the title compound is obtained.

| EXAMPLE | Amino Substituted Steroid Product (XI) |
|---|---|
| 29 | 21-[4-(4-fluorophenyl)-1-piperazinyl]-11α,17α-dihydroxypregn-4-ene-3,20-dione dihydrochloride |
| 30 | 11α,17α-dihydroxy-21-[4-(4-methoxyphenyl)-1-piperazinyl]pregn-4-ene-3,20-dione dihydrochloride |

EXAMPLE 31

11α,17α-Dihydroxy-21-[4-(2-pyridinyl)-1-piperazinyl]pregn-4-ene-3,20-dione 11-(2-furanylcarbonyl) dihydrochloride (I)

11α,17α-Dihydroxy-21-[4-(2-pyridinyl)-1-piperazinyl] pregn-4-ene-3,20-dione (EXAMPLE 23, 312 mg) and triethylamine (0.144 ml) are added to a mixture of dimethylaminopyridine (126 mg), furoyl chloride (0.7 ml) and chloroform (3.0 ml). The mixture is stirred for six days at 20°–25°. Basic workup (chloroform—5% sodium hydroxide, potassium carbonate) and purification by flash chromatography on silica gel eluting with chlorofom/methanol (15/1), pooling and concentrating the appropriate fractions gives the title compound.

EXAMPLE 32

11α,17α-dihydroxy-21-[4-(4-methoxyphenyl)-1-piperazinyl]pregn-4-ene-3,20-dione 11-(3,3-dimethyl-1-butyrate) dihydrochloride (I)

Following the general procedure of EXAMPLE 31 and making non-critical variations but starting with the steroid of EXAMPLE 30 and using the acid chloride of EXAMPLE 28 the title compound is obtained.

| EXAMPLE | Amino Substituted Steroid Product (XI) |
|---|---|
| 33 | 11β,17α-dihydroxy-21-[4-(4-methoxyphenyl)-1-piperazinyl]-6α-methylpregna-1,4-diene-3,20-dione dihydrochloride |
| 34 | 11β,17α-dihydroxy-21-[[2-(3,4-dimethoxy-phenyl)ethyl]amino]-6α-methylpregna-1,4-diene-3,20-dione hydrochloride |
| 35 | 17α-hydroxy-16α-methyl-21-[4-(2-pyridinyl)-1-piperazinyl]pregna-1,4,9(11)-triene-3,20-dione |
| 36 | 11α-hydroxy-21-[4-(2-pyridinyl)-1-piperazinyl]-pregn-4-ene-3,20-dione dihydrochloride |
| 37 | 17α-hydroxy-21-[[2-(3,4-dimethoxy-phenyl)ethyl]- |

| EXAMPLE | Amino Substituted Steroid Product (XI) |
|---|---|
| 38 | [3,4,5-trimethoxyphenyl)methyl]amino]pregna-4,9(11)diene-3,20-dione hydrochloride |
| | 17α-hydroxy-21-[[2-(2,4-dimethoxyphenyl)-1-methylethyl]amino]pregna-4,9(11)-diene-3,20-dione hydrochloride |
| 39 | 21-[1-(2-carboxy)piperidinyl]-17α-hydroxypregna-4,9(11)-diene-3,20-dione |
| 40 | 21-[4-(2-pyridinyl)-1-piperazinyl]pregn-4-ene-3,20-dione dihydrochloride hydrate |
| 41 | 17α-hydroxy-21-[4-(2-methoxyphenyl)-1-piperazinyl]pregn-4-ene-3,20-dione dihydrochloride hydrate |
| 42 | 17α-hydroxy-21-[4-[3,4-dimethoxyphenyl)methyl-1-piperazinyl]pregna-4,9(11)-diene-3,20-dione dihydrochloride hydrate |
| 43 | 17α-hydroxy-21-[4-(2-pyridinyl)-1-piperazinyl]pregn-4-ene-3,20-dione dihydrochloride hydrate |
| 44 | 17α-hydroxy-16β-methyl-21-[4-(2-pyridinyl)-1-piperazinyl]-5α-pregn-9(11)-ene-3,20-dione dihydrochloride hydrate |
| 45 | 21-[4-(2-pyridinyl)-1-piperazinyl]pregn-4-ene-3,11,20-trione hydrochloride hydrate |
| 46 | 17α-hydroxy-6α-methyl-21-[4-(2-pyridinyl)-1-piperazinyl]pregna-1,4,9(11)triene-3,20-dione (E)-2-butenodioate salt |
| 47 | 17α-hydroxy-6α-methyl-21-[4-[2,6-bis(1-pyrrolidinyl)-4-pyrimidinyl]-1-piperazinyl]pregna-1,4,9(11)-triene-3,20-dione (E)-2-butenodioate salt |
| 48 | 17α-hydroxy-21-[4-[(5-methyl)-4-phenyl-4H-1,2,4-triazol-3-yl]-1-piperazinyl]pregna-4,9(11)-diene-3,20-dione dihydrochloride hydrate |
| 49 | 21-[4-(2-pyridinyl)-1-piperazinyl]pregna-1,4,9(11)-triene-3,20-dione hydrochloride hydrate |
| 50 | 21-[4-[2,6-bis(diethylamino)4-pyrimidinyl]-1-piperazinyl]-11α,17α-dihydroxypregn-4-ene-3,20-dione hydrochloride |
| 51 | 17α-hydroxy-21-[[2-(3,4-dimethoxyphenyl)ethyl]-4-(dimethylamino)-phenyl]methyl]amino]pregna-4,9(11)-3,20-dione hydrochloride |
| 52 | 21-[4-[2-amino-5-(1-pyrrolidinyl)phenyl]-1-piperazinyl]-17α-hydroxypregna-4,9(11)-diene-3,20-dione hydrochloride |
| 53 | 21-[4-[2,6-bis(diethylamino)4-pyrimidinyl]-1-piperazinyl]-17α-hydroxypregn-4-ene-3,20-dione |
| 54 | 17α-hydroxy-21-[4-(2-pyridinylmethyl)-1-piperazinyl]-pregna-4,9(11)-diene-3,20-dione (E)-2-butenedioate 1:1 salt |
| 55 | 17α-hydroxy-21-[4-[[4-(dimethylamino)phenyl]methyl]-1-piperazinyl]-pregna-4,9(11)-diene-3,20-dione (E)-2-butenedioate 1:1 salt |
| 56 | 17βcarboxy-17α-hydroxyandrost-4-en-3-one 4-(2-pyridinyl)-1-piperazinyl amide |
| 57 | 17βcarboxy-17α-hydroxyandrost-4-en-3-one 1-[2,6-bis(diethylamino)-4-pyrimidinyl]-1-piperazinyl] amide |
| 58 | 21-[4-(2-pyridinyl)-1-piperazinyl]pregna-4,9(11),16-triene-3,20-dione hydrochloride with trichloromethane hydrate (4:8:3:4) |
| 59 | 17α-hydroxy-21-[4-(2-pyridinyl)-1-piperazinyl]pregna-1,4-diene-3,11,20-trione hydrochloride hydrate (2:1:3) |
| 60 | 17α-hydroxy-21-[4-[4,6-bis(2-propenylamino)-1,3,5-triazin-2-yl]-1-piperazinyl]pregna-4,9(11)-diene-3,20-dione dihydrochloride hydrate |
| 61 | 17α-hydroxy-21-[4[(3-hydroxy-2-pyridinyl)methyl]-1-piperazinylpregna-4,9(11)-diene-3,20-dione (E)-2-butenedioate (1:1) salt |
| 62 | 17α-hydroxy-21-[4-[6-(1-pyrrolidinyl)-2-pyridinyl]-1-piperazinyl]pregna-4,9(11)-diene-3,20-dione (E)-2-butenedioate (1:1) salt |
| 63 | 21-[4-[2,6-bis(diethylamino)-4-pyrimidinyl]-1-piperaz-inyl]-17α-hydroxy-6α-methylpregna-1,4,9(11)-triene-3,20-dione (E)-2-butenedioate (1:1) salt |
| 64 | 17α-hydroxy-21-[4-[2,6-bis(1-pyrrolidinyl)-4-pyrimidinyl]-1-piperazinyl]-pregna-4,9(11)-diene-3,20-dione (E)-2-butenedioate (1:1) salt |
| 65 | 21-[4-(2-pyridinyl)-1-piperazinyl]pregna-1,4-diene-3,20-dione (E)-2-butenedioate (1:1) salt |
| 66 | 11α,17α-dihydroxy-21-[4-(2-pyridinyl)-1-piperazinyl]pregna-1,4-diene-3,20-dione (E)-2-butenedioate (1:1) salt |
| 67 | 17α-hydroxy-21-[[(3,4-dihydroxyphenyl)methyl][2-(3,4-dimethoxyphenyl)ethyl]amino]pregna-4,9(11)-diene-3,20-dione (E)-2-butenedioate (1:1) salt |
| 68 | 21-[4-[3-amino-6-(diethylamino)-2-pyridinyl]-1-piperazinyl]-17α-hydroxypregna-4,9(11)-diene 3,20-dione dihydrochloride |
| 69 | 21-[4-[2,6-bis(diethylamino)-4-pyrimidinyl]-1-piperazinyl]-11α-hydroxypregn-4-ene-3,20-dione dihydrochloride |
| 70 | 21-[4-[2,6-bis(diethylamino)4-pyrimidinyl]-1-piperazinyl]-11α,17α-dihydroxypregn-4-ene-3,20-dione dihydrochloride |
| 72 | 21-[4-[4,6-bis(2-propenylamino)-1,3,5-triazin-2-yl]-1-piperazinyl]pregn-4-ene-3,11,20-trione dihydrochloride |
| 73 | 17α-hydroxy-16α-methyl-21-[4-[2,6-bis-(1-pyrrolidinyl)-4-pyrimidinyl]-1-piperazinyl]pregna-1,4,9(11)-triene-3,20-dione (E)-2-butenedioate (1:1) salt |
| 74 | 17α-hydroxy-21-[4-[2,6-di-(1-pyrrolidinyl)-4-pyrimidinyl]-1-piperazinyl] pregna-1,4,9(11)-triene-3,20-dione dihydrochloride hydrate |
| 75 | 21-[4-[2,6-bis(diethylamino)4-pyrimidinyl]-1-piperazinyl]-17α-hydroxypregna-1,4,9(11)-triene-3,20-dione dihydrochloride hydrate |
| 76 | 21-[4-[4,6-bis(diethylamino)-2-pyrimidinyl]-1-piperazinyl]-17α-hydroxypregna-1,4,9(11)-triene-3,20-dione dihydrochloride hydrate |
| 77 | 16α-methyl-21-[4-(2-pyridinyl)-1-piperazinyl]pregna-1,4,9(11)-triene-3,20-dione |
| 78 | 11α-hydroxy-16α-methyl-21-[4-(2-pyridinyl)-1-piperazinyl]pregna-1,4-diene-3,20-dione |
| 79 | 16α-methyl-21-[4-(2-pyridinyl)-1-piperazinyl]pregna-1,4-diene-3,20-dione |
| 80 | 21-[4-[2,6-bis(diethylamino)-4-pyrimidinyl]-1-piperazinyl]-16α-methylpregna-1,4,9(11)-triene-3,20-dione |
| 81 | 21-[4-[2,6-bis(diethylamino)-4-pyrimidinyl]-1-piperazinyl]-11α-hydroxy-16α-methylpregna-1,4-diene-3,20-dione |
| 82 | 21-[4-[2,6-bis(diethylamino)-4-pyrimidinyl]-1-piperazinyl]-16α-methylpregna-1,4-diene-3,20-dione |

EXAMPLE 83

16α-Methyl-21-[4-(2,6-bis(1-pyrrolidinyl)-4-pyrimidinyl]-1-piperazinyl]pregna-1,4,9(11)-triene-3,20-dione dimethane-sulfonate A mixture of 4-(2,6-di-1-pyrrolidinyl-4-pyrimidinyl)-1-piperazine (PREPARATION A-22, 8.90 g), 21-iodo-16α-methylpregna-1,4,9(11)-triene-3,20-dione (PREPARATION S-22, 12.79 g) and 3.90 g of dry potassium carbonate in 200 ml of acetonitrile is stirred at 60° for 4 hr. The mixture is partitioned between aqueous potassium carbonate and methylene chloride. The organic phase is filtered through sodium sulfate and concentrated. The residue is chromatographed on silica gel (methylene chloride to 2% methanol/methylene chloride) to give a foam. This foam is crystallized from ethyl acetate, dissolved in ethyl acetate and treated with 5.16 g of methane sulfonic acid. The salt is triturated with ethyl acetate to give the title compound.

| EXAMPLE | Amino Substituted Steroid Product (XI) |
|---|---|
| 84 | 11α-hydroxy-16α-methyl-21-[4-[2,6-bis(1-pyrrolidinyl)-4-pyrimidinyl]-1-piperazinyl]pregna-1,4-diene 3,20-dione |
| 85 | 16α-methyl-21-[4-[2,6-bis(1-pyrrolidinyl)-4-pyrimidinyl]-1-piperazinyl]-pregna-1,4-diene-3,20-dione |
| 86 | 16α-methyl-21-[4-[2,6-bis(4-morpholino)-4-pyrimidinyl]-1-piperazinyl]-pregna-1,4,9(11)-triene-3,20-dione |
| 87 | 11α-hydroxy-16α-methyl-21-[4-[2,6-bis(4-morpholino)-4-pyrimidinyl]-1-piperazinyl]pregna-1,4-diene-3,20-dione |
| 88 | 16α-methyl-21-[4-[2,6-bis(4-morpholino)-4-pyrimidinyl]-1-piperazinyl]-pregna-1,4-diene-3,20-dione |
| 89 | 21-[4-[2,6-bis(allylamino)-4-pyrimidinyl]-1-piperazinyl]-16α-methylpregna-1,4,9(11)-triene-3,20-dione |
| 90 | 21-[4-[2,6-bis(allylamino)4-pyrimidinyl]-1-piperazinyl]-11α-hydroxy-16α-methylpregna-1,4-diene-3,20-dione |
| 91 | 21-[4-[2,6-bis(allylamino)-4-pyrimidinyl]-1-piperazinyl]-16α-methylpregna-1,4-diene-3,20-dione |
| 92 | 21-[[2-(diethylamino)ethyl]amino]-9α-fluoro-11β,17α-dihydroxypregna-1,4-diene-3,20-dione trihydrochloride trihydrate |
| 93 | 17α-hydroxy-21-(4-morpholino)-pregna4,9(11)-diene-3,20-dione (E)-2-butanedioate (1:1) salt |
| 94 | 21-[4-[2,6-bis(1-pyrrolidinyl)-4-pyrimidinyl]-1-piperazinyl]pregn-4-ene-3,11,20-trione dihydrochloride |
| 95 | 21-[4-[2,6-bis(1-pyrrolidinyl)-4-pyrimidinyl]-1-piperazinyl]pregna-4,9(11)-diene-3,20-dione dihydrochloride |
| 96 | 21-[4-[6-(diethylamino)-3-(dimethylamino)-2-pyridinyl]-1-piperazinyl]-17α-hydroxypregna-4,9(11)-diene-3,20-dione dihydrochloride |
| 97 | 21-[4-[2,6-di-(1-pyrrolidinyl)-4-pyrimidinyl]-1-piperazinyl]-pregna-1,4-diene-3,20-dione dihydrochloride |
| 98 | 21-[4-[2-pyridinyl)-1-piperazinyl]-pregna-4,9(11)-diene-3,20-dione dihydrochloride |
| 99 | 3α,17α-dihydroxy-21-[4-(2-pyridinyl)-1-piperazinyl]-5β-pregnane-11,20-dione dihydrochloride hydrate |
| 100 | 21-(4-acetyl-1-piperazinyl)-17α-hydroxypregna-4,9(11)-diene-3,20-dione |
| 101 | 17α-hydroxy-21-(4-methyl-1-piperazinyl)pregna-4,9(11)-diene-3,20-dione |
| EXAMPLE 103 | 17α-Hydroxy-17β-[[[(2-pyridinyl)methyl]amino]carbonyl]androst-4-en-3-one (1) |

17α-Hydroxyl-17βcarboxyandrost-4-en-3-one in dry methylene chloride is reacted with DCC and HOBT at 20°–25° for 48 hr. (2-Pyridinyl)methylamine is added and the mixture stirred at 20°–25° for 8 hr. The mixture is washed with sodium bicarbonate, water and saline, dried and concentrated. The concentrate is flash chromatographed on silica gel eluting with ethyl acetate. The appropriate fractions are pooled and concentrated to give the title compound, high resolution mass spectroscopy 422.2585.

EXAMPLE 104

21-[4-(2,6-Bis(1-pyrrolidinyl)-4-pyrimidinyl)-1-piperazinyl]pregna- 4,9(11)-dien-3-one hydrochloride (I)

A mixture of pregna-5,9(11)-dien-21-al 3-ethylene glycol ketal (PREPARATION S-29, 0.6 g), 4-(2,6-di-1-pyrrolidinyl-4-pyrimidinyl)-1-piperazine (PREPARATION A-22, 0.5 g) and methanol (50 ml) are, stirred at 20°–25° for 1 hr. Sodium cyanoborohydride (0.12 g) is added to the mixture and the resulting mixture is stirred at 20°–25° for 18 hr. The methanol is removed under reduced pressure and the solids are washed twice with cold water and air dried. This material is triturated with ether to give a solid. This solid is stirred with acetone (20 ml) and hydrochloric acid (6N, 2 ml) for 1 hr at 20°–25°. The acetone is removed under reduced pressure and the residue is distributed between chloroform (50 ml) and sodium hydroxide (10%, 50 ml). The phases are separated and the aqueous phase is extracted with chloroform (50 ml). The organic phases are combined and dried over sodium sulfate and the organic solvent removed under reduced pressure to give an oil. The oil is flashed chromatographed on silica gel (100 g) eluting with chloroform/ethyl acetate (3/2), the appropriate reactions are pooled and concentrated to give the free base of the title compound. The free base is reacted with ethereal hydrochloric acid, the solids are collected, triturated with ether twice and dried under a stream of nitrogen to give the title compound.

EXAMPLE 105

21-[4-(2,6-Bis(4-morpholino)-4-pyrimidinyl)-1-piperazinyl]-17α-hydroxypregna-4,9(11)-diene-3,20-dione dihydrochloride, hydrate (I)

Following the general procedure of EXAMPLES 1-6A, 7, 8, 9–11 and 83 and making non-critical variations but starting with the amine of PREPARATION A-23 and the steroid of PREPARATION S-1, the title compound is obtained.

EXAMPLE 106

11β-Hydroxy-21-[4-(2-pyridinyl)-1-piperazinyl]-pregn4-en-3-one dihydrochloride (I)

Following the general procedure of EXAMPLE 104 and making non-critical variations but starting with the amine of PREPARATION A-6 and the steroid of PREPARATION S-28, the title compound is obtained

| EXAMPLE | Amino Substituted Steroid Product (XI) |
|---|---|
| 107 | 20-Methyl-21-[4-(2,6-bis(1-pyrrolidinyl)-4-pyrimidinyl)-1-piperazinyl]pregna-4-ene-3-one hydrochloride |
| 108 | 20-Methyl-21-[4-(2-pyridinyl)-1-piperazinyl]pregn-4-en-3-one |
| 109 | 16α-Methyl-21-[4-[2,6-bis(1-pyrrolidinyl)-4-pyrimidinyl]-1-piperazinyl]-pregna-1,4,9(11)-triene-3,20-dione-monomethanesulfonate monohydrate |
| 110 | 21-[4-(2,6-Bis(1-pyrrolidinyl)4-pyrimidinyl)-1-piperazinyl]-1α-cyanopregna-4,9(11)-dien-3-one-trihydrochloride, hydrate |
| 111 | 21-[4-(2,6-Bis(1-pyrrolidinyl)-4-pyrimidinyl)-1-piperazinyl]pregna-1,4,9(11)-triene-3,20-dione dihydrochloride |
| 112 | 21-[4-(2,6-Bis(1-pyrrolidinyl)-4-pyrimidinyl)-1-piperazinyl]-20-methylpregna-1,4-dien-3-one methanesulfonate, hydrate |
| 113 | 21-[4-(2,6-Bis(1-pyrrolidinyl)-4-pyrimidinyl)-1-piperazinyl]pregna-1,4,9(11),16-tetraene-3,20 dione methanesulfonate, hydrate |
| 114 | 21-[4-(4,6-Bis(1-pyrrolidinyl)-1,3,5-triazin-2-yl)-1-piperazinyl]-16α-methylpregna-1,4,9(11)-triene-3,20-dione dihydrochloride |
| 115 | 21-[4-[2-[4-[2,6-Bis(1-pyrrolidinyl)-4-pyrimidinyl]-1-piperazinyl]ethyl]-1-piperazinyl]-17α-hydroxypregna-4,9(11)-diene-3,20-dione hydrochloride |

-continued

| EXAMPLE | Amino Substituted Steroid Product (XI) |
|---|---|
| 116 | 21-[4-[2,6-Bis(4-morpholino)-4-pyrimidinyl]-1-piperazinyl]pregna-1,4-diene-3,20-dione dihydrochloride |
| 117 | 21-[4-[2,6-Bis(diethylamino)-4-pyrimidinyl]-1-piperazinyl]-6α-fluoro-17α-hydroxy-16β-methylpregna-4,9(11)-diene-3,20-dione dihydrochloride |
| 118 | 6α-Fluoro-17α-hydroxy-16β-methyl-21-[4-[2,6-bis(1-pyrrolidinyl)-4-pyrimidinyl]-1-piperazinyl]-pregna-4,9(11)-diene-3,20-dione dihydrochloride |
| 119 | 6α-Fluoro-17α-hydroxy-16β-methyl-21-[4-(2-pyridinyl)-1-piperazinyl]-pregna-4,9(11)-diene-3,20-dione dihydrochloride |
| 120 | 21-[4-[5,6-Bis(diethylamino)-2-pyridinyl]-1-piperazinyl]pregna-1,4-diene-3,20-dione dihydrochloride |
| 121 | 16α-Methyl-21-[4-[2,6-bis(1-pyrrolidinyl)-4-pyrimidinyl]-1-piperazinyl]-pregna-1,4-diene-3,20-dione dihydrochloride |
| 122 | 21-[4-[5,6-Bis(diethylamino)-2-pyridinyl]-1-piperazinyl]-16α-methylpregna-1,4,9(11)-triene-3,20-dione hydrochloride |
| 123 | 21-[4-(2,6-Bis(1-pyrrolidinyl)4-pyrimidinyl)-1-piperazinyl]-16α,17α-dimethylpregna-1,4,9(11)-triene-3,20-dione hydrochloride |
| 124 | 21-[4-[5,6-Bis(diethylamino)-2-pyridinyl]-1-piperazinyl]-16α,17α-dimethylpregna-1,4,9(11)-triene-3,20-dione hydrochloride |
| 125 | 3,17α-Dihydroxy-21-[4-[2,6-bis(1-pyrrolidinyl)-4-pyrimidinyl]-1-piperazinyl]-19-norpregna-1,3,5(10)-trien-20-one 3-methyl ether (E)-2-butenedioate 1:1 salt |
| EXAMPLE 126 | 3β-Hydroxy-16α-methyl-21-[4-[2,6-bis(1-pyrrolidinyl)-4-pyrimidinyl]-1-piperazinyl]pregn-5-en-20-one |

3β-Hydroxy-21-iodo-16α-methylpregn-5-en-20-one (10 g) is added all at once to 4-[2,6-bis(1-pyrrolidinyl)-4-pyrimidinyl]piperazine (16 g) in DMF (400 ml) at 65° and then concentrated to 50 ml under reduced pressure. The concentrate is added to sodium dihydrogen phosphate (0.3M, 400 ml) and ethyl acetate (500 ml). The pH is adjusted to 4.5 with 0.3M phosphoric acid. The ethyl acetate layer is separated and extracted with sodium dihydrogen phosphate (0.3M, 2×200 ml). The ethyl acetate extract is then washed with phosphoric acid (0.3M, 400 ml). The acid extract is stirred and the ph is adjusted to 3.5 with sodium hydroxide (10%). The resulting precipitate is filtered, washed with water (200 ml) and dried to give the title compound.

| EXAMPLE | Amino Substituted Steroid Product (XI) |
|---|---|
| 127 | 21-[4-[3-(Ethylamino)-2-pyridinyl]piperazinyl]-16α-methylpregna-1,4,9(11)-triene-3,20-dione hydrochloride |
| 128 | 21-[4-[6-(Diethylamino)-2-pyridinyl]piperazinyl]-16α-methylpregna-1,4,9(11)-triene-3,20-dione hydrochloride |
| 129 | 3,17α-Dihydroxy-21-[4-[2,6-bis(1-pyrrolidinyl)-4-pyrimidinyl]-1-piperazinyl]-19-norpregna-1,3,5(10)-trien-20-one (E)-2-butenedioate 1:1 salt |
| 130 | 3β-Hydroxy-16α-methyl-21-[4-[2,6-bis(1-pyrrolidinyl)-4-pyrimidinyl]-1-piperazinyl]-5α-pregnan-20-one |
| 131 | 3α-Hydroxy-16α-methyl-21-[4-[2,6-bis(1-pyrrolidinyl)-4-pyrimidinyl]-1-piperazinyl]-5α-pregnan-20-one |
| 132 | 16α-Methyl-21-[4-[2,6-bis(1-pyrrolidinyl)-4-pyrimidinyl]-1-piperazinyl]-pregna-1,4,6,9(11)-tetraene-3,20-dione |

EXAMPLE 133

3β-Hydroxy-16α-methyl-21-[4-[2,6-bis-(1-pyrrolidinyl)-4-pyrimidinyl]-1-piperazinyl]-5α-pregnan-20-one 3-Phosphate (IV)

A mixture of 3β-hydroxy-16α-methyl-21-[4-[2,6-bis(1-pyrrolidinyl)-4-pyrimidinyl]-1-piperazinyl]-5α-pregnan-20-one (IV, EXAMPLE 130, 1.7 g) in acetone (15 ml) is added dropwise to a mixture of phosphorus oxychloride (1.6 g) in pyridine (15 ml) and acetone (20 ml) is stirred at −5°. The resulting mixture is stirred at 0° for 1 hr the added to acetone/water (66%, 150 ml) at −10°. The mixture is stirred 15 min at 5°–10° and then concentrated under reduced pressure to 60 ml. The resulting solid is filtered, washed with water (50 ml) and dried. The dried product is dissolved in methylene chloride/ethanol (4/1, 50 ml), additional ethanol (50 ml) is added and the mixture concentrated to give the title compound.

EXAMPLE 134

3β-Hydroxy-16α-methyl-21-[4-[2,6-bis(1-pyrrolidinyl)-4-pyrimidinyl]-1-piperazinyl]-5α-pregnan-20-one 3-phosphate dipotassium salt (IV)

3β-Hydroxy-16α-methyl-21-[4-[2,6-bis(1-pyrrolidinyl)-4-pyrimidinyl]-1-piperazinyl]-5α-pregnan-20-one 3-phosphate (IV, EXAMPLE 133) is dissolved in methylene chloride/ethanol (4/1, 50 ml) and potassium hydroxide (1N, 4.6 ml) is added. The mixture is concentrated to 50 ml under reduced pressure and the resulting solid filtered, washed with ethanol (25 ml) and dried to give the title compound.

EXAMPLE 135

3β-Hydroxy-16α-methyl-21-[4-[2,6-bis(1-pyrrolidinyl)-4-pyrimidinyl]-1-piperazinyl]pregn-5-en-20-one 3-phosphate (I)

Following the general procedure of EXAMPLE 133 and making non-critical variations but starting with 3β-hydroxy-16α-methyl-21-[4-[2,6-bis(1-pyrrolidinyl)-4-pyrimidinyl]-1-piperazinyl]pregn-5-en-20-one (EXAMPLE 126) the title compound is obtained.

EXAMPLE 136

3α—Hydroxy-16α-methyl-21-[4-[2,6-bis(1-pyrrolidinyl)-4-pyrimidinyl]-1-piperazinyl]-5α-pregnan-20-one 3-phosphate (IV)

Following the general procedure of EXAMPLE 133 and making non-critical variations but stirring with 3α-hydroxy-16α-methyl-21-[4-[2,6-bis(1-pyrrolidinyl)-4-pyrimidinyl]-1-piperazinyl]-5α-pregnan-20-one (IV, EXAMPLE 131) the title compound is obtained.

EXAMPLE 137

16α-Methyl-21-[4-[4,6-bis(2-pyridinyl)-1,3,5-triazin-2-yl]-1-piperazinyl]pregna-1,4,9(11)-triene-3,20-dione (I)

Following the general procedure of EXAMPLES 1-6A, 7, 8, 11–19, 83 and 126, and making non-critical variations but starting with 21-iodo-16α-methylpregna-1,4,9(11)-triene-3,20-dione (PREPARATION S-22) and 4-[4,6-bis(2-pyridinyl)-1,3,5-triazin-2-yl]piperazine (PREPARATION A-49) the title compound is obtained.

EXAMPLE 138

16α-Methyl-21-[4-[5,6-bis(2-pyridinyl)-1,2,4-triazin-3-yl]-1-piperazinyl] pregna-1,4,9(11)-triene-3,20-dione (I)

Following the general procedure of EXAMPLES 1-6A, 7, 8, 11–19, 83 and 126, and making non-critical variations but starting with 21-iodo-16α-methylpregna-1,4,9(11)-triene-3,20-dione (PREPARATION S-22) and 4-[5,6-bis(2-pyridinyl)-1,2,4-triazin-3-yl]-1-piperazine (PREPARATION A-50) the title compound is obtained.

EXAMPLE 139

16α-Methyl-17β-(1-oxo-4-[4-[2,6-bis(1-pyrrolidinyl)-4-pyrimidinyl]-1-piperazinyl]butyl)androsta-4,9(11)-dien-3-one methanesulfonate (I)

A mixture of 16α-methyl-17β-(1-oxo-[4-mesyloxy]butyl)androsta-4,9(11)-dien-3-one (PREPARATION S-42, 3.77 g), 4-[2,6-bis(1-pyrrolidinyl)-4-pyrimidinyl]piperazine (PREPARATION A-22, 3.02 g), potassium carbonate (0.58 g) sodium iodide (0.12 g) and acetonitrile (170 ml) is stirred and heated under reflux for about 7 hr. The mixture is allowed to cool and is concentrated. The residue is partitioned between methylene chloride and aqueous potassium bicarbonate and the extract is concentrated. The concentrate is chromatographed on silica gel eluting with acetone/methylene chloride. The appropriate fractions are pooled to give the free amine of the title compound. A solution of methanesulfonic acid (1.44 g) in ether (80 ml) is added slowly to a solution of the free amino steroid (15 mmole) in methylene chloride (80 ml). The mixture is concentrated to a residue which is crystallized from methanol/ether to give the title compound.

EXAMPLE 140

16α-Methyl-17β-(1-oxo-4-[4-[4,6-bis(2-pyridinyl)-1,3,5-triazin-2-yl]-1-piperazinyl]butyl)androsta-4,9(11)-dien-3-one (I)

Following the general procedure of EXAMPLES 1-6A, 7, 8, 11–19, 83 and 126 and making non-critical variations but starting with 16α-methyl-17β-(1-oxo-[4-mesyloxy]butyl)] androsta-4,9(11)-dien-3-one (PREPARATION S-42) and 4-[4,6-bis(2-pyridinyl)-1,3,5-triazin-2-yl]piperazine (PREPARATION A-49) the title compound is obtained.

EXAMPLE 141

16α-Methyl-17β-(1-oxo-4-[4-[3-(ethylamino)-2-pyridinyl]-1-piperazinyl] butyl)androsta-4,9(11)-dien-3-one (I)

Following the general procedure of EXAMPLES 1-6A, 7, 8, 11–19, 83, 126 and 139 and making non-critical variations but starting with 16α-methyl-17β-(1-oxo-[4-mesyloxy]butyl)androsta-4,9(11)-dien-3-one (PREPARATION S-42) and 4-[6-(ethylamino)-2-pyridinyl] piperazine (PREPARATION A-47) the title compound is obtained.

EXAMPLE 142

21-[4-(4-Methoxyphenyl)-1-piperazinyl]-16α-methylpregna-1,4,9(11)-triene- 3,20-dione (I)

Following the general procedure of EXAMPLES 1-6A, 7, 8, 11–19, 83, 126 and 139 and making non-critical variations but starting with 4-(4-Methoxyphenyl)piperazine (PREPARATION A-31) and 21-iodo-16α-methylpregna-1,4,9(11)-triene-3,20-dione (PREPARATION S-22), the title compound is obtained.

EXAMPLE 143

21-[4-(3-Chlorophenyl)-1-piperazinyl]-16α-methylpregna-1,4,9(11)-triene- 3,20-dione (I)

Following the general procedure of EXAMPLES 1-6A, 7, 8, 11–19, 83, 126 and 139 and making non-critical variations but starting with 4-(3-chlorophenyl)piperazine (PREPARATION A-57) and 21-iodo-16α-methylpregna-1,4,9(11)-triene-3,20-dione (PREPARATION S-22), the title compound is obtained.

EXAMPLE 144

21-[4-[(3-Diethylamino)-2-pyridinyl]-1-piperazinyl]-16α-methylpregna- 1,4,9(11)-triene-3,20-dione (I)

Following the general procedure of EXAMPLES 1-6A, 7, 8, 11–19, 83, 126 and 139 and making non-critical variations but starting with 2-(3-diethylamino)pyridinylpiperazine (PREPARATION A-58) all 21-iodo-16α-methylpregna-1,4,9(11)-triene-3,20-dione (PREPARATION S-22), the title compound is obtained.

EXAMPLE 145

21-[4-[(5-Diethylamino)-2-pyridinyl]-1-piperazinyl]-16α-methylpregna- 1,4,9(11)-triene-3,20-dione (I)

Following the general procedure of EXAMPLES 1-6A, 7, 8, 11–19, 83, 126 and 139 and making non-critical variations but starting with 1-(5-diethylamino-2-pyridinyl)piperazine (PREPARATION A-59) and 21-iodo-16α-methylpregna-1,4,9(11)-triene-3,20-dione (PREPARATION S-22), the title compound is obtained.

EXAMPLE 146

21-[4-[(5-Ethylamino-6-diethylamino)-4-pyrimidinyl]-1-piperazinyl]-16α-methylpregna-1,4,9(11)-triene-3,20-dione (I)

Following the general procedure of EXAMPLES 1-6A, 7, 8, 11–19, 83, 126 and 139 and making non-critical variations but starting with 4-(5-ethylamino-6-diethylamino)pyrimidinylpiperazine (PREPARATION A-60) and 21-iodo-16α-methylpregna- 1,4,9(11)-triene-3,20-dione (PREPARATION S-22), the title compound is obtained.

EXAMPLE 147

21-[4-[(5-Amino-6-diethylamino)-4-pyrimidinyl]]-1-piperazinyl]-16α-methylpregna- 1,4,9(11)-triene-3,20-dione (I)

Following the general procedure of EXAMPLES 1-6A, 7, 8, 11–19, 83, 126 and 139 and making non-critical variations but starting with 4-(5-amino-6-diethylamino)pyrimidinylpiperazine (PREPARATION A-61) and 21-iodo-16α-methylpregna-1,4,9(11)-triene-3,20-dione (PREPARATION S-22), the title compound is obtained.

EXAMPLE 148

21-[4-(4,6-Bis(1-pyrrolidinyl)-1,3,5-triazin-2-yl)-1-piperazinyl]pregna- 4,17(20)-trans-diene-3,11,21-trione dihydrochloride (V)

Trimethylaluminum (2M hexane, 1.0 ml) is added slowly to a solution of 2,6-bis(1-pyrrolidinyl)- 4-(1-piperazinyl)-1,3,5-triazine (PREPARATION A-45, 0.609 g) in methylene chloride (5 ml). The mixture is stirred for 15 min, then a solution of 21-carboxy-3,3-dihydroxy-pregna- 5,17(20)-trans-dien-11-one 3,3-dimethyl ether 21-methyl ester (PREPARATION S-43, 0.853 g) in methylene chloride (6 ml) is added. The mixture is refluxed for 42 hr, then cooled and applied to a column of silica gel (100 g, acetone/methylene chloride, 20/80) and rinsed in with methylene chloride. The column is eluted with acetone/methylene chloride (20/80). The appropriate fractions are pooled, and concentrated to give a solid. The solid is dissolved in warm acetone (95 ml) and hydrochloric acid (1N, 5 ml) is added. After 3 hr, aqueous potassium bicarbonate (1N, 10 ml) is added, the mixture concentrated, and the residue partitioned between methylene chloride and awater. The phases are separated, the organic phase is dried over magnesium sulfate, concentrated to give the free amine of the title compound as a solid. The hydrochloride acid salt is made in the usual way to give the title compound.

EXAMPLE A

Conjugated Diene Formation Assay

The formation of conjugated dienes as assayed by Braughler, J. Neurochem., 44, 1282 (1985), Bucher, Fund. Applied Tox., 3, 222 (1983) and Tein, Arch. Biochem. Biophy., 216, 142 (1982) is a standard pharmacological laboratory procedure useful for identifying compounds which inhibit lipid peroxidation. Since lipid peroxidation is involved in the pathophysiology of central nervous system trauma, compounds which inhibit conjugated diene formation are useful in treating the conditions listed below.

Inhibition of conjugated diene formation as measured by any of the above procedures or the modified procedure below demonstrated usefulness in treating spinal trauma, mild and/or moderate to severe head injury, subarachnoid hemorrhage and subsequent cerebral vasospasm, ischemic (thromboembolic) stroke, muscular dystrophy, adriamycin cardiac toxicity, Parkinsonism, Alzheimer's disease, other degenerative neurological disorders, multiple sclerosis, organ damage during reperfusion after transplant, skin graft rejection, hemorrhagic, traumatic, or septic shock, severe burns, APDS, allergic reactions, emphysema and post burn pulmonary complication. Further, an inhibition of conjugated diene formation also demonstrates usefulness in preventing damage following cardiopulmonary resuscitation, neurological or cardiovascular surgery and cardiac infarction.

While not necessary to demonstrate conjugated diene inhibition, the above assays have been modified as follows: rat brain synaptosomes are prepared according to the procedure described in J. Neurochem. 44, 1282 (1985). Synaptosomal suspension (10 µl) is added to 1 ml of physiological (normal) saline containing 1% Lubrol PX (Sigma Chemical Co. St. Louis, Mo.), 100 µM hydrogen peroxide and 100 µM (or less) of the drug to be tested prepared in either absolute ethanol or water depending upon solubility.

The reaction is started by the rapid addition of 200 µM ferrous ammonium sulfate prepared in argon-purged water. The sample is rapidly mixed and the change in absorbance at 232 nm is followed in a Gifford Response Spectrophotometer equipped with a rapid sampler. Due to the rapidity of the reaction, rapid addition of the iron, rapid mixing and sampling are obligatory to the accuracy of the assay. For best results absorbence readings of one/sec should be started within 5 sec following the addition of iron. The initial linear rate of absorbence change during the first 30 sec of reaction are compared with the rate of a reaction containing all reagents except synaptosomes. The difference in rates is the rate of conjugated diene formation. Rates with drug are compared to rates obtained in the absence of drug and the % inhibition is calculated. A compound that inhibits conjugated diene formation by 50% or more is considered to be "active".

The compounds of Examples 2, 4, 5, 6B–8, 10–22, 24–28, 30–34, 36–41, 43–45, 47, 50–54, 58–76, 83, 84, 86, 93–99, 103–107, 111, 112 and 114–122 demonstrate such activity by inhibition of conjugated dienes.

The above in vitro test/assay is a standard pharmacological laboratory procedure for demonstrating compounds which are useful in treating the conditions listed above. Following the in vivo mouse head injury procedure of Hall, J. Neurosurg., 62, 882 (1985) compounds which statistically significantly ($p<0.05$) increase the 1 hr neurological recovery following head injury are considered preferred compounds for treating the above conditions, these are:

| % Increase in 1 hr Post-Injury Grip Test Scores After 3 mg/kg | Compound of Example |
|---|---|
| 200.8 | 127 |
| 199.7 | 69 |
| 184.4 | 109 |
| 148.3 | 70 |
| 134.5 | 83 |
| 112.6 | 18 |

EXAMPLE B

Arachidonic Acid Antagonism Assay (AAAA)

The Arachidonic Acid Antagonism Assay (AAAA) as set forth in Thrombosis Res., 9, 67 (1976) is a standard laboratory procedure for demonstrating antagonism of the effects of arachidonic acid metabolites. Since these metabolites contribute to the pathological problems associated with stroke, spinal trauma and head injury, compounds which antagonize arachidonic acid are useful in treating stroke, spinal trauma and head injury. Compounds which significantly elevate the $LD_{50}$ of arachidonic acid in animals are considered to be useful for the treatment of these conditions.

While not necessary to determine arachidonic acid antagonism, the above assay has been modified as follows: Charles River male CF-1 mice weighing 18–22 g are treated IV with the test compound dissolved in 1.0% Tween-80 and 0.1% hydrochloric acid in distilled water, 0.2 ml total volume. Fifteen minutes later sodium arachidonate (90% pure) in physiological (normal) saline is injected into the tail vein. The $LD_{50}$ is measured using the Spearman-Karber method with a log dose interval of 0.05 (N=6). Compounds which elevate the $LD_{50}$ outside of the 95% confidence interval of the control $LD_{50}$ are considered to be "active".

The compounds of Examples 2, 4, 11–17, 19, 21, 22, 24, 25, 29, 41, 45, 47, 51, 53, 54, 57, 60, 62, 74, 75, 93 and 99–101 demonstrate arachidonic acid antagonism.

The following are test results in the Arachidonic Acid Antagonism Assay for the compounds identified:

| % of Control LD$_{50}$ 100 mg/kg | Compound of Example No. |
| --- | --- |
| 150 | 17 |
| 141 | 19 |
| 138 | 62 |
| 124 | 57 |

EXAMPLE C

Malonyldialdehyde (MDA) Formation Assay

The MDA assays of Buege and Aust, Methods in Enzymology, Fleisher and Packer Editors, Academic Press, 1978, New York, Vol LII, p 302–310 and Kohn and Liversedge, J. Pharmacol. Exp. Ther. 82, 292 (1944) are standard pharmacological laboratory procedures for demonstrating the occurrence of lipid peroxidation by the formation of MDA. Since lipid peroxidation is involved in the pathophysiology of center nervous system trauma, compounds which inhibit MDA formation are useful in treating the conditions listed below.

MDA formation as measured by any of the above procedures or the modified procedure below demonstrates usefulness in treating spinal trauma, mild and/or moderate to severe head injury, subarachnoid hemorrhage and subsequent cerebral vasospasm, ischemic (thromboembolic) stroke, muscular dystrophy, adriamycin cardiac toxicity, Parkinsonism, Alzheimer's disease, other degenerative neurological disorders, multiple sclerosis, organ damage during reprefusion after transplant, skin graft rejection, hemorrhagic, traumatic and septic shock, severe burns, ARDS, allergic reactions, emphysema and post burn pulmonary complication. Further, MDA formation also demonstrates usefulness in preventing damage following cardiopulmonary resuscitation, neurological or cardiovascular surgery and cardiac infarction.

While not necessary to determine MDA formation, the above assays have been modified as follows: rat brain synaptosomes are prepared as described in the Example about the conjugated diene assay, except that the final wash of the synaptosomes and final suspension are in physiological (normal) saline in which the pH has been adjusted to 7.0. The synaptosomes are incubated for 10 min at 37° in physiological (normal) saline pH 7.0 (total volume=100 ul) containing; 10 ul synaptosomal suspension, 10% DMSO plus or minus drug, 150 uM $Fe^{+++}$ and 50 uM $Fe^{++}$. The incubation is started by the rapid addition of iron to the otherwise complete reaction. The iron solutions are prepared fresh as ferric chloride and ferrous ammonium sulfate in argon-purged water. Following the 10 min incubation, the reaction is stopped by the addition of 500 ul ice-cold 12% trichloroacetic acid prepared in 0.5N hydrochloric acid. Water (300 ul) is then added along with 100 ul of freshly prepared thiobarbituric acid (3.3% in 0.5N sodium hydroxide) and 10 ul of 5 mM desferrioxamine. The sample is then heated in a boiling water bath for 20 minutes. The samples are cooled and centrifuged for 15 minutes at 1500×g and the absorbence of the supernatant fraction is read at 532 nm. The % inhibition of MDA formation is calculated by dividing the absorbance of sample containing drug by the absorbence of samples incubated without drug. Reaction blanks are samples incubated in the absence of iron. A compound that inhibits MDA formation by 50% or more at a concentration of 200 μM or less is considered "active".

The compounds of Examples 17, 47, 49–52, 62, 67–71, 73–75, 83, 86, 95–97, 104, 107, 110, 111–113, 118, 120, 121, 125, 127 and 129 demonstrate such activity by inhibition of MDA formation.

The above in vitro test/assay is a standard pharmacological laboratory procedure for demonstrating compounds which are useful in treating the conditions listed above. Following the in vivo mouse head injury procedure of Hall, J. Neurosurg., 62, 882 (1985) compounds which statistically significantly (p<0.05) increase the 1 hr neurological recovery following head injury are considered preferred compounds for treating the above conditions, these are:

| % Increase in 1 hr Post-Injury Grip Test Scores After 3 mg/kg | Compound of Example |
| --- | --- |
| 200.8 | 127 |
| 199.7 | 69 |
| 184.4 | 109 |
| 148.3 | 70 |
| 134.5 | 83 |
| 112.6 | 18 |

EXAMPLE D

AcylCoA:Cholesterol Acyltransferase (ACAT) Inhibition Assay

ACAT esterifies arterial cholesterol which is a key reaction in the development of atherosclerosis. The procedure of Bell, Can. J. Biochem. 60, 967 (1982) provides a standard procedure for demonstrating which compounds inhibit ACAT and therefore inhibit formation of esterified arterial cholesterol thereby preventing atherosclerosis. In the ACAT assay it is preferred to use Fu5AH cells, see Lipids 9, 526 (1974). According to this procedure, compounds which inhibit ACAT activity equal to, or greater than, that of chloropromazine are considered "active".

The compounds of Examples 3, 17 and 18 are active in inhibiting ACAT.

The following are test results in the ACAT assay for the compounds identified:

| % Inhibition of ACAT (5 μg/ml) | Compound of Example |
| --- | --- |
| 63.9 | 3 |
| 48.4 | 18 |
| 32.2 | 17 |

EXAMPLE E

Antiatherosclerosis Screen in Susceptible to Experimental Atherosclerosis (SEA) Japanese Quail Demonstration of antiatherosclerotic activity of a compound in SEA Japanese Quail is done by showing that the compound reduces the serum and arterial cholesterol in quail fed an atherogenic diet. This standard laboratory procedure for demonstrating a reduction in arterial and serum cholesterol in SEA Japanese quail has been described by Stevens in Atherosclerosis 56, 313 (1985). While not necessary, some minor modifications for extraction of cholesterol from the artery have been made. Time are as follows: frozen arteries are homogenized in hexane/isopropanol (3/2) and the volume adjusted with Triton 100 solution (1.5% in hexane/isopropanol) to 7 ml. After standing 12 hr at 20°–25°, the supernatant, obtained by low speed centrifugation is evaporated until dry and thru the residue is suspended in 0.5 ml of 5% Triton 100 in isopropanol. This suspension is incubated for 10 min at 45° to dissolve the material. This solution as well as the diluted serum samples are analyzed for cholesterol by standard clinical chemistry analyzer methods. According to the above procedure compounds which decrease serum or arterial cholesterol >30% are considered to be "active".

Compounds which reduce serum and arterial cholesterol and are useful in treating atherosclerosis and its complications; for example, reduction of serum cholesterol by drugs reduces the incidence of coronary heart disease, JAMA 251, 351 (1984) and JAMA 251, 365 (1984).

The compound of Example 3 demonstrates reduction of serum and arterial cholesterol.

EXAMPLE F

Inhibition of Interleukin-1

The inhibition of interleukin-1 induced T cell proliferation assay, Proc. Nat. Acad. Sci. U.S.A., 78, 1133 (1981) is a standard laboratory procedure for demonstrating inhibition of interleukin-1 bioactivities. Since people with arthritis make excess interleukin 1, compounds which inhibit the activity of interleukin 1 are useful in the treatment of arthritis. According to this procedure compounds which inhibit the activity of interleukin 1 greater that 30% at $10^{-6}$M are considered to be "active".

The compounds of Examples 21, 37, 47, 83, 84, 86, 94, 96, 97, 101, 105 and 120 demonstrate inhibition of interleukin 1.

| % Inhibition at $10^{-6}$ M | Compound of Example |
|---|---|
| 84 | 86 |
| 77 | 96 |
| 76 | 105 |
| 62 | 83 |
| 56 | 120 |

EXAMPLE G

Inhibition of Mucous Secretion

The inhibition of mucous secretion assay of Johnson Int Arch. of Allergy and Applied Immunology 75, 97 (1984) is a standard pharmacological laboratory procedure for demonstrating inhibition of mucous secretions and therefore usefulness in preventing and/or treating mucous secretions, asthma, inflammatory lung diseases, bronchitis, allergic reactions and ARDS. According to this procedure compounds which inhibit or block enhancement of induced mucous secretions when tested are considered to be "active".

The compounds of Examples 2, 4, 16, 18, 83 and 105 demonstrate such activity. The test results disclose that the compounds of Examples 2, 83 and 105 are the preferred mucous inhibitors.

EXAMPLE H

Asthma Test in Ovalbumin Sensitized Guinea Pigs

The ovalbumin sensitized guinea pig test, Brit. J. Pharm. 78, 67 (1983) is a standard laboratory procedure for demonstrating inhibition of bronchoconstriction and therefore use in treating/preventing asthma. While not necessary the above test has been modified as follows. Male guinea pigs (500–700 g at the time of antigen challenge) am sensitized by IM injection of ovalbumin (5%, 0.35 ml) into each hind limb and repeated 6 days later. Five weeks after the initial injection of ovalbumin, the animals are anesthetized with urethane (1.5 g/kg intraperitoneally), the trachea cannulated and the lungs ventilated at constant volume using a Harvard Apparatus Rodent Respirator. Tracheal pressure is measured from a side-arm of the tracheal cannula via a Statham P23AC pressure transducer of a furness control micromanometer. The chest is opened along the mid-line. Bronchoconstriction is measured as the absolute increase in transpulmonary pressure in cm water with respect to the atmosphere. Blood pressure is recorded using a Statham P23Db pressure transducer vial a catheter inserted into a carotid artery. Heart rate is derived from the blood pressure signal using a Grass 7P4F tachograph. A jugular vein is catheterized for injection of drugs and antigen. The animals are pretreated with the following: indomethacin (10 mg/kg, 15 min prior to antigen), pyrilamine maleate (2 mg/kg, 10/11 min before antigen), and propranolol (0.25 mg/kg, 5 min prior to antigen). Antigen challenge consists of ovalbumin (0.3 mg/kg) given IV.

The compounds to be tested are administered by either IV (compound precedes the antigen challenge by four minutes), orally (fasted animals are dosed at either 2 or 4 hr prior to challenge) or by aerosol (the compound is nebulized thru the Harvard respirator and directly into the tracheal cannula 180 sec four min prior to the IV antigen challenge). Vehicles include IV (saline), oral (emulphor or 0.1% Tween 80) or for aerosol (DMSO).

The antigen provocation produces a slowly developing bronchoconstriction which lasts at least 15 min. The percent inhibition at various times points after antigen challenge compares the test compound to control animals (vehicle only). According to this procedure compounds which give 50% or greater inhibition at 10 mg/kg are considered to be "active".

EXAMPLE I

Inhibition of Tumor Growth

The feeble egg or chick embryo assay of Folkman, Science 221, 719 (1983) is the standard pharmacological laboratory procedure for demonstrating inhibition of angiogenesis, and therefore of tumor growth [Folkman, in Advances in Cancer Research, G. Klein and S. Weinhouse, ed., 43, 175 (1985)]. According to this procedure compounds which are considered to be "active" (i.e. antiangiogenic) give an avascular zone of 4 mm or greater in some embryos when tested at 50 µg/10 µl in the presence of 50 µg/10µ of heparin.

The compounds of Examples 2–5, 6B, 8–10, 12–18, 20, 21, 24, 26–30, 32, 33, 34, 36, 37, 39–41, 43–48, 51–55, 63, 64, 83, 86, 97, 99, 104 and 105 demonstrate inhibition of angiogenesis.

The following are test results in the Folkman assay for the compounds identified:

| % of Embryos with 4 mm or Greater Avascular Zone | Compound of Example No. |
|---|---|
| 91 | 21, 16 |
| 85 | 2 |
| 80 | 41 |
| 75 | 44 |
| 73 | 28 |
| 72 | 20 |

EXAMPLE J

Aspirin Induced Ulcer Test

The aspirin/cold induced ulcer assay of Rainsford, Agents and Actions 5, 553 (1975) is a standard pharmacological laboratory procedure for demonstrating anti-ulcer activity. According to this procedure compounds which give a 50% or more reduction of ulcer index are considered to be "active".

The compound of Example 16 demonstrates anti-ulcer activity.

CHART A

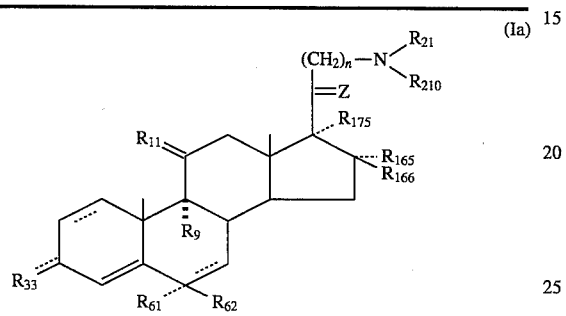
(Ia)

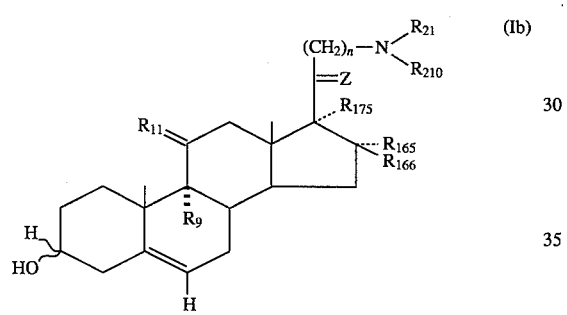
(Ib)

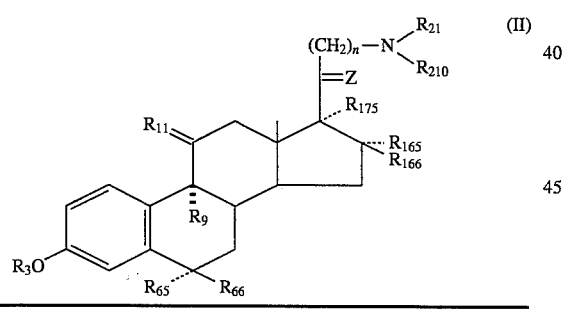
(II)

CHART B

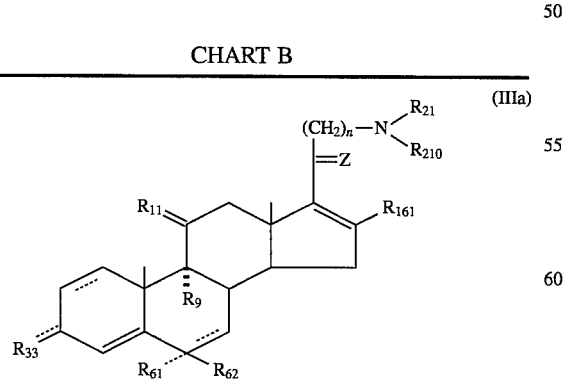
(IIIa)

CHART B-continued

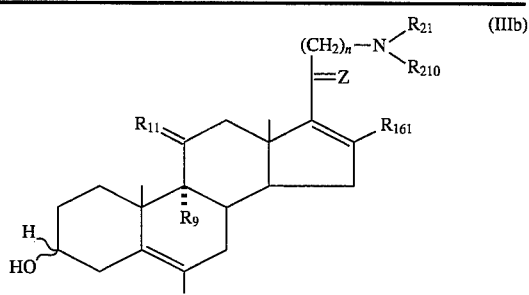
(IIIb)

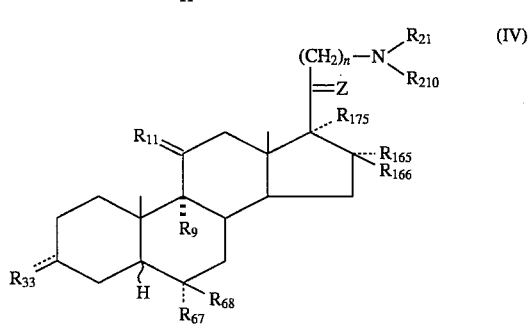
(IV)

CHART C

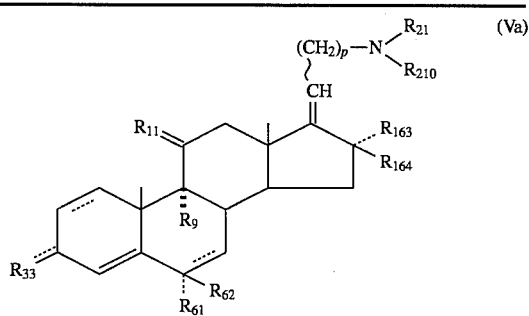
(Va)

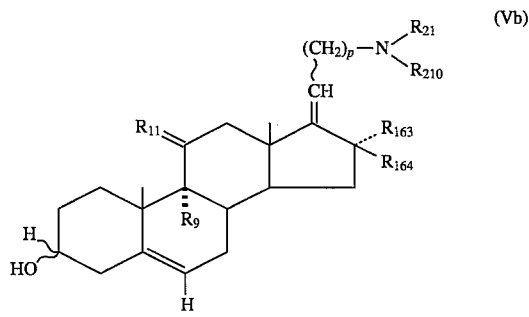
(Vb)

CHART C-continued

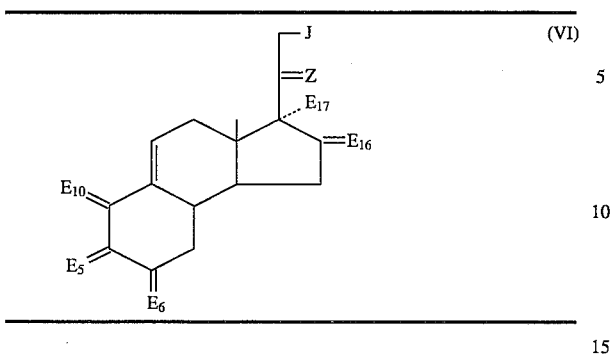

(VI)

CHART D

| Name | Chemical Structure $R_{21}/R_{210}$ | Formula No. |
|---|---|---|
| 1-piperazinyl-($C_2$–$C_4$) optionally substituted in the 4-position | —($C_2$–$C_4$ alkyl)-N⟨ ⟩N—($X_1$ or $X_2$) | [B] |
| 1-piperazinylacetyl substituted in the 4-position | -acetyl-N⟨ ⟩N—$X_2$ | [L] |
| 1-piperazinylcarbonylmethyl substituted in the 4-position | -carbonylmethyl-N⟨ ⟩N—$X_2$ | [M] |
| 2-(carboxy)-1-pyrrolidinyl | —N⟨pyrrolidine⟩-COOH | [C-1] |
| 2-(carboxy)-1-piperidinyl | —N⟨piperidine⟩-COOH | [C-2] |
| 2-(carboxy)-1-hexamethyleneimino | —N⟨hexamethyleneimine⟩-COOH | [C-3] |
| 2-(carboxy)-1-heptamethyleneimino | —N⟨heptamethyleneimine⟩-COOH | [C-4] |
| 1-piperazinyl substituted in the 4-position | —N⟨ ⟩N—$(CH_2)_j$—CO—$R_{228}$ | [D] |

CHART D-continued

$R_{21}/R_{210}$

| Name | Chemical Structure | Formula No. |
|---|---|---|
| 1-piperazinyl substituted in the 4-position | 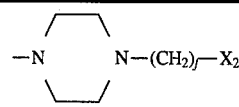 $-N\underset{\smile}{\overset{\frown}{\phantom{X}}}N-(CH_2)_j-X_2$ | [E] |
| 1-piperazinyl substituted in the 4-position | 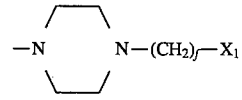 $-N\underset{\smile}{\overset{\frown}{\phantom{X}}}N-(CH_2)_j-X_1$ | [F] |
| 4-hydroxy-1-piperidinyl substituted in the 4-position | 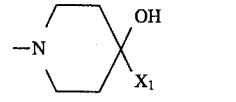 piperidine with OH and $X_1$ at 4-position | [G] |
| 1-piperazinyl substituted in the 4-position | 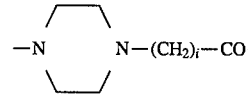 $-N\underset{\smile}{\overset{\frown}{\phantom{X}}}N-(CH_2)_i-CO-NR_{229}-X_2$ | [N] |

CHART E

$R_{212}$

| Name | Chemical Structure | Formula No. |
|---|---|---|
| *$CH_2-(CH_2)_c-G-(CH_2)_d-CH_2-N^*-$ | 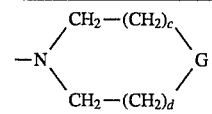 | [a] |
| 3-pyrrolin-1-yl |  | [b] |
| pyrrol-1-yl optionally substituted | 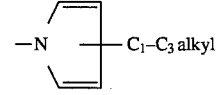 $C_1-C_3$ alkyl | [c] |
| piperidin-1-yl optionally substituted | 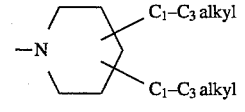 $C_1-C_3$ alkyl, $C_1-C_3$ alkyl | [d] |
| 1,2,3,6-tetrahydropyridin-1-yl | 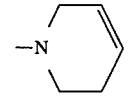 | [e] |
| 1-hexamethyleneimino containing a 3- or 4- double bond or 3- and 5- double bonds | 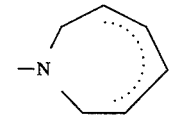 | [f] |
| 1,4-dihydro-1-pyridinyl substituted in the 4-position | 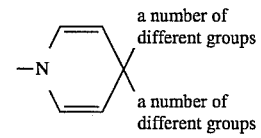 a number of different groups / a number of different groups | [g] |

CHART F

$X_2$

| Name | Chemical Structure | Formula No. |
|---|---|---|
| pyridin-2-, | 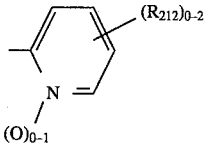 | (1) |
| 3-, | 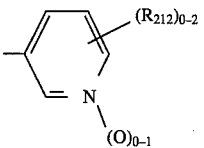 | (2) |
| or 4-yl optionally substituted optionally as the N-oxide | 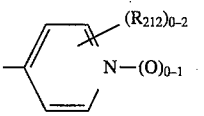 | (3) |
| 1,3,5-triazin-2-yl or the N-oxide thereof optionally substituted at the 4- and/or 6- position | 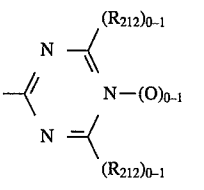 | (4) |
| pyrimidin-4-yl or the N-oxide thereof optionally substituted at the 2- and/or 6- position | 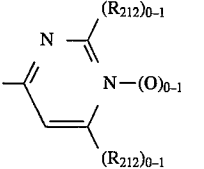 | (5) |
| pyrimidin-2-yl optionally substituted | 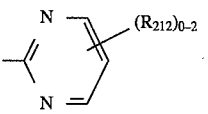 | (6) |
| pyrazin-2-yl optionally substituted | 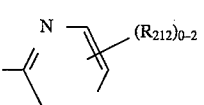 | (7) |
| imidazol-2-yl optionally substituted | 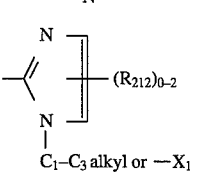 | (8) |
| 1,2,4-triazol-3-yl optionally substituted | 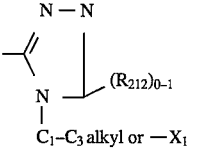 | (9) |
| imidazol-4- or 5-yl optionally substitued | 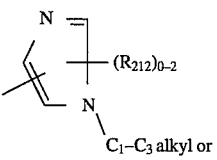 | (10) |

CHART F-continued

X₂

| Name | Chemical Structure | Formula No. |
|---|---|---|
| benzo[b]thien-2-yl | | (12a) |
| indol-2-yl | | (12b) |
| benzo[b]thiazol-2-yl | | (12c) |
| benzimidazol-2-yl | | (12d) |
| 4-[2-[4-[2,6-bis-(1-pyrrolidinyl)-4-pyrimidinyl]-1-piperazinyl]ethyl]-piperazinyl | —CH₂CH₂—N (structure shown) | (13) |
| 1,2,4-triazol-3-yl optionally substituted at the 5- and/or 6-position | (structure with $(R_{212})_{0-1}$) | (14) |

CHART G

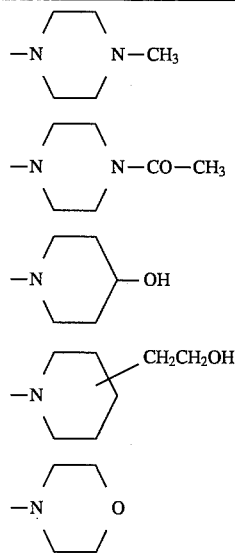

| | |
|---|---|
| —N⌒N—CH₃ | J1 |
| —N⌒N—CO—CH₃ | J2 |
| —N⌒—OH | J3 |
| —N⌒—CH₂CH₂OH | J4 |
| —N⌒O | J5 |

CHART H

| Compound of Example | Physical Data | |
|---|---|---|
| | m.p. | MS [M + H]⁺ |
| 0 | See specification | |
| 1 | None | |
| 2 | 213–215° | |
| 3 | 189–194° dec | |
| 4 | 170–174° dec | 577 |
| 5 | 203–205° | 572 |
| 6A | 172–174° | |
| 6B | 195–197° | |
| 7 | 200–203° | 546 |
| 8 | 209–211° | 491 |
| 9 | 108–110° | 561 |
| 10 | 174–175.5° | 566, 568 |
| 11 | 164–166° | 520 |
| 12 | 240–245° | 568, 570 |
| 13 | 215–216° | 519 |
| 14 | 195–200° | 631 |
| 15 | 189–194° | 660 |
| 16 | 184–186° | 633 |
| 17 | 154–159° | 645 |
| 18 | 184–190° | 645 |
| 19 | | 687 |
| 20 | 154–157° | |

CHART H-continued

| Compound of Example | m.p. | MS [M + H]+ |
|---|---|---|
| 21 | 145–148° | |
| 22 | 228–231° | |
| 23 | 245° | |
| 24 | 187° dec | 491 |
| 25 | | 505 |
| 26 | | 522 |
| 27 | | 534 |
| 28 | | 505 |
| 29 | | 524 |
| 30 | | 537 |
| 31 | | 601 |
| 32 | | 635 |
| 33 | | 549 |
| 34 | | 538 |
| 35 | 233° dec | |
| 36 | | 491 |
| 37 | | 688 |
| 38 | | 503 |
| 39 | 273–275° dec | |
| 40 | 201° dec | |
| 41 | 210° dec | 535 |
| 42 | 219° dec | 563 |
| 43 | 219° dec | 492 |
| 44 | 204° dec | |
| 45 | 202° dec | |
| 46 | 192° | |
| 47 | 193–196° dec | 641 |
| 48 | 243–250° dec | |
| 49 | 197–208° dec | |
| 50 | | 651 |
| 51 | | 641 |
| 52 | | 572 |
| 53 | 218° dec | 635 |
| 54 | 143–146° | 503 |
| 55 | 139–142° | |
| 56 | | 478 |
| 57 | | 620 |
| 58 | 169° dec | |
| 59 | 181° dec | |
| 60 | 184° dec | |
| 61 | 142° dec | |
| 62 | 190–195° | |
| 63 | 195–196° | |
| 64 | 156–158° | |
| 65 | | 473 |
| 66 | | 505 |
| 67 | | 630 |
| 68 | | 575 |
| 69 | | 634 |
| 70 | | 648 |
| 71 | 185° dec | |
| 72 | 182° | |
| 73 | 220–230° dec | |
| 74 | 215° dec | |
| 75 | 165–175° dec | |
| 76 | 160–165° | |
| 83 | | 625 |
| 84 | 215° dec. | |
| 86 | 127° dec | 657 |
| 92 | 220–225° dec | |
| 93 | 134–135° | |
| 94 | 221° dec | |
| 95 | 217° dec | |
| 96 | 182° dec | |
| 97 | 217° dec | |
| 98 | 173° dec | |
| 99 | 195° dec | |
| 100 | 152–155° | |
| 101 | 139–140° | 426 |
| 102 | See specification | |
| 103 | See specification | |
| 104 | 212–214° dec | 599 |
| 105 | 205–208° dec | 661 |
| 106 | 243–245° dec | 479 |
| 107 | | 615 |
| 108 | | 476 |
| 109 | 181–185 dec | |
| 110 | 230° | |
| 111 | 210° dec | |
| 112 | | 613 |
| 113 | | 609 |
| 114 | 219° dec | |
| 115 | 215–222° dec | 741 (M+) |
| 116 | | 644 (M+) |
| 117 | | 664 (M+) |
| 118 | | 660 (M+) |
| 119 | | 522 (M+) |
| 120 | | 615 (M+) |
| 121 | | 626 (M+) |
| 122 | | 627 (M+) |
| 125 | 164° dec | 629 (M+) |
| 126 | 152–154° | 630 |
| 127 | 194° dec | |
| 129 | 179–185° dec | 615 (M+) |
| 130 | 151–154° | |
| 131 | 159–162° | |
| 132 | | 623 (M+) |
| 133 | 212–215° | |
| 135 | 260–265° | |
| 142 | | 514 (M+) |
| 143 | | 518 (M+) |
| 144 | | 557 |
| 145 | | 556 |
| 146 | | 600 |
| 147 | | 572 |
| 148 | 182° | |

We claim:

1. An amino substituted steroid of formula XI

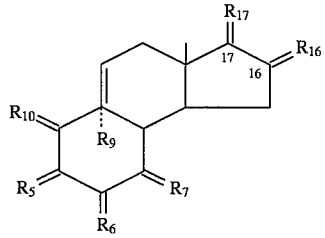

where:

$R_6$ is $\alpha$-$R_{61}$:$\beta$-$R_{62}$, $R_{10}$ is $\alpha$-$R_{101}$:$\beta$-$R_{102}$ and $R_7$ is $\alpha$-H:$\beta$-H, where one of $R_{61}$ and $R_{62}$ is —H, and the other is —H, —F, or $C_1$-$C_3$ alkyl, $R_{102}$ is —$CH_3$, $R_{101}$ and $R_5$ taken together are —$(CH_2)_2$—C(=$R_{33}$)—CH= or —CH=CH—CO—CH=, where $R_{33}$ is =O or $\alpha$-H:$\beta$-$OR_{34}$ or $\alpha$-$OR_{34}$:$\beta$-H, where $R_{34}$ is —H, —CO—$CH_3$, —CO—$C_2H_5$, —CO—$C_6H_5$, —CO—O—$CH_3$ or —CO—O—$C_2H_5$;

$R_{16}$ is $\alpha$-$R_{165}$:$\beta$-$R_{166}$ and $R_{17}$ is $\alpha$-$R_{175}$:$\beta$-$R_{176}$, where $R_{165}$ is —H, —OH, —F or —$CH_3$ and $R_{166}$ is —H, —OH, —F, or —$CH_3$, with the proviso that at least one of $R_{165}$ and $R_{166}$ is —H, where $R_{175}$ is —H, —OH, —$CH_3$, —$CH_2CH_3$, $C_2$-$C_7$ alkanoyloxy or —O—CO—$X_1$, where $X_1$ is phenyl optionally substituted with 1 or 2 —Cl, —Br, $C_1$-$C_3$ alkoxy, —COOH, —$NH_2$, $C_1$-$C_3$ alkylamino, di($C_1$-$C_3$)alkylamino where the alkyl groups are the same or different, 1-pyrrolidinyl-, 1-piperidinyl, 1-hexamethylenimino, 1-heptamethylenimino-, $C_2$-$C_4$ acylamino and —NH—CHO or with 1 —F or —$CF_3$; where $R_{176}$ is —C(=Z)—$(CH_2)_n$—$NR_{21}R_{210}$, where Z is =O, where n is 1, where $R_{21}$ and $R_{210}$ are taken together with the attached nitrogen atom to form 1-piperazinyl substituted in the 4- position with $X_2$—$(CH_2)_j$—, where j is 0 or 1 [E] and $X_2$ is:

(1) imidazol-2-yl optionally substituted in the 1 position with (8) $C_1$–$C_8$ alkyl or —$X_1$, where $X_1$ is as defined above, and further optionally substituted with 1 or 2 $R_{212}$ where the $R_{212}$'s are the same or different and are (iv) $C_1$–$C_5$ alkyl, (vi) —$X_1$, where $X_1$ is as defined above, (vii) —$NR_{213}R_{213}$ where the $R_{213}$'s are the same or different and are —H or $C_1$–$C_3$ alkyl, (viiiα) *$CH_2$—$(CH_2)_q$—$CH_2$—N*— where the atoms marked with an asterisk (*) are bonded to each other resulting in the formation of a ring, where q is 1 through 5, (viiiβ) *$CH_2$—$CH_2$—$(CH_2)_c$—G—$(CH_2)_d$—$CH_2$—$CH_2$—N*— where the atoms marked with an asterisk (*) are bonded to each other resulting in the formation of a ring, where G is —O— or —$NHR_{214}$, where $R_{214}$ is —H, $C_1$–$C_3$ alkyl, or $X_1$ as defined above, where c and d are the same or different and are 0 through 2 with the proviso that the total number of ring carbon atoms in 4, 5 or 6, [a]

(xv) —OH, (xvi) $C_1$–$C_3$ alkoxy, (2) imidazol-4- or 5-yl optionally substituted in the 1 position with $C_1$–$C_3$ alkyl or —$X_1$, where $X_1$ is as defined above, and further optionally substituted with 1 or 2 $R_{212}$ as defined above, and pharmaceutically acceptable salts, (10) hydrates and solvates thereof.

2. An amino substituted steroid according to claim 1 where $R_{101}$ and $R_5$ taken together are —$(CH_2)_2$—C(=$R_{33}$)—CH= or —CH=CH—CO—CH=, where $R_{33}$ is =O.

3. An amino substituted steroid according to claim 1 where j is 0.

4. An amino substituted steroid according to claim 1 where the pharmaceutically acceptable salt is selected from the group consisting of hydrochloride, hydrobromide, hydrogen iodide, sulfate, phosphate, acetate, lactate, citrate, succinate, benzoate, salicyclate, pamoate, cyclohexanesulfamate, methanesulfonate, naphthalenesulfonate, p-toluenesulfonate, maleate, fumarate and oxalate.

* * * * *